(12) United States Patent
Ni et al.

(10) Patent No.: US 6,743,625 B2
(45) Date of Patent: Jun. 1, 2004

(54) DEATH DOMAIN CONTAINING RECEPTOR 5

(75) Inventors: Jian Ni, Rockville, MD (US); Reiner L. Gentz, Rockville, MD (US); Guo-Liang Yu, Berkeley, CA (US); Craig A. Rosen, Laytonsville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/874,138

(22) Filed: Jun. 6, 2001

(65) Prior Publication Data

US 2002/0072091 A1 Jun. 13, 2002

Related U.S. Application Data

(63) Continuation of application No. 09/565,009, filed on May 4, 2000, and a continuation-in-part of application No. 09/042,583, filed on Mar. 17, 1998.
(60) Provisional application No. 60/148,939, filed on Aug. 13, 1999, provisional application No. 60/133,238, filed on May 7, 1999, provisional application No. 60/132,498, filed on May 4, 1999, provisional application No. 60/042,583, filed on Mar. 17, 1998, provisional application No. 60/054,021, filed on Jul. 29, 1997, and provisional application No. 60/040,846, filed on Mar. 17, 1997.

(51) Int. Cl.$^7$ .................. C07K 14/705; C12N 5/10; C12N 15/12
(52) U.S. Cl. ............. 435/325; 530/350; 536/23.1; 536/23.4; 536/23.5; 435/69.1; 435/252.3; 435/254.11
(58) Field of Search ............ 530/350; 536/23.1, 536/23.5, 23.4; 435/320.1, 69.1, 325, 252.3, 254.11

(56) References Cited

U.S. PATENT DOCUMENTS

| | | | |
|---|---|---|---|
| 4,002,531 A | 1/1977 | Royer | |
| 4,946,778 A | 8/1990 | Ladner et al. | |
| 5,349,053 A | 9/1994 | Landolfi | |
| 5,447,851 A | 9/1995 | Beutler et al. | |
| 5,478,925 A | 12/1995 | Wallach et al. | |
| 5,530,101 A | 6/1996 | Queen et al. | |
| 5,565,332 A | 10/1996 | Hoogenboom et al. | |
| 5,643,575 A | 7/1997 | Martinez et al. | |
| 5,763,223 A | 6/1998 | Wiley et al. | |
| 5,807,715 A | 9/1998 | Morrison et al. | |
| 6,072,047 A | 6/2000 | Rauch et al. | |
| 6,313,269 B1 | 11/2001 | Deen et al. | |
| 6,342,369 B1 | 1/2002 | Ashkenazi | |
| 6,569,642 B1 | 5/2003 | Rauch et al. | |

FOREIGN PATENT DOCUMENTS

| | | |
|---|---|---|
| CA | 2045869 | 12/1991 |
| EP | 0 239 400 B1 | 9/1987 |
| EP | 0 401 384 B1 | 12/1990 |
| EP | 0 510 691 A1 | 10/1992 |
| EP | 0 870 827 A2 | 10/1998 |
| WO | WO 91/06570 | 5/1991 |
| WO | WO 91/09967 | 7/1991 |
| WO | WO 94/01548 | 1/1994 |
| WO | WO 95/06058 | 3/1995 |
| WO | WO 98/32856 | 7/1998 |
| WO | WO 98/35986 | 8/1998 |
| WO | WO 98/46643 A1 | 10/1998 |
| WO | WO 98/51793 A1 | 11/1998 |
| WO | WO 99/00423 A1 | 1/1999 |
| WO | WO 99/02653 | 1/1999 |

OTHER PUBLICATIONS

Brojatsch, J., et al., "CAR1, a TNFR–Related Protein, Is a Cellular Receptor for Cytopathic Avian Leukosis–Sarcoma Viruses and Mediates Apoptosis," *Cell* 87:845–855, Cell Press (Nov. 1996).

Chapman, B.S., "A region of the 75 kDa neurotrophin receptor homologous to the death domains of TNFR–1 and Fas," *FEBS Lett.* 374:216–220, Elsevier (1995).

Rablzadeh, S., et al., "Induction of Apoptosis by the Low–Affinity NGF Receptor," *Science* 261:345–348, American Association for the Advancement of Science (1993).

Tartaglia, L.A., et al., "A Novel Domain within the 55 kd TNF Receptor Signals Cell Death," *Cell* 74:845–853, Cell Press (1993).

Copy of provisional U.S. application 60/054,021, inventor NI et al., filed Jul. 29, 1997.

Copy of U.S. application 08/857,216, Inventor Ashkenazi, filed May 15, 1997.

Beutler, B., and Cerami, A., "Tumor Necrosis, Cachexia, Shock, and Inflammation: A Common Mediator," *Ann. Rev. Biochem.* 57:505–518, Annual Reviews Inc. (1988).

Fiers, W., "Tumor necrosis factor. Characterization at the molecular, cellular and in vivo level," *FEBS Lett.* 285:199–212, Elsevier Science B.V. (1991).

Goeddel, D.V., et al., "Tumor Necrosis Factors: Gene Structure and Biological Activities," *Cold Spring Harb. Symp. Quant. Biol. 51(Pt. 1)*:597–609, Cold Spring Harbor Laboratory Press (1986).

Golstein, P., "Cell death: TRAIL and its receptors," *Curr. Biol.* 7:R750–R753, Current Biology Ltd. (Dec. 1997).

(List continued on next page.)

Primary Examiner—Lorraine Spector
Assistant Examiner—Claire M. Kaufman
(74) Attorney, Agent, or Firm—Sterne, Kessler, Goldstein & Fox P.L.L.C.

(57) ABSTRACT

The present invention relates to novel Death Domain Containing Receptor-5 (DR5) proteins which are members of the tumor necrosis factor (TNF) receptor family, and have now been shown to bind TRAIL. In particular, isolated nucleic acid molecules are provided encoding the human DR5 proteins. DR5 polypeptides are also provided as are vectors, host cells and recombinant methods for producing the same. The invention further relates to screening methods for identifying antagonists and antagonists of DR5 activity.

48 Claims, 12 Drawing Sheets

OTHER PUBLICATIONS

Gruss, H.–J., and Dower, S.K., "Tumor Necrosis Factor Ligand Superfamily: Involvement in the Pathology of Malignant Lymphomas," *Blood 85*:3378–3404, The American Society of Hematology (1995).

Locksley, R.M., et al., "The TNF and TNF Receptor Superfamilies: Integrating Mammalian Biology," *Cell 104*:487–501, Cell Press (Feb. 2001).

Nagata, S., "Apoptosis by Death Factor," *Cell 88*:355–365, Cell Press (Feb. 1997).

Old, L.J., "Tumor Necrosis Factor," *Scientific American*, pp. 59–75, Scientific American, Inc. (May 1988).

Wallach, D., "TNF Ligand and TNF/NGF Receptor Families," in *Cytokine Reference. A compendium of cytokines and other mediators of host defense*, Oppenheim, J.J., et al., eds., Academic Press, Inc., San Diego, CA, pp. 377–411 (Aug. 2000).

Chaudhary, P.M., et al., "Death Receptor 5, a New Member of the TNFR Family, and DR4 Induce FADD–Dependent Apoptosis and Activate the NF–kB Pathway," *Immunity 7*:821–830, Cell Press (Dec. 1997).

Chinnaiyan, A.M., et al., "Signal Transduction by DR3, a Death Domain–Containing Receptor Related to TNFR–1 and CD95," *Science 274*:990–992, American Association for the Advancement of Science (Nov. 1996).

Delgado, C., et al., "The Uses and Properties of PEGLinked Proteins," *Crit. Rev. Ther. Drug Carrier Sys. 9*:249–304, CRC Press, Inc. (1992).

Huston, J.S., et al., "Protein Engineering of Single–Chain Fv Analogs and Fusion Proteins," *Meth. Enzymol. 203*:46–88, Academic Press, Inc. (1991).

Marsters, S.A., et al., "A novel receptor for APO2L/TRAIL contains a truncated death domain," *Curr. Biol. 7*:1003–1006, Current Biology Ltd. (Dec. 1997).

Morpurgo, M., et al., "Covalent Modification of Mushroom Tyrosinase with Different Amiphiphic Polymers for Pharmaceutical and Biocatalysis Applications," *Appl. Biochem. Biotechnol. 56*:59–72, Humana Press Inc. (Jan. 1996).

Morrison, S.L., "Transfectomas Provide Novel Chimeric Antibodies," *Science 229*:1202–1207, American Association for the Advancement of Science (1985).

Pan, G., et al., "The Receptor for the Cytotoxic Ligand TRAIL," *Science 276*:111–113, American Association for the Advancement of Science (Apr. 1997).

Pan, G., et al., "An Antagonist Decoy Receptor and a Death Domain–Containing Receptor for TRAIL," *Science 277*:815–818, American Association for the Advancement of Science (Aug. 1997).

Rieger, J., et al., "APO2 ligand: a novel lethal weapon against malignant glioma?"*FEBS Lett. 427*:124–128, Federation of European Biochemical Societies (May 1998).

Roguska, M.A., et al., "Humanization of murine monoclonal antibodies through variable domain resurfacing," *Proc. Natl. Acad. Sci. USA 91*:969–973, National Academy of Sciences (1994).

Schneider, P., et al., "TRAIL Receptors 1 (DR4) and 2 (DR5) Signal FADD–Dependent Apoptosis and Activate NF–kB," *Immunity 7*:831–836, Cell Press (Dec. 1997).

Sheikh, S.M., et al., "p53–dependent and –independent Regulation of the Death Receptor *KILLER/DR5* Gene Expression in Response to Genotoxic Stress and Tumor Necrosis Factor α," *Cancer Res. 58*:1593–1598, American Association for Cancer Research (Apr. 1998).

Sheridan, J.P., et al., "Control of TRAIL–Induced Apoptosis by a Family of Signaling and Decoy Receptors," *Science 277*:818–821, American Association for the Advancement of Science (Aug. 1997).

Uhlén, M., et al., "Fusion proteins in biotechnology and structural biology," *Curr. Opin. Biotechnol. 3*:363–369, Current Biology Ltd. (1992).

Wiley, S.R., et al., Identification and Characterization of a New Member of the TNF Family that Induces Apoptosis, *Immunity 3*:673–682, Cell Press (1995).

Zamai, L., et al., "Natural killer (NK) Cell–mediated Cytotoxicity: Differential Use of TRAIL and Fas Ligand by Immature and Mature Primary Human NK Cells," *J. Exp. Med. 188*:2375–2380, Rockefeller University Press (Dec. 1998).

NCBI Entrez, Genbank Report, Accession No. Z66083, from MacDonald, M., et al. (Oct. 1995).

NCBI Entrez, Genbank Report, Accession No. AA223122, from Hillier, L., et al. (Feb. 1997).

NCBI Entrez, Genbank Report, Accession No. AA232440, from Hillier, L., et al. (Feb. 1997).

Copy of provisional U.S. application 60/040,846, inventor Ni et al., filed Mar. 17, 1997.

```
             10                  30                    50
CACGCGTCCGCGGGCGCGGCCGGAGAACCCCGCAATCTTTGCGCCCACAAAATACACCGA
             70                  90                   110
CGATGCCCGATCTACTTTAAGGGCTGAAACCCACGGGCCTGAGAGACTATAAGAGCGTTC
            130                 150                   170
CCTACCGCCATGGAACAACGGGGACAGAACGCCCCGGCCGCTTCGGGGGCCCGGAAAAGG
              M  E  Q  R  G  Q  N  A  P  A  A  S  G  A  R  K  R
            190                 210                   230
CACGGCCCAGGACCCAGGGAGGCGCGGGGAGCCAGGCCTGGGCCCCGGGTCCCCAAGACC
 H  G  P  G  P  R  E  A  R  G  A  R  P  G  P  R  V  P  K  T
            250                 270                   290
CTTGTGCTCGTTGTCGCCGCGGTCCTGCTGTTGGTCTCAGCTGAGTCTGCTCTGATCACC
 L  V  L  V  V  A  A  V  L  L  L  V  S  A  E  S  A  L  I  T
            310                 330                   350
CAACAAGACCTAGCTCCCCAGCAGAGAGCGGCCCCACAACAAAAGAGGTCCAGCCCCTCA
 Q  Q  D  L  A  P  Q  Q  R  A  A  P  Q  Q  K  R  S  S  P  S
            370                 390                   410
GAGGGATTGTGTCCACCTGGACACCATATCTCAGAAGACGGTAGAGATTGCATCTCCTGC
 E  G  L  C  P  P  G  H  H  I  S  E  D  G  R  D  C  I  S  C
            430                 450                   470
AAATATGGACAGGACTATAGCACTCACTGGAATGACCTCCTTTTCTGCTTGCGCTGCACC
 K  Y  G  Q  D  Y  S  T  H  W  N  D  L  L  F  C  L  R  C  T
            490                 510                   530
AGGTGTGATTCAGGTGAAGTGGAGCTAAGTCCCTGCACCACGACCAGAAACACAGTGTGT
 R  C  D  S  G  E  V  E  L  S  P  C  T  T  T  R  N  T  V  C
            550                 570                   590
CAGTGCGAAGAAGGCACCTTCCGGGAAGAAGATTCTCCTGAGATGTGCCGGAAGTGCCGC
 Q  C  E  E  G  T  F  R  E  E  D  S  P  E  M  C  R  K  C  R
            610                 630                   650
ACAGGGTGTCCCAGAGGGATGGTCAAGGTCGGTGATTGTACACCCTGGAGTGACATCGAA
 T  G  C  P  R  G  M  V  K  V  G  D  C  T  P  W  S  D  I  E
            670                 690                   710
TGTGTCCACAAAGAATCAGGCATCATCATAGGAGTCACAGTTGCAGCCGTAGTCTTGATT
 C  V  H  K  E  S  G  I  I  I  G  V  T  V  A  A  V  V  L  I
            730                 750                   770
GTGGCTGTGTTTGTTTGCAAGTCTTTACTGTGGAAGAAAGTCCTTCCTTACCTGAAAGGC
 V  A  V  F  V  C  K  S  L  L  W  K  K  V  L  P  Y  L  K  G
            790                 810                   830
ATCTGCTCAGGTGGTGGTGGGGACCCTGAGCGTGTGGACAGAAGCTCACAACGACCTGGG
 I  C  S  G  G  G  D  P  E  R  V  D  R  S  S  Q  R  P  G
```

FIG.1A

```
      850                  870                  890
GCTGAGGACAATGTCCTCAATGAGATCGTGAGTATCTTGCAGCCCACCCAGGTCCCTGAG
 A  E  D  N  V  L  N  E  I  V  S  I  L  Q  P  T  Q  V  P  E
      910                  930                  950
CAGGAAATGGAAGTCCAGGAGCCAGCAGAGCCAACAGGTGTCAACATGTTGTCCCCCGGG
 Q  E  M  E  V  Q  E  P  A  E  P  T  G  V  N  M  L  S  P  G
      970                  990                 1010
GAGTCAGAGCATCTGCTGGAACCGGCAGAAGCTGAAAGGTCTCAGAGGAGGAGGCTGCTG
 E  S  E  H  L  L  E  P  A  E  A  E  R  S  Q  R  R  R  L  L
     1030                 1050                 1070
GTTCCAGCAAATGAAGGTGATCCCACTGAGACTCTGAGACAGTGCTTCGATGACTTTGCA
 V  P  A  N  E  G  D  P  T  E  T  L  R  Q  C  F  D  D  F  A
     1090                 1110                 1130
GACTTGGTGCCCTTTGACTCCTGGGAGCCGCTCATGAGGAAGTTGGGCCTCATGGACAAT
 D  L  V  P  F  D  S  W  E  P  L  M  R  K  L  G  L  M  D  N
     1150                 1170                 1190
GAGATAAAGGTGGCTAAAGCTGAGGCAGCGGGCCACAGGGACACCTTGTACACGATGCTG
 E  I  K  V  A  K  A  E  A  A  G  H  R  D  T  L  Y  T  M  L
     1210                 1230                 1250
ATAAAGTGGGTCAACAAAACCGGGCGAGATGCCTCTGTCCACACCCTGCTGGATGCCTTG
 I  K  W  V  N  K  T  G  R  D  A  S  V  H  T  L  L  D  A  L
     1270                 1290                 1310
GAGACGCTGGGAGAGAGACTTGCCAAGCAGAAGATTGAGGACCACTTGTTGAGCTCTGGA
 E  T  L  G  E  R  L  A  K  Q  K  I  E  D  H  L  L  S  S  G
     1330                 1350                 1370
AAGTTCATGTATCTAGAAGGTAATGCAGACTCTGCCATGTCCTAAGTGTGATTCTCTTCA
 K  F  M  Y  L  E  G  N  A  D  S  A  M  S  *
     1390                 1410                 1430
GGAAGTGAGACCTTCCCTGGTTTACCTTTTTTCTGGAAAAAGCCCAACTGGACTCCAGTC
     1450                 1470                 1490
AGTAGGAAAGTGCCACAATTGTCACATGACCGGTACTGGAAGAAACTCTCCCATCCAACA
     1510                 1530                 1550
TCACCCAGTGGATGGAACATCCTGTAACTTTTCACTGCACTTGGCATTATTTTTATAAGC
     1570                 1590
TGAATGTGATAATAAGGACACTATGGAAAAAAAAAAAAAA
```

```
241 T L S Q V - - - - - - - K G F V R K N G V N E A K I D E I K N D N V Q D T A    h Fas protein
358 T L Y A V V E N V P P L R W K E F V R R L G L S D H E I D R L E L Q N G R C L R  h TNFR I Protein
335 - L Y D V M D A V P A R R W K E F V R T L G L R E A I E A V E V E I G R - F R    DR3 protein
312 C F D D F A D L V P F D S W E P L M R K L G L M D N E I - K V A K A E A A G H R  HLYBX88XXprotein 272 E Q K V Q L L R N W H Q L H G K K E A - Y D T L I K D L K K A N L C T L A E K I  h Fas protein
398 E A Q Y S M L A T W R R R T P R R E A T L E L L G R V L R D M D L L G C L E D I  h TNFR I Protein
373 D Q Q Y E M L K R W R Q Q P - - A G L G A V Y A A L E R M G L D G C V E D L     DR3 protein
351 D T L Y T M L I K W V N K T G R - D A S V H T L D A L E T L G E R L A K Q K I    HLYBX88XXprotein 311 Q T I I L K D I T S D S E N S N F R N E I Q S L V                              h Fas protein
438 E E A L - - - - - - C G P A A L P P A P S L L R                                h TNFR I Protein
410 - - - - - - - - - - - - R S R L Q R G P                                        DR3 protein
390 E D H L L S S G K F M Y L E G N - - A D S A M S                               HLYBX88XXprotein
```

FIG.2C

HAPBU13R
     1 AATTCGGCAC AGCTCTTCAG GAAGTCAGAC CTTCCCTGGT TTACCTTTTT
    51 TCTGGAAAAA GCCCAACTGG GACTCCAGTC AGTAGGAAAG TGCCACAATT
   101 GTCACATGAC CGGTACTGGA AGAAACTCTC CCATCCAACA TCACCCAGTG
   151 GNATGGAAC ACTGATGAAC TTTTCACTGC ACTTGGCATT ATTTTTGTNA
   201 AGCTGAATGT GATAATAAGG GCACTGATGG AAATGTCTGG ATCATTCCGG
   251 TTGTGCGTAC TTTGAGATTT GNGTTTGGGG ATGTNCATTG TGTTTGACAG
   301 CACTTTTTTN ATCCCTAATG TNAAATGCNT NATTTGATTG TGANTTGGGG
   351 GTNAACATTG GTNAAGGNTN CCCNTNTGAC ACAGTAGNTG GTNCCCGACT
   401 TANAATNGNN GAANANGATG NATNANGAAC CTTTTTTTGG GTGGGGGGGT
   451 NNCGGGGCAG TNNAANGNNG NCTCCCCAGG TTTGGNGTNG CAATNGNGGA
   501 ANNNTGG

HSBBU76R
     1 TTTTTTTTGT AGATGGATCT TACAATGTAG CCCAAATAAA TAAATAAAGC
    51 ATTTACATTA GGATAAAAAA GTGCTGTGAA AACAATGACA TCCCAAACCA
   101 AATCTCAAAG TACGCACAAA CGGAATGATC CAGACATTTC CATAGNGTCC
   151 TTATTATCAC ATTCAGCTTA TAAAANTAAT GCCAAGTGCA GTGAAAAGTT
   201 ACAGGATGTT CCATCCACTG GGTGGATT

FIG.4

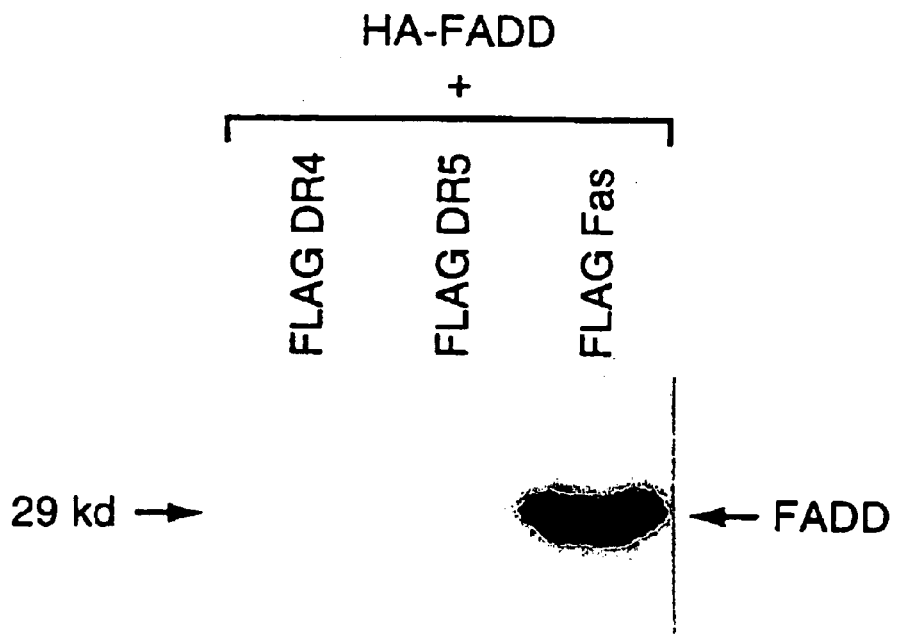
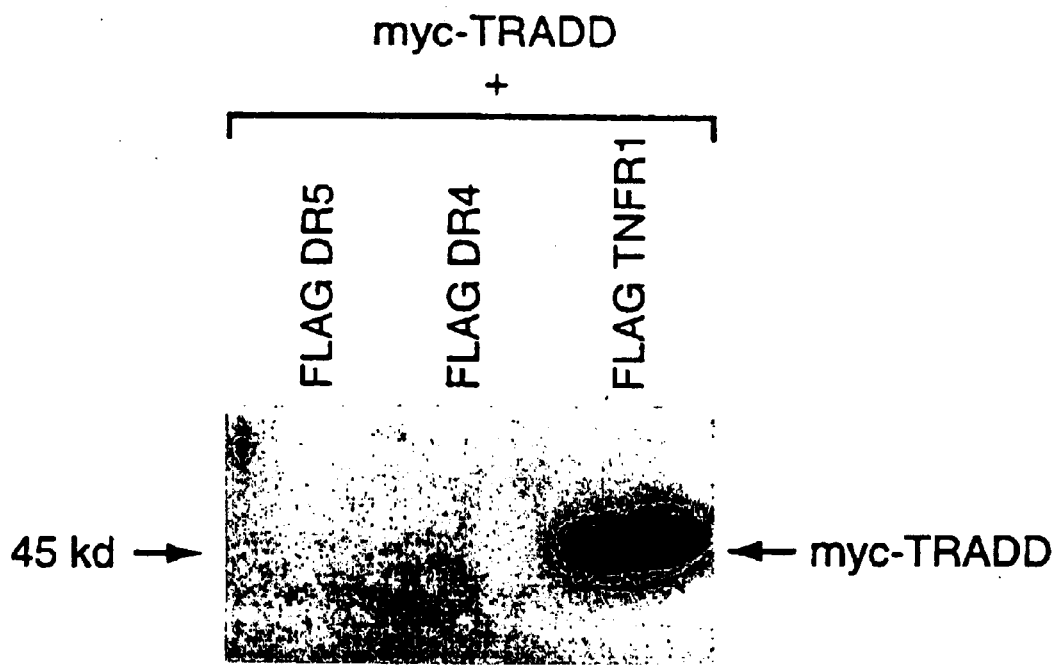
FIG.5D

DEATH DOMAIN CONTAINING RECEPTOR 5

CROSS-REFERENCE TO RELATED APPLICATIONS

The present application is a continuation of U.S. application Ser. No. 09/565,009, filed May 4, 2000, which is incorporated herein by reference; said Ser. No. 09/565,009 claims benefit to the filing dates of U.S. Provisional Application No. 60/148,939, filed Aug. 13 1999, U.S. Provisional Application No. 60/133,238, filed May 7, 1999, and U.S. Provisional Application No. 60/132,498, filed May 4, 1999; and is a continuation-in-part of U.S. application Ser. No. 09/042,583, filed Mar. 17, 1998, each of which is herein incorporated by reference; said Ser. No. 09/042,583 claims priority to U.S. Provisional application Ser. No. 60/054,021, filed Jul. 29, 1997, and U.S. Provisional Application No. 60/040,846, filed Mar. 17, 1997, each of which is herein incorporated by reference.

BACKGROUND OF THE INVENTION

1. Field of the Invention

The present invention relates to a novel member of the tumor necrosis factor family of receptors. More specifically, isolated nucleic acid molecules are provided encoding human Death Domain Containing Receptor 5, or simply "DR5." DR5 polypeptides are also provided, as are vectors, host cells. and recombinant methods for producing the same. The invention further relates to screening methods for identifying agonists and antagonists of DR5 activity.

2. Related Art

Numerous biological actions, for instance, response to certain stimuli and natural biological processes, are controlled by factors, such as cytokines Many cytokines act through receptors by engaging the receptor and producing an intra-cellular response.

For example, tumor necrosis factors (TNF) alpha and beta are cytokines, which act through TNF receptors to regulate numerous biological processes, including protection against infection and induction of shock and inflammatory disease. The TNF molecules belong to the "TNF-ligand" superfamily, and act together with their receptors or counter-ligands, the "TNF-receptor" superfamily. So far, nine members of the TNF ligand superfamily have been identified and ten members of the TNF-receptor superfamily have been characterized.

Among the ligands, there are included TNF-α, lymphotoxin-α (LT-α, also known as TNF-β), LT-β (found in complex heterotrimer LT-α2-β), FasL, CD40L, CD27L, CD30L, 4-1BBL, OX40L and nerve growth factor (NGF). The superfamily of TNF receptors includes the p55TNF receptor, p75TNF receptor, TNF receptor-related protein, FAS antigen or APO-1, CD40, CD27, CD30, 4-1BB, OX40, low affinity p75 and NGF-receptor (Meager, A., *Biologicals*, 22:291–295 (1994)).

Many members of the TNF-ligand superfamily are expressed by activated T-cells, implying that they are necessary for T-cell interactions with other cell types which underlie cell ontogeny and functions. (Meager, A., supra).

Considerable insight into the essential functions of several members of the TNF receptor family has been gained from the identification and creation of mutants that abolish the expression of these proteins. For example, naturally occurring mutations in the FAS antigen and its ligand cause lymphoproliferative disease (Watanabe-Fukunaga, R., et al., *Nature* 356:314 (1992)), perhaps reflecting a failure of programmed cell death. Mutations of the CD40 ligand cause an X-linked immunodeficiency state characterized by high levels of immunoglobulin M and low levels of immunoglobulin G in plasma, indicating faulty T-cell-dependent B-cell activation (Allen, R. C. et al., *Science* 259:990 (1993)). Targeted mutations of the low affinity nerve growth factor receptor cause a disorder characterized by faulty sensory innovation of peripheral structures (Lee, K. F. et al., *Cell* 69:737 (1992)).

TNF and LT-α are capable of binding to two TNF receptors (the 55- and 75-kd TNF receptors). A large number of biological effects elicited by TNF and LT-α, acting through their receptors, include hemorrhagic necrosis of transplanted tumors, cytotoxicity, a role in endotoxic shock, inflammation, immunoregulation, proliferation and anti-viral responses, as well as protection against the deleterious effects of ionizing radiation. TNF and LT-α are involved in the pathogenesis of a wide range of diseases, including endotoxic shock, cerebral malaria, tumors, autoimmune disease, AIDS and graft-host rejection (Beutler, B. and Von Huffel, C., *Science* 264:667–668 (1994)). Mutations in the p55 Receptor cause increased susceptibility to microbial infection.

Moreover, an about 80 amino acid domain near the C-terminus of TNFR-1 (p55) and Fas was reported as the "death domain," which is responsible for transducing signals for programmed cell death (Tartaglia et al., *Cell* 74:845 (1993)).

Apoptosis, or programmed cell death, is a physiologic process essential for the normal development and homeostasis of multicellular organisms (H. Steller, *Science* 267:1445–1449 (1995)). Derangements of apoptosis contribute to the pathogenesis of several human diseases including cancer, neurodegenerative disorders, and acquired immune deficiency syndrome (C. B. Thompson, *Science* 267:1456–1462 (1995)). Recently, much attention has focused on the signal transduction and biological function of two cell surface death receptors, Fas/APO-1 and TNFR-1 (J. L. Cleveland et al., *Cell* 81:479–482(1995); A. Fraser, et al., *Cell* 85:781–784 (1996); S. Nagata et al., *Science* 267:1449–56 (1995)). Both are members of the TNF receptor family which also include TNFR-2. low affinity NGFR, CD40, and CD30, among others (C. A. Smith et al., *Science* 248:1019–23 (1990); M. Tewari et al., in *Modular Texts in Molecular and Cell Biology* M. Purton, Heldin, Carl, Ed. (Chapman and Hall, London, 1995). While family members are defined by the presence of cysteine-rich repeats in their extracellular domains, Fas/APO-1 and TNFR-1 also share a region of intracellular homology, appropriately designated the "death domain", which is distantly related to the Drosophila suicide gene, reaper (P. Golstein, et al., *Cell* 81:185–186 (1995); K. White et al., *Science* 264:677–83 (1994)). This shared death domain suggests that both receptors interact with a related set of signal transducing molecules that, until recently, remained unidentified. Activation of Fas/APO-1 recruits the death domain-containing adapter molecule FADD/MORT1 (A.M. Chinnaiyan et al., *Cell* 81: 505–12 (1995); M. P. Boldin et al., *J. Biol Chem* 270:7795–8 (1995); F. C. Kischkel et al., *EMBO* 14:5579–5588 (1995)), which in turn binds and presumably activates FLICE/MACH1, a member of the ICE/CED-3 family of pro-apoptotic proteases (M. Muzio et al., *Cell* 85:817–827 (1996); M. P. Boldin et al., *Cell* 85:803–815 (1996)). While the central role of Fas/APO-1 is to trigger cell death, TNFR-1 can signal an array of diverse biological activities-many of which stem from its ability to activate NF-kB (L.

A. Tartaglia et al, *Immunol Today* 13:151–3 (1992)). Accordingly, TNFR-1 recruits the multivalent adapter molecule TRADD, which like FADD, also contains a death domain (H. Hsu et al., *Cell* 81:495–504 (1995); H. Hsu, et al., *Cell* 84:299–308 (1996)). Through its associations with a number of signaling molecules including FADD, TRAF2, and RIP, TRADD can signal both apoptosis and NF-kB activation (H. Hsu et al., *Cell* 84:299–308 (1996); H. Hsu, et al, *Immunity* 4:387–396 (1996)).

Recently, a new apoptosis-inducing TNF ligand has been discovered. S. R. Wiley et al. (*Immunity* 3:673–682 (1995)) named the molecule—"TNF-related apoptosis-inducing ligand" or simply "TRAIL." The molecule was also called "Apo-2 ligand" or "Apo-2L." R. M. Pitt et al, *J. Biol. Chem.* 271:12687–12690 (1996). For convenience, the molecule will be referred to herein as TRAIL.

Unlike FAS ligand, whose transcripts appear to be largely restricted to stimulated T-cells, significant levels of TRAIL are detected in many human tissues (e.g., spleen, lung, prostate, thymus, ovary, small intestine, colon, peripheral blood lymphocytes, placenta, kidney), and is constitutively transcribed by some cell lines. It has been shown that TRAIL acts independently from the Fas ligand (Wiley et al., supra). It has also been shown that TRAIL activates apoptosis rapidly, within a time frame that is similar to death signaling by Fas/Apo-1L, but much faster than TNF-induced apoptosis. S. A. Marsters et al., *Current Biology* 6:750–752 (1996). The inability of TRAIL to bind TNFR-1, Fas, or the recently identified DR3, suggests that TRAIL may interact with a unique receptor(s).

The effects of TNF family ligands and TNF family receptors are varied and influence numerous functions, both normal and abnormal, in the biological processes of the mammalian system. There is a clear need, therefore, for identification and characterization of such receptors and ligands that influence biological activity, both normally and in disease states. In particular, there is a need to isolate and characterize additional novel receptors that bind TRAIL.

SUMMARY OF THE INVENTION

The present invention provides for isolated nucleic acid molecules comprising, or alternatively consisting of, nucleic acid sequences encoding the amino acid sequence shown in FIGS. 1A–B (SEQ ID NO:2) or the amino acid sequence encoded by the cDNA deposited as ATCC Deposit No. 97920 on Mar. 7, 1997.

The present invention also provides recombinant vectors, which include the isolated nucleic acid molecules of the invention, and to host cells containing the recombinant vectors, as well as to methods of making such vectors and host cells and for using them for production of DR5 polypeptides or peptides by recombinant techniques.

The invention further provides an isolated DR5 polypeptide having an amino acid sequence encoded by a polynucleotide described herein.

The present invention also provides diagnostic assays such as quantitative and diagnostic assays for detecting levels of DR5 protein. Thus, for instance, a diagnostic assay in accordance with the invention for detecting overexpression of DR5, or soluble form thereof, compared to normal control tissue samples may be used to detect the presence of tumors.

Tumor Necrosis Factor (TNF) family ligands are known to be among the most pleiotropic cytokines, inducing a large number of cellular responses, including cytotoxicity, antiviral activity, immunoregulatory activities, and the transcriptional regulation of several genes. Cellular response to TNF-family ligands include not only normal physiological responses, but also diseases associated with increased apoptosis or the inhibition of apoptosis. Apoptosis—programmed cell death—is a physiological mechanism involved in the deletion of peripheral T lymphocytes of the immune system, and its dysregulation can lead to a number of different pathogenic processes. Diseases associated with increased cell survival, or the inhibition of apoptosis, include cancers, autoimmune disorders, viral infections, inflammation, graft versus host disease, acute graft rejection, and chronic graft rejection. Diseases associated with increased apoptosis include AIDS, neurodegenerative disorders, myelodysplastic syndromes, ischemic injury, toxin-induced liver disease, septic shock, cachexia and anorexia.

Thus, the invention further provides a method for enhancing apoptosis induced by a TNF-family ligand, which involves administering to a cell which expresses the DR5 polypeptide an effective amount of an agonist capable of increasing DR5 mediated signaling. Preferably, DR5 mediated signaling is increased to treat and/or prevent a disease wherein decreased apoptosis is exhibited.

In a further aspect, the present invention is directed to a method for inhibiting apoptosis induced by a TNF-family ligand, which involves administering to a cell which expresses the DR5 polypeptide an effective amount of an antagonist capable of decreasing DR5 mediated signaling. Preferably, DR5 mediated signaling is decreased to treat and/or prevent a disease wherein increased apoptosis is exhibited.

Whether any candidate "agonist" or "antagonist" of the present invention can enhance or inhibit apoptosis can be determined using art-known TNF-family ligand/receptor cellular response assays, including those described in more detail below. Thus, in a further aspect, a screening method is provided for determining whether a candidate agonist or antagonist is capable of enhancing or inhibiting a cellular response to a TNF-family ligand. The method involves contacting cells which express the DR5 polypeptide with a candidate compound and a TNF-family ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By the invention, a cell expressing the DR5 polypeptide can be contacted with either an endogenous or exogenously administered TNF-family ligand.

BRIEF DESCRIPTION OF THE FIGURES

FIGS. 1A–B shows the nucleotide (SEQ ID NO:1) and deduced amino acid sequence (SEQ ID NO:2) of DR5. It is predicted that amino acids from about 1 to about 51 (underlined) constitute the signal peptide (amino acid residues from about −51 to about −1 in SEQ ID NO:2); amino acids from about 52 to about 184 constitute the extracellular domain (amino acid residues from about 1 to about 133 in SEQ ID NO:2); amino acids from about 84 to about 179 constitute the cysteine rich domain (amino acid residues from about 33 to 128 in SEQ ID NO:2); amino acids from about 185 to about 208 (underlined) constitute the transmembrane domain (amino acid residues from about 134 to about 157 in SEQ ID NO:2); and amino acids from about 209 to about 411 constitute the intracellular domain (amino acid residues from about 158 to about 360 in SEQ ID NO:2), of which amino acids from about 324 to about 391 (italicized) constitute the death domain (amino acid residues from about 273 to about 340 in SEQ ID NO:2).

FIGS. 2A–C shows the regions of similarity between the amino acid sequences of DR5 (HLYBX88), human tumor necrosis factor receptor 1 (h TNFR-1) (SEQ ID NO:3), human Fas protein (SEQ ID NO:4), and the death domain containing receptor 3 (SEQ ID NO:5). The comparison was created with the Megalign program which is contained in the DNA Star suite of programs, using the Clustal method. Residues that match the consensus are shaded.

FIG. 4 shows the nucleotide sequences (HAPBU13R and HSBBU76R) of two cDNA molecules which are related to the nucleotide sequence shown in FIGS. 1A–B (SEQ ID NO:1).

FIG. 5D is an immunoblot showing that, like DR4, DR5 did not interact with FADD and TRADD in vivo.

DETAILED DESCRIPTION OF THE PREFERRED EMBODIMENTS

Figure 2A:
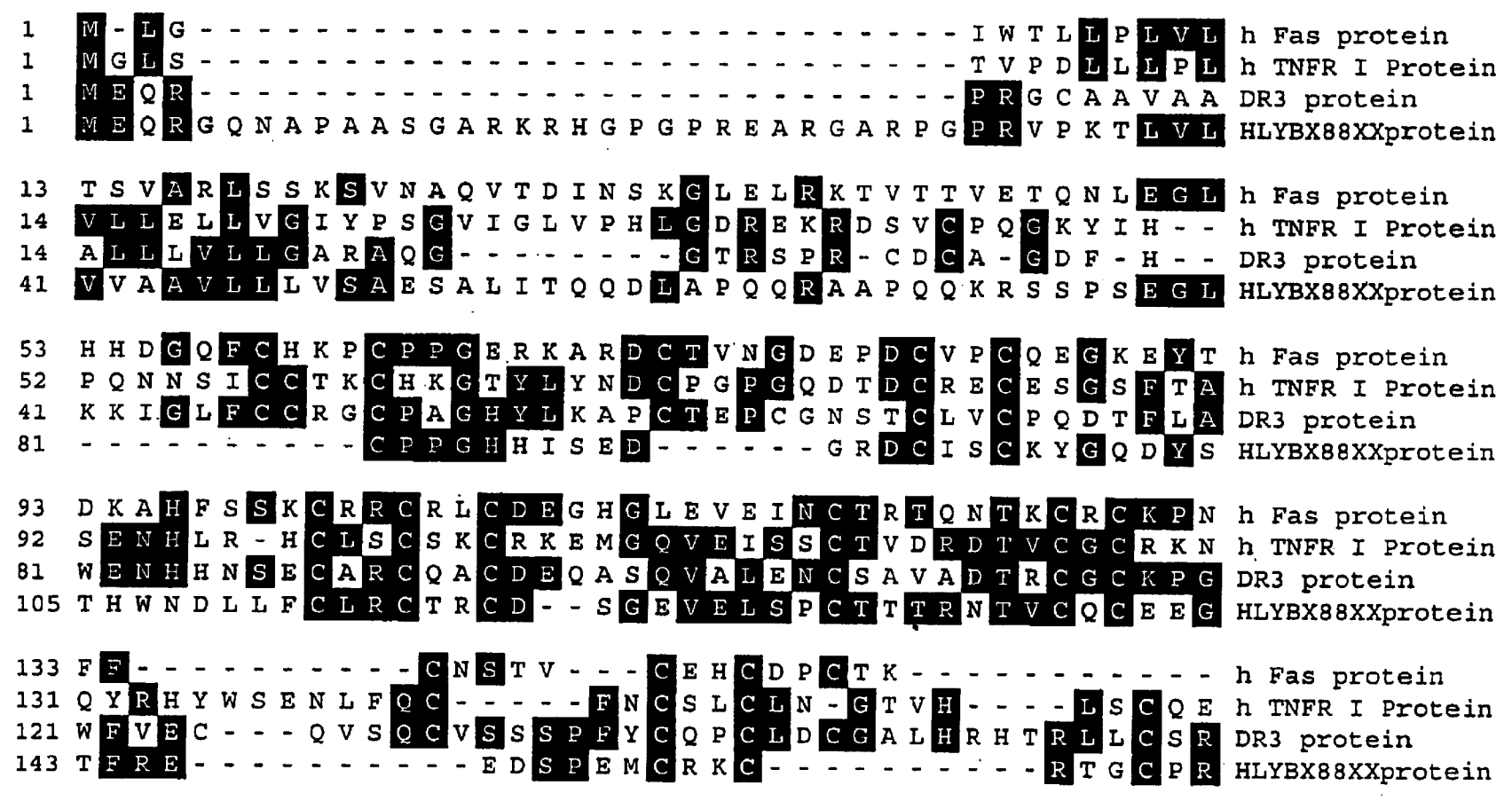
Figure 2B:
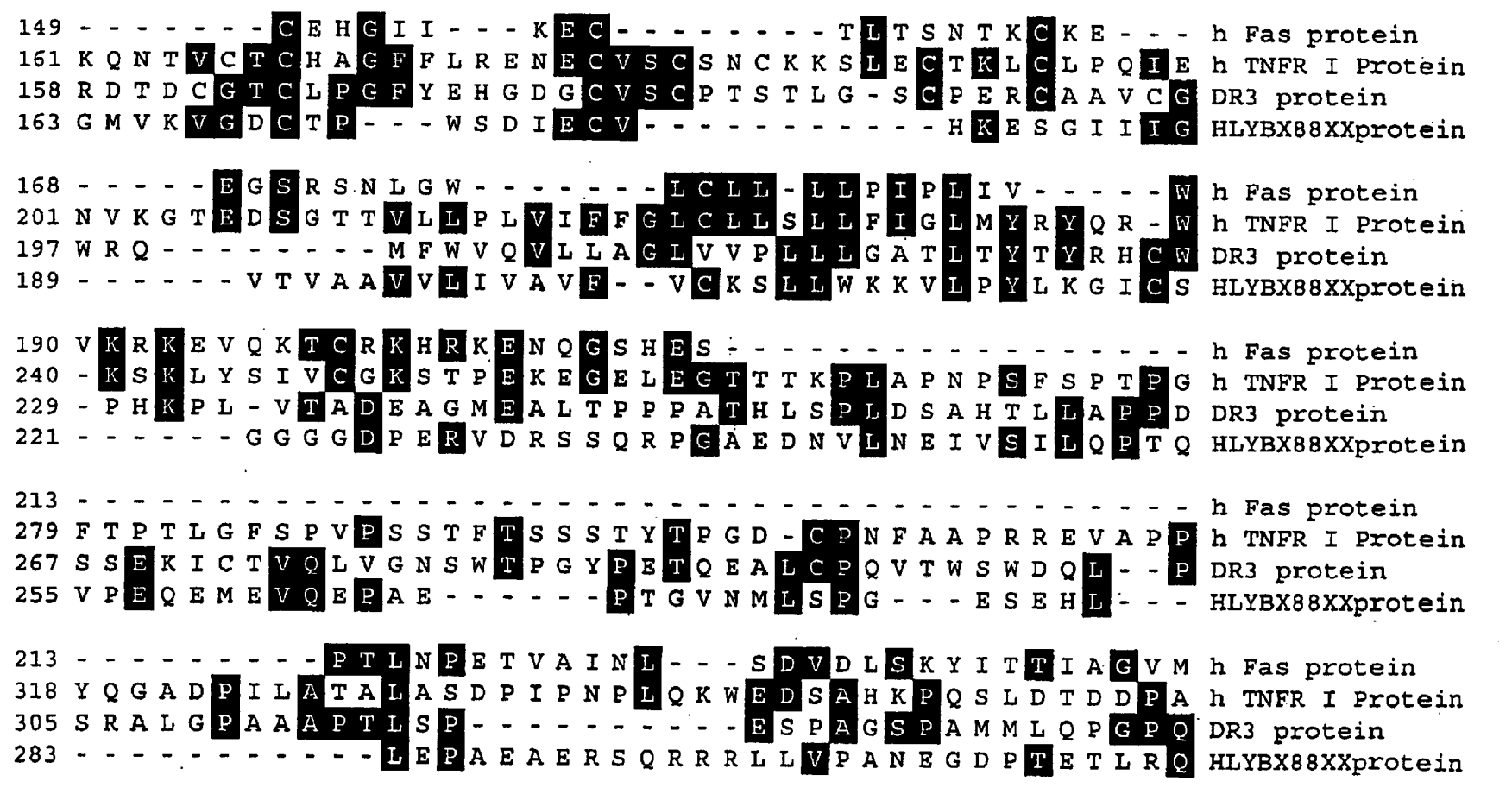
Figure 3:
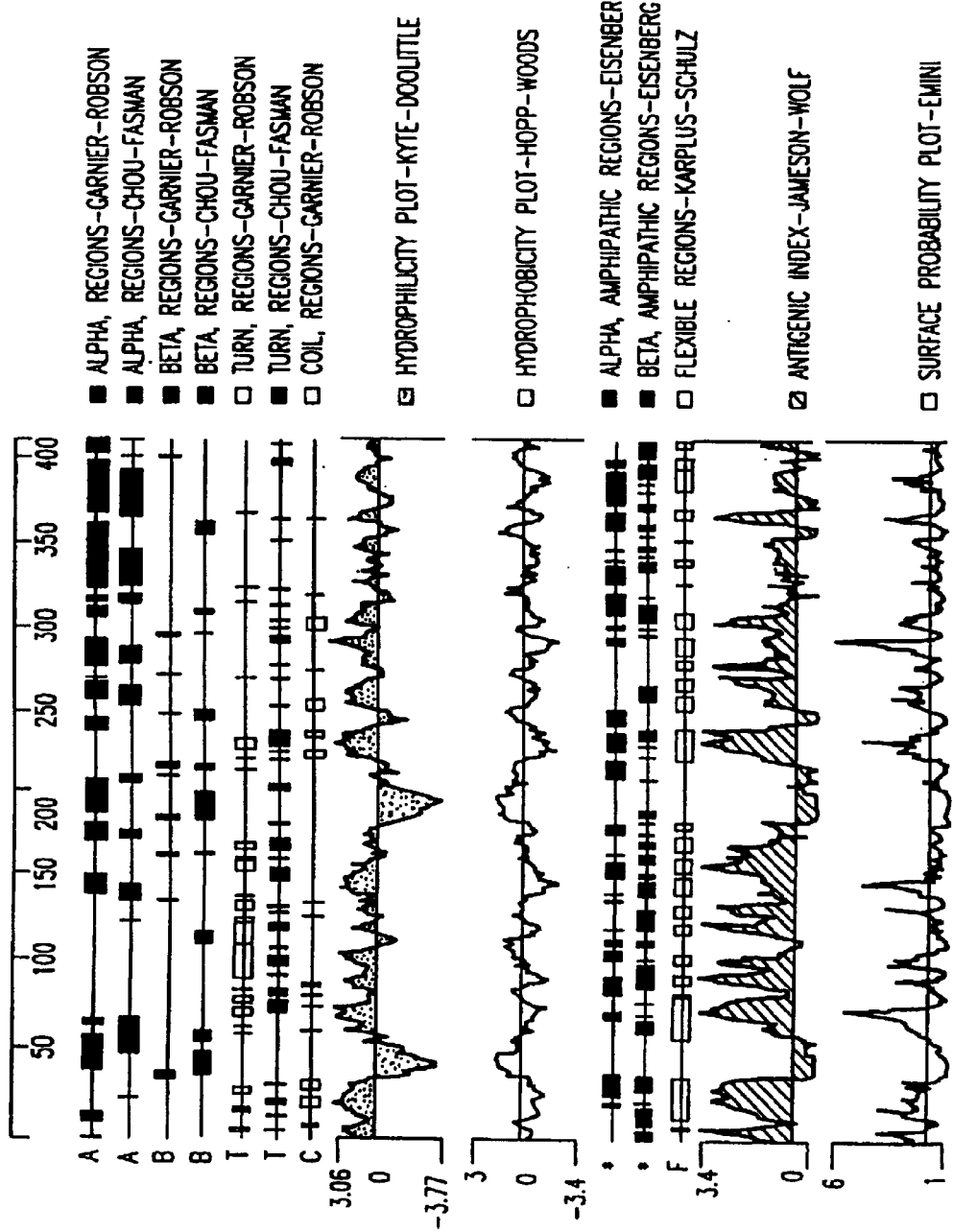
FIG. 3 shows an analysis of the DR5 amino acid sequence. Alpha, beta, turn and coil regions; hydrophilicity and hydrophobicity; amphipathic regions; flexible regions; antigenic index and surface probability are shown, as predicted for the amino acid sequence depicted in FIG. 1 using the default parameters of the recited computer program. In the "Antigenic Index-Jameson-Wolf" graph, amino acid residues about 62 to about 110, about 119 to about 164, about 224 to about 271, and about 275 to about 370 as depicted in FIGS. 1A–B correspond to the shown highly antigenic regions of the DR5 protein. These highly antigenic fragments in FIGS. 1A–B correspond to the following fragments, respectively, in SEQ ID NO:2: amino acid residues from about 11 to about 59, from about 68 to about 113, from about 173 to about 220, and from about 224 to about 319.

The present invention provides isolated nucleic acid molecules comprising, or alternatively consisting of, a polynucleotide encoding a DR5 polypeptide having the amino acid sequence shown in FIGS. 1A–B (SEQ ID NO:2), or a fragment of this polypeptide. The DR5 polypeptide of the present invention shares sequence homology with other known death domain containing receptors of the TNFR family including human TNFR-1, DR3 and Fas (FIGS. 2A–C). The nucleotide sequence shown in FIGS. 1A–B (SEQ ID NO:1) was obtained by sequencing cDNA clones such as HLYBX88, which was deposited on Mar. 7, 1997 at the American Type Culture, 10801 University Boulevard, Manassas, Va., 20110-2209, and given Accession Number 97920. The deposited cDNA is contained in the pSport 1 plasmid (Life Technologies, Gaithersburg, Md.).

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleic acid sequence set out in SEQ ID NO:1, a nucleic acid molecule of the present invention encoding a DR5 polypeptide may be obtained using standard cloning and screening procedures, such as those for cloning cDNAs using mRNA as starting material. Illustrative of the invention, the nucleic acid molecule of the invention has been identified in cDNA libraries of the following tissues: primary dendritic cells, endothelial tissue, spleen, chronic lymphocytic leukemia, and human thymus stromal cells.

The determined nucleotide sequence of the DR5 cDNA of SEQ ID NO:1 contains an open reading frame encoding a protein of about 411 amino acid residues whose initiation codon is at position 130–132 of the nucleotide sequence shown in FIGS. 1A–B (SEQ ID NO.1), with a leader sequence of about 51 amino acid residues. Of known members of the TNF receptor family, the DR5 polypeptide of the invention shares the greatest degree of homology with human TNFR-1, FAS and DR3 polypeptides shown in FIGS. 2A–C, including significant sequence homology over multiple cysteine-rich domains. The homology DR5 shows to other death domain containing receptors strongly indicates that DR5 is also a death domain containing receptor with the ability to induce apoptosis. DR5 has also now been shown to bind TRAIL.

As indicated, the present invention also provides the mature form(s) of the DR5 protein of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide.

Therefore, the present invention provides a nucleotide sequence encoding the mature DR5 polypeptide having the amino acid sequence encoded by the cDNA contained in the plasmid identified as ATCC Deposit No. 97920, and as shown in FIGS. 1A–B (SEQ ID NO:2). By the mature DR5 protein having the amino acid sequence encoded by the cDNA contained in the plasmid identified as ATCC Deposit No. 97920, is meant the mature form(s) of the DR5 protein produced by expression in a mammalian cell (e.g., COS cells, as described below) of the complete open reading frame encoded by the human cDNA contained in the deposited plasmid. As indicated below, the mature DR5 having the amino acid sequence encoded by the cDNA contained in ATCC Deposit No. 97920, may or may not differ from the predicted "mature" DR5 protein shown in SEQ ID NO:2 (amino acids from about 1 to about 360) depending on the accuracy of the predicted cleavage site based on computer analysis.

Methods for predicting whether a protein has a secretory leader as well as the cleavage point for that leader sequence are available. For instance, the method of McGeoch (*Virus Res.* 3:271–286 (1985)) and von Heinje (*Nucleic Acids Res.* 14:4683–4690 (1986)) can be used. The accuracy of predicting the cleavage points of known mammalian secretory proteins for each of these methods is in the range of 75–80%. von Heinje, supra. However, the two methods do not always produce the same predicted cleavage point(s) for a given protein.

In the present case, the predicted amino acid sequence of the complete DR5 polypeptide of the present invention was analyzed by a computer program ("PSORT"). See, K. Nakai and M. Kanebisa, *Genomics* 14:897–911(1992). PSORT is an expert system for predicting the cellular location of a protein based on the amino acid sequence. As part of this computational prediction of localization, the methods of McGeoch and von Heinje are incorporated. The analysis by the PSORT program predicted the cleavage sites between amino acids 51 and 52 in FIGS. 1A–B (−1 and 1 in SEQ ID NO:2). Thereafter, the complete amino acid sequences were further analyzed by visual inspection, applying a simple form of the (−1,−3) rule of von Heinje. von Heinje, supra. Thus, the leader sequence for the DR5 protein is predicted to consist of amino acid residues from about 1 to about 51, underlined in FIGS. 1A–B (corresponding to amino acid residues about −51 to about 1 in SEQ ID NO:2), while the predicted mature DR5 protein consists of residues from about 52 to about 411 in FIGS. 1A–B (corresponding to amino acid residues about 1 to about 360 in SEQ ID NO:2).

As one of ordinary skill would appreciate, due to the possibility of sequencing errors, as well as the variability of cleavage sites for leaders in different known proteins, the predicted DR5 receptor polypeptide encoded by the deposited cDNA comprises about 411 amino acids, but may be anywhere in the range of 401–421 amino acids; and the predicted leader sequence of this protein is about 51 amino acids, but may be anywhere in the range of about 41 to about 61 amino acids. It will further be appreciated that, the domains described herein have been predicted by computer analysis, and accordingly, that depending on the analytical criteria used for identifying various functional domains, the exact "address" of, for example, the extracelluar domain, intracellular domain, death domain, cysteine-rich motifs, and transmembrane domain of DR5 may differ slightly. For example, the exact location of the DR5 extracellular domain in FIGS. 1A–B (SEQ ID NO:2) may vary slightly (e.g., the address may "shift" by about 1 to about 20 residues, more likely about 1 to about 5 residues) depending on the criteria used to define the domain. In any event, as discussed further below, the invention further provides polypeptides having various residues deleted from the N-terminus and/or C-terminus of the complete DR5, including polypeptides lacking one or more amino acids from the N-termini of the extracellular domain described herein, which constitute soluble forms of the extracellular domain of the DR5 polypeptides.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution.

However, a nucleic acid molecule contained in a clone that is a member of a mixed clone library (e.g., a genomic or cDNA library) and that has not been isolated from other clones of the library (e.g., in the form of a homogeneous solution containing the clone without other members of the library) or a chromosome isolated or removed from a cell or a cell lysate (e.g., a "chromosome spread", as in a karyotype), is not "isolated" for the purposes of this invention. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DR5 DNA molecules comprising, or alternatively consisting of, an open reading frame (ORF) shown in SEQ ID NO:1; DNA molecules comprising, or alternatively consisting of, the coding sequence for the mature DR5 protein; and DNA molecules which comprise, or alternatively consist of, a sequence substantially different from those described above, but which, due to the degeneracy of the genetic code, still encode the DR5 protein. Of course, the genetic code is well known in the art. Thus, it would be routine for one skilled in the art to generate such degenerate variants.

In addition, the invention provides nucleic acid molecules having nucleotide sequences related to extensive portions of SEQ ID NO:1 which have been determined from the following related cDNAs: HAPBU13R (SEQ ID NO:6) and HSBBU76R (SEQ ID NO:7). The nucleotide sequences of HAPBU13R and HSBBU76R are shown in FIG. 4.

The nucleotide sequence of an additional related polynucleotide which has been assigned GenBank Accession number Z66083 is shown in SEQ ID NO:14.

In another aspect, the invention provides isolated nucleic acid molecules encoding the DR5 polypeptide having an amino acid sequence encoded by the cDNA contained in the plasmid deposited as ATCC Deposit No. 97920 on Mar. 7, 1997. In a further embodiment, nucleic acid molecules are provided that encode the mature DR5 polypeptide or the full length DR5 polypeptide lacking the N-terminal methionine. The invention further provides an isolated nucleic acid molecule having the nucleotide sequence shown in SEQ ID NO:1 or the nucleotide sequence of the DR5 cDNA contained in the above-described deposited plasmid, or a nucleic acid molecule having a sequence complementary to one of the above sequences. Such isolated molecules, particularly DNA molecules, have uses which include, but are not limited to, as probes for gene mapping by in situ hybridization with chromosomes, and for detecting expression of the DR5 gene in human tissue, for instance, by Northern blot analysis.

The present invention is further directed to fragments of the isolated nucleic acid molecules described herein. By fragments of an isolated DNA molecule having the nucleotide sequence shown in SEQ ID NO:1 or having the nucleotide sequence of the deposited cDNA (the cDNA contained in the plasmid deposited as ATCC Deposit No. 97920) are intended DNA fragments at least 20 nt, and more preferably at least 30 nt in length, and even more preferably, at least about 40, 50, 100, 150, 200, 250, 300, 350, 400, 450, 500, 550, 600, 650, 700, 750, 800, 850, 900, 950, 1000, 1050, 1100, 1150, or 1200 nucleotides in length, which are useful as DNA probes as discussed above. Of course, DNA fragments corresponding to most, if not all, of the nucleotide sequence shown in SEQ ID NO:1 are also useful as DNA probes. By a fragment at least about 20 nt in length, for example, is intended fragments which include 20 or more contiguous bases from the nucleotide sequence of the deposited DNA or the nucleotide sequence as shown in SEQ ID NO:1. In this context "about" includes the particularly recited size, larger or smaller by several (5, 4, 3, 2, or 1) nucleotides, at either terminus or at both termini.

Representative examples of DR5 polynucleotide fragments of the invention include, for example, fragments that comprise, or alternatively consist of, a sequence from about nucleotide 1–130, 130–180, 181–231, 232–282, 283–333, 334–384, 385–435, 436–486, 487–537, 538–588, 589–639, 640–681, 682–732, 733–753, 754–804, 805–855, 856–906, 907–957, 958–1008, 1009–1059, 1060–1098, 1099–1149, 1150–1200, 1201–1251, 1252–1302, 1303–1353, 1354–1362, and 1363 to the end of SEQ ID NO:1, or the complementary DNA strand thereto, or the cDNA contained in the deposited plasmid. In this context "about" includes the particularly recited ranges, larger or smaller by several (5, 4, 3, 2, or 1) nucleotides, at either terminus or at both termini. Polypeptides encoded by these polynucleotides are also encompassed by the invention.

The present invention is further directed to polynucleotides comprising, or alternatively consisting of, isolated nucleic acid molecules which encode domains of DR5. In one aspect, the invention provides polynucleotides comprising, or alternatively consisting of, nucleic acid molecules which encode beta-sheet regions of DR5 protein set out in Table I. Representative examples of such polynucleotides include nucleic acid molecules which encode a polypeptide comprising, or alternatively consisting of, one, two, three, four, five, or more amino acid sequences selected from the group consisting of: amino acid residues from about −16 to about −2, amino acid residues from about 2 to about 9, amino acid residues from about 60 to about 67, amino acid residues from about 135 to about 151, amino acid residues from about 193 to about 199, and amino acid residues from about 302 to about 310 in SEQ ID NO:2. In this context "about" includes the particularly recited value and values larger or smaller by several (5, 4, 3, 2, or 1) amino acid residues. Polypeptides encoded by these polynucleotides are also encompassed by the invention.

In specific embodiments, the polynucleotide fragments of the invention encode a polypeptide which demonstrates a DR5 functional activity. By a polypeptide demonstrating a DR5 "functional activity" is meant, a polypeptide capable of displaying one or more known functional activities associated with a complete (full-length) or mature DR5 polypeptide, as well as secreted forms of DR5. Such functional activities include, but are not limited to, biological activity (e.g., ability to induce apoptosis in cells expressing the polypeptide (see e.g., Example 5)), antigenicity (ability to bind (or compete with a DR5 polypeptide for binding) to an anti-DR5 antibody), immunogenicity (ability to generate antibody which binds to a DR5 polypeptide), ability to form multimers, and ability to bind to a receptor or ligand and for a DR5 polypeptide (e.g., TRAIL; Wiley et al, *Immunity* 3, 673–682 (1995))

The functional activity of DR5 polypeptides, and fragments, variants derivatives, and analogs thereof, can be assayed by various methods.

For example, in one embodiment where one is assaying for the ability to bind or compete with full-length (complete) DR5 polypeptide for binding to anti-DR5 antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays. and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a DR5 ligand is identified (e.g. TRAIL), or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, et al., *Microbiol. Rev.* 59:94–123 (1995). In another embodiment, physiological correlates of DR5 binding to its substrates (signal transduction) can be assayed.

In addition, assays described herein (see Examples 5 and 6), and otherwise known in the art may routinely be applied to measure the ability of DR5 polypeptides and fragments, variants derivatives and analogs thereof to elicit DR5 related biological activity (e.g., ability to induce apoptosis in cells expressing the polypeptide (see e.g., Example 5), and the ability to bind a ligand, e.g., TRAIL (see, e.g., Example 6) in vitro or in vivo). For example, biological activity can routinely be measured using the cell death assays performed essentially as previously described (Chinnaiyan et al., *Cell* 81:505–512 (1995); Boldin et al.,*J. Biol. Chem.* 270:7795–8 (1995); Kischkel et al., *EMBO* 14:5579–5588 (1995); Chinnaiyan et al., *J. Biol. Chem.* 271–4961–4965 (1996)) and as set forth in Example 5 below. In one embodiment involving MCF7 cells, plasmids encoding full-length DR5 or a candidate death domain containing receptor are co-transfected with the pLantern reporter construct encoding green fluorescent protein. Nuclei of cells transfected with DR5 will exhibit apoptotic morphology as assessed by DAPI staining.

Other methods will be known to the skilled artisan and are within the scope of the invention.

Preferred nucleic acid fragments of the present invention include, but are not limited to, a nucleic acid molecule encoding a polypeptide comprising, or alternatively consisting of, one, two, three, four, five, or more amino acid sequences selected from the group consisting of: a polypeptide comprising, or alternatively consisting of, the DR5 extracellular domain (amino acid residues from about 52 to about 184 in FIGS. 1A–B (amino acid residues from about 1 to about 133 in SEQ ID NO:2)); a polypeptide comprising, or alternatively consisting of, the DR5 transmembrane domain (amino acid residues from about 185 to about 208 in FIGS. 1A–B (amino acid residues from about 134 to about 157 in SEQ TD NO:2)); a polypeptide comprising, or alternatively consisting of, the cysteine rich domain of DR5 (amino acid residues from about 84 to about 179 in FIGS. 1A–B (from about 33 to about 128 in SEQ ID NO:2)); a polypeptide comprising, or alternatively consisting of, the DR5 intracellular domain (amino acid residues from about 209 to about 411 in FIGS. 1A–B (amino acid residues from about 158 to about 360 in SEQ II) NO:2)); a polypeptide comprising, or alternatively consisting of, a fragment of the predicted mature DR5 polypeptide, wherein the fragment has a DR5 functional activity (e.g., antigenic activity or biological activity); a polypeptide comprising, or alternatively consisting of, the DR5 receptor extracellular and intracellular domains with all or part of the transmembrane domain deleted; a polypeptide comprising, or alternatively consisting of, the DR5 death domain (amino acid residues from about 324 to about 391 in FIGS. 1A–B (from about 273 to about 340 in SEQ ID NO:2)); and a polypeptide comprising, or alternatively consisting of, one, two, three, four or more, epitope bearing portions of the DR5 receptor protein. In additional embodiments, the polynucleotide fragments of the invention encode a polypeptide comprising, or alternatively consisting of, any combination of 1, 2, 3, 4, 5, 6, 7, or all 8 of the above members. Since the location of these domains have been predicted by computer graphics, one of ordinary skill would appreciate that the amino acid residues constituting these domains may vary slightly (e.g., by about 1 to 15 residues) depending on the criteria used to define each domain. Polypeptides encoded by these nucleic acid molecules are also encompassed by the invention.

It is believed one or both of the extracellular cysteine rich motifs of DR5 disclosed in FIGS. 1A–B is important for interactions between DR5 and its ligands (e.g., TRAIL). Accordingly, specific embodiments of the invention are directed to polynucleotides encoding a polypeptide comprising, or alternatively consisting of, one or both amino acid sequences selected from the group consisting of: amino acid residues 84 to 131, and/or 132 to 179 of the DR5 sequence shown in FIGS. 1A–B (amino acid residues 33 to 80, and/or 81 to 128 in SEQ ID NO:2). In a specific embodiment the polynucleotides encoding DR5 polypeptides of the invention comprise, or alternatively consist of, both of the extracellular cysteine-rich motifs disclosed in FIGS. 1A–B.

In certain embodiments, polynucleotides of the invention comprise, or alternatively consist of, a polynucleotide sequence at least 80%, 85%, 90%, 92%, 95%, 96%, 97%, 98% or 99% identical to the polynucleotide sequence encoding the cysteine-rich domain described above. The present invention also encompasses the above polynucleotide sequences fused to a heterologous polynucleotide sequence. Polypeptides encoded by these polynucleotides are also encompassed by the invention. Methods to measure the percent identity of a polynucleotide sequence to a reference polynucleotide sequence are described infra.

In another embodiment, the invention provides an isolated nucleic acid molecule comprising, or alternatively consisting of, a polynucleotide which hybridizes under stringent hybridization conditions to nucleic acids complementary to the cysteine-rich domain encoding polynucleotides described above. The meaning of the phrase "stringent conditions" as used herein is described infra. Polypeptides encoded by such polynucleotides are also contemplated by the invention.

Preferred nucleic acid fragments of the invention encode a full-length DR5 polypeptide lacking the nucleotides encoding the amino-terminal methionine (nucleotides 130–132 in SEQ ID NO:1) as it is known that the methionine is cleaved naturally and such sequences maybe useful in genetically engineering DR5 expression vectors. Polypeptides encoded by such polynucleotides are also contemplated by the invention.

In additional embodiments, the polynucleotides of the invention encode functional attributes of DR5. Preferred embodiments of the invention in this regard include fragments that comprise, or alternatively consist of, one, two three, four, or more of the following functional domains: alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions alpha-amphipathic regions, beta-amphipathic regions, flexible regions surface-forming regions and high antigenic index regions of DR5.

The data representing the structural or functional attributes of DR5 set forth in FIG. 3 and/or Table I, as described above, were generated using the various identified modules and algorithms of the DNA*STAR set on default parameters. In a preferred embodiment, the data presented in columns VIII, IX. XIII, and XIV of Table I can be used to determine regions of DR5 which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 3. but may. as shown in Table I, be represented or identified by using tabular representations of the data presented in FIG. 3. The DNA*STAR computer algorithm used to generate FIG. 3 (set on the original default parameters) was used to present the data in FIG. 3 in a tabular format (See Table I). The tabular format of the data in FIG. 3 may be used to easily determine specific boundaries of a preferred region The above-mentioned preferred regions set out in FIG. 3 and in Table I include, but are not limited to, regions of the aforementioned types identified by analysis of the amino acid sequence set out in SEQ ID NO:2. As set out in FIG. 3 and in Table I, such preferred regions include Garnier-Robson alpha-regions, beta-regions, turn-regions, and coil-regions (columns I, III, V, and VII in Table I), Chou-Fasman alpha-regions, beta-regions, and turn-regions (columns II, IV, and VI in Table I), Kyte-Doolittle hydrophilic regions (column VIII in Table I), Hopp-Woods hydrophobic regions (column IX in Table I), Eisenberg alpha- and beta-amphipathic regions (columns X and XI in Table I), Karplus-Schulz flexible regions (column XII in Table I), Jameson-Wolf regions of high antigenic index (column XIII in Table I), and Emini surface-forming regions (column XIV in Table I).

TABLE I

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | A | . | . | . | . | . | . | 1.11 | -0.70 | . | * | . | 1.29 | 2.18 |
| Glu | 2 | A | . | . | . | . | . | . | 1.50 | -0.70 | . | * | . | 1.63 | 1.69 |
| Gln | 3 | A | . | . | . | . | T | . | 1.89 | -0.73 | . | * | . | 2.17 | 2.28 |
| Arg | 4 | . | . | . | . | T | T | . | 1.69 | -0.76 | . | * | . | 2.91 | 3.71 |
| Gly | 5 | . | . | . | . | T | T | . | 1.87 | -0.87 | . | * | F | 3.40 | 2.17 |
| Gln | 6 | . | . | . | . | T | T | . | 1.88 | -0.44 | . | * | F | 2.76 | 1.93 |
| Asn | 7 | . | . | . | . | . | . | C | 1.29 | -0.34 | . | * | F | 1.87 | 1.00 |
| Ala | 8 | . | . | . | . | . | . | C | 0.99 | 0.16 | . | . | F | 1.08 | 1.02 |
| Pro | 9 | . | . | . | . | . | . | C | 0.53 | 0.11 | . | * | . | 0.44 | 0.79 |
| Ala | 10 | A | . | . | . | . | . | . | 0.29 | 0.14 | . | * | . | -0.10 | 0.48 |
| Ala | 11 | A | . | . | . | . | T | . | 0.40 | 0.24 | . | . | . | 0.10 | 0.48 |
| Ser | 12 | A | . | . | . | . | T | . | 0.44 | -0.26 | . | * | F | 0.85 | 0.61 |
| Gly | 13 | A | . | . | . | . | T | . | 1.14 | -0.69 | . | * | F | 1.30 | 1.22 |
| Ala | 14 | A | . | . | . | . | T | . | 1.32 | -1.19 | . | * | F | 1.30 | 2.36 |
| Arg | 15 | A | . | . | . | T | . | . | 1.57 | -1.19 | . | * | F | 1.50 | 2.39 |
| Lys | 16 | . | . | . | . | T | . | . | 1.94 | -1.14 | . | . | F | 1.50 | 2.39 |
| Arg | 17 | . | . | . | . | T | . | . | 1.90 | -1.14 | . | * | F | 1.80 | 3.66 |
| His | 18 | . | . | . | . | . | . | C | 2.03 | -1.21 | * | * | F | 1.90 | 1.85 |
| Gly | 19 | . | . | . | . | . | T | C | 2.73 | -0.79 | * | * | F | 2.40 | 1.43 |
| Pro | 20 | . | . | . | . | . | T | C | 2.62 | -0.79 | * | * | F | 2.70 | 1.43 |
| Gly | 21 | . | . | . | . | . | T | C | 1.99 | -0.79 | * | . | F | 3.00 | 1.82 |
| Pro | 22 | . | . | . | . | . | T | C | 1.99 | -0.79 | . | * | F | 2.70 | 1.86 |
| Arg | 23 | . | A | . | . | . | . | C | 1.68 | -1.21 | * | . | F | 2.30 | 2.35 |
| Glu | 24 | . | A | B | . | . | . | . | 1.43 | -1.21 | * | . | F | 2.10 | 2.35 |
| Ala | 25 | . | A | . | . | T | . | . | 1.76 | -1.14 | * | . | F | 2.50 | 1.54 |
| Arg | 26 | . | A | . | . | T | . | . | 1.89 | -1.57 | * | . | F | 2.50 | 1.54 |
| Gly | 27 | . | . | . | . | T | . | . | 1.76 | -1.14 | * | . | F | 3.00 | 1.37 |
| Ala | 28 | . | . | . | . | T | . | C | 1.43 | -0.71 | * | * | F | 2.70 | 1.35 |
| Arg | 29 | . | . | . | . | . | T | C | 1.54 | -0.79 | * | * | F | 2.66 | 1.06 |
| Pro | 30 | . | . | . | . | . | T | C | 1.28 | -0.79 | * | * | F | 2.62 | 2.10 |
| Gly | 31 | . | . | . | . | . | T | C | 0.96 | -0.57 | * | * | F | 2.58 | 1.54 |
| Pro | 32 | . | . | . | . | . | T | C | 1.34 | -0.64 | * | * | F | 2.54 | 1.22 |
| Arg | 33 | . | . | . | . | . | . | C | 1.62 | -0.64 | * | * | F | 2.60 | 1.58 |
| Val | 34 | . | . | . | . | . | . | C | 0.70 | -0.59 | * | * | F | 2.34 | 2.30 |
| Pro | 35 | . | . | B | . | . | . | . | 0.06 | -0.33 | * | * | F | 1.58 | 1.23 |
| Lys | 36 | . | . | B | B | . | . | . | -0.41 | -0.11 | * | . | F | 0.97 | 0.46 |
| Thr | 37 | . | . | B | B | . | . | . | -1.06 | 0.57 | * | * | F | -0.19 | 0.52 |
| Leu | 38 | . | . | B | B | . | . | . | -2.02 | 0.57 | * | * | . | -0.60 | 0.25 |
| Val | 39 | . | . | B | B | . | . | . | -1.76 | 0.79 | . | . | . | -0.60 | 0.09 |
| Leu | 40 | A | . | . | B | . | . | . | -2.13 | 1.29 | . | . | . | -0.60 | 0.06 |
| Val | 41 | A | . | . | B | . | . | . | -3.03 | 1.30 | . | . | . | -0.60 | 0.08 |
| Val | 42 | A | . | . | B | . | . | . | -3.53 | 1.26 | . | . | . | -0.60 | 0.08 |
| Ala | 43 | A | . | . | B | . | . | . | -3.53 | 1.30 | . | . | . | -0.60 | 0.08 |
| Ala | 44 | A | . | . | B | . | . | . | -3.49 | 1.30 | . | . | . | -0.60 | 0.09 |
| Val | 45 | A | . | . | B | . | . | . | -3.53 | 1.34 | . | . | . | -0.60 | 0.10 |
| Leu | 46 | A | . | . | B | . | . | . | -2.98 | 1.34 | . | . | . | -0.60 | 0.07 |
| Leu | 47 | A | . | . | B | . | . | . | -2.71 | 1.23 | . | . | . | -0.60 | 0.09 |
| Leu | 48 | A | . | . | B | . | . | . | -2.12 | 1.23 | . | . | . | -0.60 | 0.13 |
| Val | 49 | A | . | . | B | . | . | . | -1.83 | 0.59 | . | . | . | -0.60 | 0.27 |
| Ser | 50 | A | . | . | B | . | . | . | -1.57 | 0.29 | . | * | . | -0.30 | 0.44 |
| Ala | 51 | A | A | . | . | . | . | . | -1.57 | 0.10 | . | . | . | -0.30 | 0.54 |
| Glu | 52 | A | A | . | . | . | . | . | -1.64 | 0.10 | . | . | . | -0.30 | 0.60 |
| Ser | 53 | A | A | . | B | . | . | . | -1.14 | 0.14 | . | . | . | -0.30 | 0.31 |
| Ala | 54 | A | A | . | B | . | . | . | -0.29 | 0.24 | . | . | . | -0.30 | 0.45 |
| Leu | 55 | A | A | . | B | . | . | . | 0.01 | 0.14 | . | . | . | -0.30 | 0.45 |
| Ile | 56 | A | A | . | B | . | . | . | 0.60 | 0.54 | . | . | . | -0.60 | 0.58 |
| Thr | 57 | A | A | . | B | . | . | . | -0.21 | 0.16 | . | . | F | -0.15 | 0.96 |
| Gln | 58 | A | A | . | B | . | . | . | -0.50 | 0.34 | . | . | F | -0.15 | 0.96 |
| Gln | 59 | A | A | . | B | . | . | . | -0.12 | 0.16 | . | . | F | 0.00 | 1.38 |
| Asp | 60 | . | A | . | B | T | . | . | 0.69 | -0.10 | . | . | F | 1.00 | 1.48 |
| Leu | 61 | . | A | . | . | . | . | C | 1.58 | -0.19 | . | * | F | 0.80 | 1.48 |
| Ala | 62 | . | A | . | . | . | . | C | 2.00 | -0.19 | . | * | F | 0.80 | 1.48 |
| Pro | 63 | . | A | . | . | . | . | C | 1.41 | -0.59 | . | * | F | 1.10 | 1.73 |
| Gln | 64 | . | A | . | . | T | . | . | 0.82 | -0.09 | . | * | F | 1.00 | 2.13 |
| Gln | 65 | A | A | . | . | . | . | . | 0.61 | -0.27 | . | * | F | 0.60 | 2.13 |
| Arg | 66 | A | A | . | . | . | . | . | 1.42 | -0.34 | . | * | F | 0.60 | 2.13 |
| Ala | 67 | A | A | . | . | . | . | . | 2.01 | -0.37 | . | * | F | 0.94 | 2.13 |
| Ala | 68 | A | A | . | . | . | . | . | 2.27 | -0.37 | * | * | F | 1.28 | 2.13 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Pro | 69 | A | A | . | . | . | . | . | 2.38 | -0.77 | * | * | F | 1.92 | 2.17 |
| Gln | 70 | . | A | . | . | T | . | . | 2.08 | -0.77 | * | . | F | 2.66 | 4.21 |
| Gln | 71 | . | . | . | . | T | T | . | 1.67 | -0.89 | * | * | F | 3.40 | 5.58 |
| Lys | 72 | . | . | . | . | T | T | . | 2.04 | -1.00 | . | . | F | 3.06 | 4.84 |
| Arg | 73 | . | . | . | . | T | T | . | 2.33 | -1.00 | . | . | F | 2.97 | 4.32 |
| Ser | 74 | . | . | . | . | . | T | C | 2.54 | -1.01 | . | . | F | 2.68 | 3.34 |
| Ser | 75 | . | . | . | . | . | T | C | 2.20 | -1.41 | . | . | F | 2.59 | 2.89 |
| Pro | 76 | . | . | . | . | T | T | . | 1.39 | -0.99 | . | . | F | 2.70 | 1.46 |
| Ser | 77 | . | . | . | . | T | T | . | 0.68 | -0.30 | . | . | F | 2.50 | 0.90 |
| Glu | 78 | . | . | . | . | T | T | . | 0.36 | -0.11 | . | * | F | 2.25 | 0.36 |
| Gly | 79 | . | . | . | . | T | . | . | 0.44 | -0.07 | . | . | F | 1.80 | 0.36 |
| Leu | 80 | . | . | . | . | T | . | . | 0.40 | -0.07 | . | . | F | 1.55 | 0.42 |
| Cys | 81 | . | . | . | . | . | . | C | 0.58 | -0.03 | . | . | . | 0.95 | 0.24 |
| Pro | 82 | . | . | . | . | . | T | C | 0.84 | 0.47 | * | . | F | 0.15 | 0.33 |
| Pro | 83 | . | . | . | . | T | T | . | -0.04 | 0.54 | * | . | F | 0.35 | 0.54 |
| Gly | 84 | . | . | . | . | T | T | . | 0.00 | 0.54 | * | . | . | 0.20 | 0.70 |
| His | 85 | . | . | . | . | . | T | C | 0.81 | 0.36 | * | . | . | 0.30 | 0.61 |
| His | 86 | . | . | . | . | . | . | C | 1.48 | -0.07 | * | . | . | 0.70 | 0.68 |
| Ile | 87 | . | . | . | . | . | . | C | 1.34 | -0.50 | * | * | . | 1.19 | 1.15 |
| Ser | 88 | . | . | . | . | . | . | C | 1.67 | -0.50 | * | * | F | 1.53 | 0.84 |
| Glu | 89 | . | . | . | . | T | . | . | 2.01 | -1.00 | * | * | F | 2.52 | 1.21 |
| Asp | 90 | . | . | . | . | T | . | . | 1.38 | -1.50 | * | * | F | 2.86 | 2.88 |
| Gly | 91 | . | . | . | . | T | T | . | 0.52 | -1.61 | * | * | F | 3.40 | 1.15 |
| Arg | 92 | . | . | . | . | T | T | . | 1.11 | -1.31 | * | * | F | 2.91 | 0.47 |
| Asp | 93 | . | . | . | . | T | T | . | 0.74 | -0.93 | . | * | F | 2.57 | 0.37 |
| Cys | 94 | . | . | . | . | T | T | . | 0.79 | 0.36 | . | * | . | 1.78 | 0.20 |
| Ile | 95 | . | . | . | . | T | . | . | 0.54 | -0.79 | . | * | . | 1.54 | 0.21 |
| Ser | 96 | . | . | . | . | T | . | . | 0.54 | -0.03 | . | * | . | 1.18 | 0.19 |
| Cys | 97 | . | . | . | . | T | T | . | 0.43 | 0.40 | . | * | . | 0.76 | 0.36 |
| Lys | 98 | . | . | . | . | T | T | . | 0.43 | 0.23 | . | . | . | 1.34 | 0.88 |
| Tyr | 99 | . | . | . | . | T | T | . | 0.86 | -0.46 | . | * | F | 2.52 | 1.10 |
| Gly | 100 | . | . | . | . | T | T | . | 1.44 | -0.09 | . | * | F | 2.80 | 3.22 |
| Gln | 101 | . | . | . | . | T | T | . | 1.43 | -0.27 | . | . | F | 2.52 | 2.16 |
| Asp | 102 | . | . | . | . | T | T | . | 2.07 | 0.21 | * | * | F | 1.64 | 1.99 |
| Tyr | 103 | . | . | . | . | T | T | . | 1.73 | -0.04 | * | * | F | 1.96 | 2.73 |
| Ser | 104 | . | . | . | . | T | T | . | 1.98 | 0.44 | * | . | F | 0.78 | 1.66 |
| Thr | 105 | . | . | . | . | T | . | . | 2.32 | 0.44 | * | . | F | 0.30 | 1.60 |
| His | 106 | . | . | . | . | T | . | . | 1.51 | 0.44 | * | . | . | 0.15 | 1.70 |
| Trp | 107 | . | . | . | . | T | T | . | 0.70 | 0.37 | * | . | . | 0.65 | 1.05 |
| Asn | 108 | . | . | . | . | T | T | . | 0.24 | 0.67 | . | . | . | 0.20 | 0.60 |
| Asp | 109 | . | . | . | . | T | T | . | -0.12 | 0.97 | * | . | . | 0.20 | 0.38 |
| Leu | 110 | A | . | . | . | . | T | . | -0.62 | 1.04 | * | . | . | -0.20 | 0.19 |
| Leu | 111 | . | . | . | B | T | . | . | -0.48 | 0.81 | * | * | . | -0.20 | 0.10 |
| Phe | 112 | . | . | . | B | T | . | . | -0.86 | 0.41 | * | * | . | -0.20 | 0.12 |
| Cys | 113 | . | . | . | B | T | . | . | -1.17 | 0.99 | * | * | . | -0.20 | 0.08 |
| Leu | 114 | . | . | . | B | T | . | . | -1.06 | 0.79 | . | * | . | -0.20 | 0.13 |
| Arg | 115 | . | . | . | B | T | . | . | -0.91 | 0.10 | * | * | . | 0.10 | 0.30 |
| Cys | 116 | . | . | . | B | T | . | . | -0.10 | -0.11 | . | . | . | 0.70 | 0.30 |
| Thr | 117 | . | . | . | B | T | . | . | 0.30 | -0.69 | . | * | . | 1.00 | 0.61 |
| Arg | 118 | . | . | . | B | T | . | . | 0.62 | -0.99 | . | . | F | 1.49 | 0.42 |
| Cys | 119 | . | . | . | . | T | T | . | 1.43 | -0.56 | . | . | F | 2.23 | 0.77 |
| Asp | 120 | . | . | . | . | T | T | . | 0.47 | -1.13 | * | . | F | 2.57 | 0.92 |
| Ser | 121 | . | . | . | . | T | T | . | 1.13 | -0.97 | . | * | F | 2.91 | 0.35 |
| Gly | 122 | . | . | . | . | T | T | . | 0.63 | -0.97 | . | * | F | 3.40 | 1.13 |
| Glu | 123 | . | . | . | . | T | . | . | 0.22 | -0.86 | . | * | F | 2.51 | 0.56 |
| Val | 124 | A | A | . | . | . | . | . | 0.68 | -0.47 | . | * | F | 1.47 | 0.56 |
| Glu | 125 | . | A | . | . | T | . | . | 0.01 | -0.43 | . | * | . | 1.38 | 0.87 |
| Leu | 126 | . | A | . | . | T | . | . | 0.00 | -0.29 | . | * | . | 1.04 | 0.27 |
| Ser | 127 | . | . | . | . | . | T | C | 0.03 | 0.20 | . | * | F | 0.45 | 0.52 |
| Pro | 128 | . | . | . | . | T | T | . | -0.28 | 0.04 | . | * | F | 0.93 | 0.44 |
| Cys | 129 | . | . | . | . | T | T | . | 0.69 | 0.53 | . | * | F | 0.91 | 0.77 |
| Thr | 130 | . | . | . | . | T | T | . | 0.69 | -0.16 | . | * | F | 2.24 | 1.12 |
| Thr | 131 | . | . | . | . | T | . | . | 1.19 | -0.14 | . | * | F | 2.32 | 1.16 |
| Thr | 132 | . | . | . | . | T | T | . | 0.63 | -0.09 | . | * | F | 2.80 | 3.13 |
| Arg | 133 | . | . | . | . | T | T | . | 0.18 | -0.01 | . | . | F | 2.52 | 1.61 |
| Asn | 134 | . | . | . | . | T | T | . | 0.84 | 0.07 | . | . | F | 1.49 | 0.60 |
| Thr | 135 | . | . | . | . | T | T | . | 0.49 | -0.01 | . | . | F | 1.81 | 0.72 |
| Val | 136 | . | . | . | . | T | . | C | 0.80 | 0.07 | * | . | . | 0.58 | 0.20 |
| Cys | 137 | . | A | . | . | T | . | . | 1.11 | 0.07 | * | . | . | 0.10 | 0.21 |
| Gln | 138 | . | A | B | . | . | . | . | 0.66 | -0.33 | * | . | . | 0.30 | 0.25 |
| Cys | 139 | . | A | . | . | T | . | . | 0.34 | -0.39 | . | . | . | 0.70 | 0.34 |
| Glu | 140 | A | A | . | . | . | . | . | -0.04 | -0.54 | . | * | F | 0.75 | 0.91 |
| Glu | 141 | A | A | . | . | . | . | . | 0.92 | -0.33 | . | * | F | 0.45 | 0.46 |
| Gly | 142 | . | A | . | . | T | . | . | 1.59 | -0.73 | . | * | F | 1.30 | 1.67 |
| Thr | 143 | A | A | . | . | . | . | . | 1.59 | -1.30 | . | * | F | 0.90 | 1.67 |
| Phe | 144 | A | A | . | . | . | . | . | 2.26 | -1.30 | . | * | F | 0.90 | 1.67 |
| Arg | 145 | A | A | . | . | . | . | . | 1.96 | -1.30 | . | * | F | 0.90 | 2.81 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Glu | 146 | A | A | . | . | . | . | . | 1.74 | -1.34 | . | * | F | 0.90 | 2.61 |
| Glu | 147 | A | A | . | . | . | . | . | 2.09 | -1.40 | . | * | F | 0.90 | 4.66 |
| Asp | 148 | A | A | . | . | . | . | . | 1.80 | -2.19 | . | * | F | 0.90 | 4.12 |
| Ser | 149 | A | . | . | . | . | T | . | 1.83 | -1.57 | . | * | F | 1.30 | 2.35 |
| Pro | 150 | A | . | . | . | . | T | . | 1.83 | -1.00 | . | . | F | 1.15 | 0.73 |
| Glu | 151 | A | . | . | . | . | T | . | 1.88 | -1.00 | * | . | F | 1.15 | 0.85 |
| Met | 152 | A | . | . | . | . | T | . | 1.21 | -1.00 | * | * | . | 1.49 | 1.28 |
| Cys | 153 | A | . | . | . | . | T | . | 1.32 | -0.81 | * | * | . | 1.68 | 0.44 |
| Arg | 154 | A | . | . | . | . | T | . | 1.31 | -1.24 | * | . | . | 2.02 | 0.50 |
| Lys | 155 | . | . | . | . | T | T | . | 1.18 | -0.76 | * | * | F | 2.91 | 0.73 |
| Cys | 156 | . | . | . | . | T | T | . | 0.51 | -0.94 | * | . | F | 3.40 | 1.35 |
| Arg | 157 | . | . | . | . | T | . | . | 0.90 | -0.94 | * | . | F | 2.71 | 0.37 |
| Thr | 158 | . | . | . | . | T | . | . | 1.68 | -0.51 | * | . | F | 2.37 | 0.28 |
| Gly | 159 | . | . | . | . | T | . | . | 1.22 | -0.51 | * | . | F | 2.43 | 1.04 |
| Cys | 160 | . | . | . | . | . | T | C | 0.58 | -0.66 | . | * | F | 2.19 | 0.53 |
| Pro | 161 | . | . | . | . | T | T | . | 0.39 | -0.04 | . | * | F | 2.00 | 0.36 |
| Arg | 162 | . | . | . | . | T | T | . | 0.32 | 0.11 | . | * | F | 1.65 | 0.27 |
| Gly | 163 | . | . | . | . | T | T | . | -0.22 | 0.31 | * | * | . | 2.50 | 1.01 |
| Met | 164 | . | . | B | B | . | . | . | -0.22 | -0.24 | * | * | . | 1.30 | 0.48 |
| Val | 165 | . | . | B | B | . | . | . | 0.44 | -0.24 | * | * | . | 1.30 | 0.24 |
| Lys | 166 | . | . | B | B | . | . | . | -0.01 | -0.24 | * | * | . | 1.30 | 0.41 |
| Val | 167 | . | . | B | . | . | T | . | -0.43 | -0.10 | * | * | F | 1.85 | 0.22 |
| Gly | 168 | . | . | . | . | T | T | . | -0.30 | -0.23 | . | . | F | 2.25 | 0.44 |
| Asp | 169 | . | . | . | . | T | T | . | 0.01 | -0.44 | . | . | F | 2.50 | 0.34 |
| Cys | 170 | . | . | . | . | T | T | . | 0.57 | 0.47 | . | * | F | 1.35 | 0.48 |
| Thr | 171 | . | . | . | . | . | T | C | 0.52 | 0.21 | . | * | F | 1.20 | 0.65 |
| Pro | 172 | . | . | . | . | T | T | . | 0.49 | -0.21 | . | * | F | 1.75 | 0.65 |
| Trp | 173 | . | . | . | . | T | T | . | 0.83 | 0.47 | . | * | F | 0.60 | 0.84 |
| Ser | 174 | A | . | . | . | . | T | . | 0.17 | -0.10 | . | * | F | 1.00 | 1.01 |
| Asp | 175 | A | A | . | . | . | . | . | -0.02 | -0.01 | . | . | F | 0.45 | 0.35 |
| Ile | 176 | A | A | . | . | . | . | . | 0.26 | 0.20 | * | * | . | -0.30 | 0.25 |
| Glu | 177 | A | A | . | . | . | . | . | 0.51 | -0.21 | * | . | . | 0.30 | 0.25 |
| Cys | 178 | A | A | . | . | . | . | . | 0.80 | -0.60 | * | . | . | 0.60 | 0.30 |
| Val | 179 | A | A | . | . | . | . | . | 0.80 | -0.60 | * | * | . | 0.60 | 0.74 |
| His | 100 | A | A | . | . | . | . | . | 0.46 | -0.90 | . | * | . | 0.60 | 0.58 |
| Lys | 181 | A | A | . | . | . | . | . | 0.46 | -0.47 | * | . | F | 0.60 | 1.06 |
| Glu | 182 | A | . | . | . | . | T | . | -0.43 | -0.36 | * | . | F | 1.00 | 1.00 |
| Ser | 183 | A | . | . | . | . | T | . | -0.66 | -0.31 | . | . | F | 0.85 | 0.52 |
| Gly | 184 | A | . | . | . | T | T | . | -0.14 | -0.13 | . | . | F | 1.25 | 0.18 |
| Ile | 185 | A | . | . | . | . | T | . | -0.97 | 0.30 | . | . | . | 0.10 | 0.10 |
| Ile | 186 | . | . | B | B | . | . | . | -1.32 | 0.94 | . | * | . | -0.60 | 0.06 |
| Ile | 187 | . | . | B | B | . | . | . | -2.18 | 1.04 | . | . | . | -0.60 | 0.08 |
| Gly | 188 | . | . | B | B | . | . | . | -2.47 | 1.26 | . | * | . | -0.60 | 0.09 |
| Val | 189 | . | . | B | B | . | . | . | -2.71 | 1.07 | . | . | . | -0.60 | 0.13 |
| Thr | 190 | A | . | . | B | . | . | . | -2.68 | 0.89 | . | * | . | -0.60 | 0.18 |
| Val | 191 | A | . | . | B | . | . | . | -2.64 | 0.84 | . | . | . | -0.60 | 0.14 |
| Ala | 192 | A | . | . | B | . | . | . | -2.57 | 1.06 | . | * | . | -0.60 | 0.14 |
| Ala | 193 | A | . | . | B | . | . | . | -3.11 | 1.10 | . | . | . | -0.60 | 0.08 |
| Val | 194 | A | . | . | B | . | . | . | -3.11 | 1.30 | . | . | . | -0.60 | 0.07 |
| Val | 195 | A | . | . | B | . | . | . | -3.39 | 1.30 | . | . | . | -0.60 | 0.05 |
| Leu | 196 | A | . | . | B | . | . | . | -3.39 | 1.30 | . | . | . | -0.60 | 0.05 |
| Ile | 197 | A | . | . | B | . | . | . | -3.50 | 1.44 | . | . | . | -0.60 | 0.05 |
| Val | 198 | A | . | . | B | . | . | . | -3.77 | 1.59 | . | . | . | -0.60 | 0.06 |
| Ala | 199 | A | . | . | B | . | . | . | -3.58 | 1.59 | . | . | . | -0.60 | 0.06 |
| Val | 200 | A | . | . | B | . | . | . | -2.68 | 1.47 | . | . | . | -0.60 | 0.04 |
| Phe | 201 | A | . | . | B | . | . | . | -2.17 | 0.79 | . | . | . | -0.60 | 0.12 |
| Val | 202 | A | . | . | B | . | . | . | -2.09 | 0.53 | . | . | . | -0.60 | 0.16 |
| Cys | 203 | A | . | . | . | . | T | . | -2.04 | 0.71 | . | . | . | -0.20 | 0.17 |
| Lys | 204 | A | . | . | . | . | T | . | -1.74 | 0.76 | . | . | . | -0.20 | 0.17 |
| Ser | 205 | A | . | . | . | . | T | . | -0.84 | 0.89 | . | . | . | -0.20 | 0.24 |
| Leu | 206 | A | . | . | . | . | T | . | -0.10 | 0.24 | . | . | . | 0.10 | 0.88 |
| Leu | 207 | A | A | . | . | . | . | . | -0.10 | -0.33 | . | . | . | 0.30 | 0.88 |
| Trp | 208 | A | A | . | . | . | . | . | -0.24 | 0.31 | . | . | . | -0.30 | 0.49 |
| Lys | 209 | A | A | . | . | . | . | . | -0.50 | 0.61 | . | . | . | -0.60 | 0.49 |
| Lys | 210 | A | A | . | . | . | . | . | -0.44 | 0.36 | * | . | . | -0.30 | 0.91 |
| Val | 211 | A | A | . | . | . | . | . | -0.44 | 0.43 | * | * | . | -0.45 | 1.36 |
| Leu | 212 | . | A | B | . | . | . | . | 0.41 | 0.20 | * | * | . | -0.30 | 0.56 |
| Pro | 213 | . | A | B | . | . | . | . | 0.36 | 0.20 | * | . | . | -0.30 | 0.56 |
| Tyr | 214 | . | . | . | B | T | . | . | -0.58 | 0.63 | * | . | . | -0.20 | 0.75 |
| Leu | 215 | . | . | . | B | T | . | . | -1.29 | 0.67 | * | * | . | -0.20 | 0.64 |
| Lys | 216 | . | . | . | B | T | . | . | -0.73 | 0.56 | * | . | . | -0.20 | 0.22 |
| Gly | 217 | . | . | B | B | . | . | . | -0.27 | 0.51 | * | . | . | -0.60 | 0.19 |
| Ile | 218 | . | . | B | B | . | . | . | -0.40 | 0.19 | * | . | . | -0.30 | 0.23 |
| Cys | 219 | . | . | . | B | . | T | . | -0.50 | -0.07 | * | . | . | 0.70 | 0.11 |
| Ser | 220 | . | . | . | . | T | T | . | -0.03 | 0.36 | . | * | F | 0.65 | 0.11 |
| Gly | 221 | . | . | . | . | T | T | . | -0.08 | 0.36 | . | . | F | 0.65 | 0.16 |
| Gly | 222 | . | . | . | . | T | T | . | 0.06 | -0.33 | . | . | F | 1.25 | 0.49 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Gly | 223 | . | . | . | . | . | . | C | 0.94 | -0.47 | . | . | F | 0.85 | 0.57 |
| Gly | 224 | . | . | . | . | . | . | C | 1.72 | -0.86 | * | . | F | 1.15 | 0.99 |
| Asp | 225 | . | . | . | . | . | T | C | 1.17 | -1.29 | . | * | F | 1.50 | 1.97 |
| Pro | 226 | . | . | . | . | . | T | C | 1.51 | -1.07 | * | . | F | 1.84 | 1.47 |
| Glu | 227 | . | . | B | . | . | T | . | 1.97 | -1.50 | * | . | F | 1.98 | 2.49 |
| Arg | 228 | . | . | B | . | . | . | T | 2.01 | -1.93 | * | . | F | 2.32 | 2.92 |
| Val | 229 | . | . | . | . | T | . | . | 2.06 | -1.54 | * | . | F | 2.86 | 2.53 |
| Asp | 230 | . | . | . | . | . | T | T | . | 2.06 | -1.59 | * | . | F | 3.40 | 1.96 |
| Arg | 231 | . | . | . | . | . | T | T | . | 2.38 | -1.19 | * | * | F | 3.06 | 1.73 |
| Ser | 232 | . | . | . | . | . | T | T | . | 2.17 | -1.19 | * | . | F | 2.72 | 4.57 |
| Ser | 233 | . | . | . | . | . | T | T | . | 1.71 | -1.40 | * | * | F | 2.72 | 4.23 |
| Gln | 234 | . | . | . | . | . | . | C | 1.98 | -0.97 | * | * | F | 2.32 | 2.14 |
| Arg | 235 | . | . | . | . | . | T | C | 1.98 | -0.47 | * | * | F | 2.22 | 1.61 |
| Pro | 236 | . | . | . | . | . | T | C | 1.87 | -0.86 | * | * | F | 2.86 | 2.08 |
| Gly | 237 | . | . | . | . | T | T | . | 2.17 | -1.24 | . | * | F | 3.40 | 2.01 |
| Ala | 238 | . | . | . | . | . | T | C | 1.61 | -1.24 | * | . | F | 2.86 | 1.65 |
| Glu | 239 | A | . | . | . | . | . | . | 0.80 | -0.60 | . | * | F | 1.97 | 0.79 |
| Asp | 240 | A | . | . | . | . | . | . | 0.69 | -0.34 | . | * | F | 1.33 | 0.66 |
| Asn | 241 | A | . | . | . | . | . | . | 0.90 | -0.37 | * | . | . | 0.99 | 1.05 |
| Val | 242 | A | . | . | . | . | . | . | 0.36 | -0.87 | * | . | . | 0.95 | 1.05 |
| Leu | 243 | A | . | . | . | . | . | . | 0.09 | -0.19 | * | . | . | 0.50 | 0.44 |
| Asn | 244 | A | . | . | B | . | . | . | -0.21 | 0.46 | * | . | . | -0.60 | 0.20 |
| Glu | 245 | A | . | . | B | . | . | . | -1.10 | 0.44 | * | . | . | -0.60 | 0.37 |
| Ile | 246 | A | . | . | B | . | . | . | -1.91 | 0.49 | * | . | . | -0.60 | 0.31 |
| Val | 247 | A | . | . | B | . | . | . | -1.06 | 0.49 | * | . | . | -0.60 | 0.16 |
| Ser | 248 | . | . | B | B | . | . | . | -0.46 | 0.49 | * | . | . | -0.60 | 0.16 |
| Ile | 249 | . | . | B | B | . | . | . | -0.77 | 0.91 | * | . | . | -0.60 | 0.35 |
| Leu | 250 | . | . | . | B | . | . | C | -0.77 | 0.71 | . | . | . | -0.40 | 0.69 |
| Gln | 251 | . | . | . | . | . | T | C | -0.73 | 0.47 | . | . | F | 0.15 | 0.89 |
| Pro | 252 | . | . | . | . | . | T | C | -0.09 | 0.73 | . | . | F | 0.15 | 0.94 |
| Thr | 253 | . | . | . | . | . | T | C | 0.21 | 0.47 | . | . | F | 0.30 | 1.76 |
| Gln | 254 | . | . | . | . | . | T | C | 1.10 | -0.21 | . | . | F | 1.20 | 1.76 |
| Val | 255 | . | A | . | . | . | . | C | 1.91 | -0.21 | . | . | F | 0.80 | 1.97 |
| Pro | 256 | . | A | . | . | . | . | C | 1.31 | -0.64 | . | . | F | 1.10 | 2.37 |
| Glu | 257 | A | A | . | . | . | . | . | 1.52 | -0.51 | . | * | F | 0.90 | 1.35 |
| Gln | 258 | A | A | . | . | . | . | . | 0.98 | -0.91 | . | * | F | 0.90 | 3.16 |
| Glu | 259 | A | A | . | . | . | . | . | 0.98 | -0.91 | . | * | F | 0.90 | 1.51 |
| Met | 260 | A | A | . | . | . | . | . | 1.83 | -0.94 | . | * | F | 0.90 | 1.51 |
| Glu | 261 | A | A | . | . | . | . | . | 1.83 | -0.94 | . | * | . | 0.75 | 1.51 |
| Val | 262 | A | A | . | . | . | . | . | 1.24 | -0.91 | . | * | F | 0.90 | 1.35 |
| Gln | 263 | A | A | . | . | . | . | . | 1.24 | -0.41 | . | * | F | 0.60 | 1.38 |
| Glu | 264 | A | A | . | . | . | . | . | 1.03 | -1.03 | . | * | F | 0.90 | 1.38 |
| Pro | 265 | A | A | . | . | . | . | . | 1.32 | -0.60 | . | * | F | 1.18 | 2.88 |
| Ala | 266 | A | A | . | . | . | . | . | 0.98 | -0.76 | . | * | F | 1.46 | 2.40 |
| Glu | 267 | A | . | . | . | . | T | . | 0.98 | -0.73 | . | * | F | 2.14 | 1.37 |
| Pro | 268 | A | . | . | . | . | T | . | 0.98 | -0.09 | . | . | F | 1.97 | 0.66 |
| Thr | 269 | . | . | . | . | T | T | . | 0.38 | -0.11 | . | . | F | 2.80 | 1.05 |
| Gly | 270 | A | . | . | . | . | T | . | -0.22 | 0.00 | . | . | F | 1.37 | 0.60 |
| Val | 271 | A | . | . | . | . | . | . | 0.07 | 0.69 | . | . | . | 0.44 | 0.32 |
| Asn | 272 | . | . | B | . | . | . | . | -0.14 | 0.64 | . | . | . | 0.16 | 0.30 |
| Met | 273 | . | . | B | . | . | . | . | -0.28 | 0.59 | . | . | . | 0.18 | 0.46 |
| Leu | 274 | . | . | . | . | . | . | C | 0.03 | 0.59 | . | . | . | 0.40 | 0.62 |
| Ser | 275 | . | . | . | . | . | T | C | 0.08 | -0.06 | . | . | F | 1.95 | 0.66 |
| Pro | 276 | . | . | . | . | . | T | C | 0.93 | -0.07 | . | . | F | 2.25 | 0.90 |
| Gly | 277 | . | . | . | . | . | T | C | 0.90 | -0.69 | . | . | F | 3.00 | 1.89 |
| Glu | 278 | A | . | . | . | . | T | . | 0.69 | -0.87 | . | . | F | 2.50 | 1.92 |
| Ser | 279 | A | A | . | . | . | . | . | 0.69 | -0.57 | . | . | F | 1.80 | 1.02 |
| Glu | 280 | A | A | . | . | . | . | . | 0.99 | -0.31 | . | . | F | 1.05 | 0.85 |
| His | 281 | A | A | . | . | . | . | . | 0.99 | -0.74 | . | . | F | 1.05 | 0.85 |
| Leu | 282 | A | A | . | . | . | . | . | 0.74 | -0.31 | . | . | . | 0.30 | 0.98 |
| Leu | 283 | A | A | . | . | . | . | . | 0.74 | -0.20 | . | . | . | 0.30 | 0.57 |
| Glu | 284 | A | A | . | . | . | . | . | 0.46 | -0.20 | . | . | F | 0.45 | 0.73 |
| Pro | 285 | A | A | . | . | . | . | . | 0.46 | -0.20 | . | . | F | 0.45 | 0.89 |
| Ala | 286 | A | A | . | . | . | . | . | 0.60 | -0.89 | . | . | F | 0.90 | 1.88 |
| Glu | 287 | A | A | . | . | . | . | . | 1.11 | -1.57 | . | . | F | 0.90 | 2.13 |
| Ala | 288 | A | A | . | . | . | . | . | 1.92 | -1.19 | . | . | F | 0.90 | 1.84 |
| Glu | 289 | A | A | . | . | . | . | . | 2.03 | -1.21 | . | . | F | 0.90 | 3.16 |
| Arg | 290 | A | A | . | . | . | . | . | 2.36 | -1.71 | * | . | F | 0.90 | 3.57 |
| Ser | 291 | A | . | . | . | . | T | . | 3.06 | -1.71 | * | . | F | 1.30 | 6.92 |
| Gln | 292 | A | . | . | . | . | T | . | 2.24 | -2.21 | * | . | F | 1.30 | 7.83 |
| Arg | 293 | A | . | . | . | . | T | . | 2.02 | -1.53 | . | . | F | 1.30 | 3.30 |
| Arg | 294 | A | . | . | . | . | T | . | 1.17 | -0.84 | . | . | F | 1.30 | 2.03 |
| Arg | 295 | . | . | . | B | T | . | . | 0.84 | -0.59 | . | * | F | 1.15 | 0.87 |
| Leu | 296 | . | . | . | B | B | . | . | 0.56 | -0.56 | . | * | . | 0.60 | 0.69 |
| Leu | 297 | . | . | . | B | B | . | . | 0.56 | -0.06 | . | * | . | 0.30 | 0.35 |
| Val | 298 | . | . | . | B | . | . | C | 0.44 | 0.34 | * | * | . | 0.20 | 0.29 |
| Pro | 299 | . | . | . | . | . | T | C | -0.01 | 0.34 | * | . | . | 0.90 | 0.61 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Ala | 300 | . | . | . | . | . | T | C | -0.12 | 0.09 | * | * | F | 1.35 | 0.73 |
| Asn | 301 | . | . | . | . | . | T | C | 0.48 | -0.60 | . | . | F | 2.70 | 1.65 |
| Glu | 302 | . | . | . | . | . | T | C | 0.98 | -0.81 | . | . | F | 3.00 | 1.65 |
| Gly | 303 | . | . | . | . | . | . | C | 1.83 | -0.76 | . | . | F | 2.50 | 2.35 |
| Asp | 304 | . | . | . | . | . | T | C | 1.73 | -1.26 | . | . | F | 2.40 | 2.54 |
| Pro | 305 | . | . | . | . | . | T | C | 1.51 | -1.17 | . | * | F | 2.10 | 2.11 |
| Thr | 306 | A | . | . | . | . | T | . | 1.62 | -0.49 | . | * | F | 1.30 | 1.76 |
| Glu | 307 | A | . | . | . | . | T | . | 1.62 | -0.91 | * | * | F | 1.30 | 2.07 |
| Thr | 308 | A | . | . | B | . | . | . | 1.30 | -0.51 | * | * | F | 0.90 | 2.31 |
| Leu | 309 | A | . | . | B | . | . | . | 0.60 | -0.37 | * | * | F | 0.45 | 0.86 |
| Arg | 310 | A | . | . | B | . | . | . | 0.81 | -0.07 | * | * | . | 0.30 | 0.43 |
| Gln | 311 | A | . | . | B | . | . | . | 1.12 | -0.07 | * | * | . | 0.30 | 0.50 |
| Cys | 312 | A | . | . | . | . | T | . | 0.42 | -0.56 | * | * | . | 1.15 | 1.01 |
| Phe | 313 | A | . | . | . | . | T | . | 0.14 | -0.46 | * | * | . | 0.70 | 0.45 |
| Asp | 314 | . | . | . | . | T | T | . | 0.96 | 0.04 | * | * | . | 0.50 | 0.26 |
| Asp | 315 | A | . | . | . | . | T | . | 0.03 | -0.36 | * | * | . | 0.70 | 0.81 |
| Phe | 316 | A | A | . | . | . | . | . | -0.82 | -0.24 | * | . | . | 0.30 | 0.77 |
| Ala | 317 | A | A | . | . | . | . | . | -0.37 | -0.39 | * | . | . | 0.30 | 0.34 |
| Asp | 318 | A | A | . | . | . | . | . | -0.37 | 0.04 | * | * | . | -0.30 | 0.32 |
| Leu | 319 | A | A | . | . | . | . | . | -0.37 | 0.83 | . | . | . | -0.60 | 0.32 |
| Val | 320 | . | A | . | . | . | . | C | -0.67 | 0.04 | . | . | . | -0.10 | 0.52 |
| Pro | 321 | . | A | . | . | . | . | C | -0.26 | -0.07 | . | . | . | 0.50 | 0.42 |
| Phe | 322 | . | . | . | . | T | T | . | 0.33 | 0.84 | . | . | . | 0.20 | 0.54 |
| Asp | 323 | A | . | . | . | . | T | . | 0.12 | 0.16 | . | . | . | 0.25 | 1.25 |
| Ser | 324 | A | . | . | . | . | T | . | 0.12 | -0.06 | . | . | F | 1.00 | 1.25 |
| Trp | 325 | A | . | . | . | . | T | . | 0.38 | 0.20 | * | * | F | 0.40 | 1.19 |
| Glu | 326 | A | A | . | . | . | . | . | 0.70 | 0.03 | * | . | F | -0.15 | 0.71 |
| Pro | 327 | A | A | . | . | . | . | . | 1.44 | 0.03 | * | . | . | -0.15 | 1.03 |
| Leu | 328 | A | A | . | . | . | . | . | 0.63 | -0.36 | * | . | . | 0.45 | 1.96 |
| Met | 329 | A | A | . | . | . | . | . | 0.59 | -0.59 | * | . | . | 0.60 | 0.93 |
| Arg | 330 | A | A | . | . | . | . | . | 0.07 | -0.16 | * | . | . | 0.30 | 0.60 |
| Lys | 331 | A | A | . | . | . | . | . | -0.53 | 0.10 | * | . | . | -0.30 | 0.60 |
| Leu | 332 | A | A | . | . | . | . | . | -0.32 | 0.03 | * | . | . | -0.30 | 0.60 |
| Gly | 333 | A | A | . | . | . | . | . | 0.49 | -0.59 | * | . | . | 0.60 | 0.51 |
| Leu | 334 | A | A | . | . | . | . | . | 1.09 | -0.19 | * | . | . | 0.30 | 0.41 |
| Met | 335 | A | A | . | . | . | . | . | 0.09 | -0.19 | * | * | . | 0.30 | 0.86 |
| Asp | 336 | A | A | . | . | . | . | . | 0.09 | -0.19 | . | * | F | 0.45 | 0.61 |
| Asn | 337 | A | A | . | . | . | . | . | 0.04 | -0.61 | * | * | F | 0.90 | 1.48 |
| Glu | 338 | A | A | . | . | . | . | . | -0.20 | -0.66 | * | * | F | 0.90 | 1.11 |
| Ile | 339 | A | A | . | . | . | . | . | 0.66 | -0.77 | * | * | F | 0.75 | 0.67 |
| Lys | 340 | A | A | . | . | . | . | . | 0.67 | -0.77 | . | * | F | 0.75 | 0.83 |
| Val | 341 | A | A | . | . | . | . | . | 0.67 | -0.67 | * | * | . | 0.60 | 0.49 |
| Ala | 342 | A | A | . | . | . | . | . | 0.08 | -0.67 | . | . | . | 0.75 | 1.20 |
| Lys | 343 | A | A | . | . | . | . | . | -0.51 | -0.86 | . | * | . | 0.60 | 0.61 |
| Ala | 344 | A | A | . | . | . | . | . | 0.03 | -0.36 | . | * | . | 0.30 | 0.83 |
| Glu | 345 | A | A | . | . | . | . | . | -0.04 | -0.57 | * | . | . | 0.60 | 0.81 |
| Ala | 346 | A | A | . | . | . | . | . | 0.92 | -0.57 | * | . | . | 0.60 | 0.55 |
| Ala | 347 | A | A | . | . | . | . | . | 1.51 | -0.57 | . | * | . | 0.75 | 1.07 |
| Gly | 348 | A | . | . | . | . | . | . | 1.16 | -1.07 | . | * | . | 0.95 | 1.03 |
| His | 349 | A | . | . | . | . | T | . | 0.93 | -0.59 | . | . | . | 1.15 | 1.47 |
| Arg | 350 | A | . | . | . | . | T | . | 0.69 | -0.40 | . | . | F | 1.00 | 1.20 |
| Asp | 351 | A | . | . | . | . | T | . | 0.97 | -0.14 | . | . | F | 1.00 | 1.90 |
| Thr | 352 | A | . | . | . | . | T | . | 0.96 | -0.09 | . | . | F | 1.00 | 2.02 |
| Leu | 353 | A | . | . | B | . | . | . | 0.49 | 0.03 | . | . | . | -0.15 | 1.02 |
| Tyr | 354 | A | . | . | B | . | . | . | -0.37 | 0.71 | . | * | . | -0.60 | 0.50 |
| Thr | 355 | A | . | . | B | . | . | . | -0.43 | 1.40 | . | * | . | -0.60 | 0.24 |
| Met | 356 | A | . | . | B | . | . | . | -0.72 | 0.91 | * | . | . | -0.60 | 0.59 |
| Leu | 357 | A | . | . | B | . | . | . | -1.27 | 1.14 | * | . | . | -0.60 | 0.40 |
| Ile | 358 | A | . | . | B | . | . | . | -0.46 | 1.03 | * | * | . | -0.60 | 0.20 |
| Lys | 359 | A | . | . | B | . | . | . | -0.17 | 0.94 | * | * | . | -0.60 | 0.33 |
| Trp | 360 | A | . | . | B | . | . | . | -0.17 | 0.33 | * | * | . | 0.00 | 0.81 |
| Val | 361 | A | . | . | B | . | . | . | 0.09 | 0.13 | * | * | . | 0.45 | 1.66 |
| Asn | 362 | . | . | . | . | . | T | C | 1.01 | -0.13 | * | * | F | 1.95 | 0.82 |
| Lys | 363 | . | . | . | . | . | T | C | 1.90 | -0.13 | * | * | F | 2.40 | 1.53 |
| Thr | 364 | . | . | . | . | . | T | C | 1.27 | -1.04 | * | . | F | 3.00 | 3.44 |
| Gly | 365 | . | . | . | . | . | T | C | 1.26 | -1.19 | * | . | F | 2.70 | 2.16 |
| Arg | 366 | . | A | . | . | T | . | . | 1.26 | -1.20 | * | . | F | 2.20 | 1.45 |
| Asp | 367 | . | A | . | . | . | . | C | 1.22 | -0.56 | * | . | F | 1.55 | 0.75 |
| Ala | 368 | A | A | . | . | . | . | . | 0.87 | -0.54 | . | . | F | 1.20 | 1.03 |
| Ser | 369 | A | A | . | . | . | . | . | 0.37 | -0.49 | . | . | . | 0.30 | 0.76 |
| Val | 370 | A | A | . | . | . | . | . | -0.10 | 0.20 | . | * | . | -0.30 | 0.37 |
| His | 371 | A | A | . | . | . | . | . | -0.21 | 0.89 | * | * | . | -0.60 | 0.30 |
| Thr | 372 | A | A | . | . | . | . | . | -0.80 | 0.39 | * | * | . | -0.30 | 0.38 |
| Leu | 373 | A | A | . | . | . | . | . | -1.02 | 0.50 | * | . | . | -0.60 | 0.52 |
| Leu | 374 | A | A | . | . | . | . | . | -0.72 | 0.54 | * | . | . | -0.60 | 0.31 |
| Asp | 375 | A | A | . | . | . | . | . | -0.18 | 0.04 | * | . | . | -0.30 | 0.38 |
| Ala | 376 | A | A | . | . | . | . | . | -0.96 | 0.04 | * | . | . | -0.30 | 0.66 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Leu | 377 | A | A | . | . | . | . | . | -0.99 | 0.04 | * | . | . | -0.30 | 0.66 |
| Glu | 378 | A | A | . | . | . | . | . | -0.18 | -0.21 | * | . | . | 0.30 | 0.39 |
| Thr | 379 | A | A | . | . | . | . | . | 0.74 | -0.21 | * | * | F | 0.45 | 0.67 |
| Leu | 380 | A | A | . | . | . | . | . | -0.07 | -0.71 | * | . | F | 0.90 | 1.59 |
| Gly | 381 | A | A | . | . | . | . | . | -0.07 | -0.71 | * | . | F | 0.75 | 0.76 |
| Glu | 382 | A | A | . | . | . | . | . | 0.79 | -0.21 | * | . | F | 0.45 | 0.53 |
| Arg | 383 | A | A | . | . | . | . | . | 0.79 | -0.70 | * | . | F | 0.90 | 1.28 |
| Leu | 384 | A | A | . | . | . | . | . | 1.14 | -0.99 | * | * | F | 0.90 | 2.24 |
| Ala | 385 | A | A | . | . | . | . | . | 1.07 | -1.41 | * | * | F | 0.90 | 2.59 |
| Lys | 386 | A | A | . | . | . | . | . | 1.41 | -0.73 | * | . | F | 0.75 | 0.93 |
| Gln | 387 | A | A | . | . | . | . | . | 1.41 | -0.73 | * | * | F | 0.90 | 1.95 |
| Lys | 388 | A | A | . | . | . | . | . | 1.27 | -1.41 | * | * | F | 0.90 | 3.22 |
| Ile | 309 | A | A | . | . | . | . | . | 1.27 | -1.41 | . | * | F | 0.90 | 2.19 |
| Glu | 390 | A | A | . | . | . | . | . | 1.04 | -0.73 | * | * | F | 0.90 | 1.04 |
| Asp | 391 | A | A | . | . | . | . | . | 0.70 | -0.44 | . | * | F | 0.45 | 0.43 |
| His | 392 | A | A | . | . | . | . | . | 0.40 | -0.06 | * | * | . | 0.30 | 0.82 |
| Leu | 393 | A | A | . | . | . | . | . | 0.01 | -0.36 | * | * | . | 0.30 | 0.64 |
| Leu | 394 | A | A | . | . | . | . | . | 0.94 | 0.07 | * | * | F | -0.15 | 0.38 |
| Ser | 395 | A | . | . | . | . | T | . | 0.24 | 0.07 | * | * | F | 0.25 | 0.55 |
| Ser | 396 | A | . | . | . | . | T | . | -0.36 | 0.36 | * | * | F | 0.25 | 0.58 |
| Gly | 397 | . | . | . | . | T | T | . | -0.57 | 0.29 | . | . | F | 0.65 | 0.70 |
| Lys | 398 | A | . | . | . | . | T | . | -0.57 | 0.36 | . | . | F | 0.25 | 0.82 |
| Phe | 399 | A | A | . | . | . | . | . | 0.24 | 0.66 | . | . | . | -0.60 | 0.50 |
| Met | 400 | . | A | B | . | . | . | . | 0.20 | 0.27 | . | * | . | -0.30 | 0.88 |
| Tyr | 401 | . | A | B | . | . | . | . | 0.50 | 0.27 | . | * | . | -0.30 | 0.44 |
| Leu | 402 | A | A | . | . | . | . | . | 0.26 | 0.67 | . | * | . | -0.60 | 0.81 |
| Glu | 403 | A | A | . | . | . | . | . | 0.21 | 0.39 | . | * | . | -0.30 | 0.82 |
| Gly | 404 | A | . | . | . | . | . | . | 0.61 | -0.23 | . | * | F | 0.65 | 0.88 |
| Asn | 405 | A | . | . | . | . | T | . | 0.62 | -0.60 | . | * | F | 1.30 | 1.43 |
| Ala | 406 | A | . | . | . | . | T | . | 0.27 | -0.79 | . | * | F | 1.15 | 0.83 |
| Asp | 407 | A | . | . | . | . | T | . | 0.78 | -0.17 | . | * | F | 0.85 | 0.83 |
| Ser | 408 | A | . | . | . | . | T | . | 0.39 | -0.21 | . | * | F | 0.85 | 0.69 |
| Ala | 409 | A | . | . | . | . | . | . | 0.34 | -0.19 | . | * | . | 0.50 | 0.88 |
| Met | 410 | A | . | . | . | . | . | . | -0.04 | -0.26 | . | . | . | 0.50 | 0.67 |
| Ser | 411 | A | . | . | . | . | . | . | 0.16 | 0.17 | . | . | . | -0.10 | 0.64 |

Among highly preferred fragments in this regard are those that comprise, or alternatively consist of, regions of DR5 that combine several structural features, such as several of the features set out above. Preferred nucleic acid fragments of the present invention further include nucleic acid molecules encoding a polypeptide comprising, or alternatively consisting of, one, two, three, four, five, or more epitope-bearing portions of the DR5 protein. In particular, such nucleic acid fragments of the present invention include, but are not limited to, nucleic acid molecules encoding a polypeptide comprising, or alternatively consisting of, one, two, three, or more amino acid sequences selected from the group consisting of: amino acid residues from about 62 to about 110 in FIGS. 1A–B (amino acid residues from about 11 to about 59 in SEQ ID NO:2); a polypeptide comprising, or alternatively consisting of, amino acid residues from about 119 to about 164 in FIGS. 1A–B (amino acid residues from about 68 to about 113 in SEQ ID NO:2); a polypeptide comprising, or alternatively consisting of, amino acid residues from about 224 to about 271 in FIGS. 1A–B (amino acid residues from about 173 to about 220 in SEQ ID NO:2); and a polypeptide comprising, or alternatively consisting of, amino acid residues from about 275 to about 370 in FIGS. 1A–B (amino acid residues from about 224 to about 319 in SEQ ID NO:2). The inventors have determined that the above polypeptide fragments are antigenic regions of the DR5 protein. Methods for determining other such epitope-bearing portions of the DR5 protein are described in detail below. In this context "about" includes the particularly recited value and values larger or smaller by several (5, 4, 3, 2, or 1) amino acid residues. Polypeptides encoded by these nucleic acids are also encompassed by the invention.

Further, the invention includes a polynucleotide comprising, or alternatively consisting of, any portion of at least about 30 nucleotides, preferably at least about 50 nucleotides, of SEQ ID NO:1 from residue 283 to 1,362, preferably from 283 to 681. Polypeptides encoded by these polynucleotides are also encompassed by the invention.

In specific embodiments, the polynucleotides of the invention are less than 100000 kb, 50000 kb, 10000 kb, 1000 kb, 500 kb, 400 kb, 350 kb, 300 kb, 250 kb, 200 kb, 175 kb, 150 kb, 125 kb, 100 kb, 75 kb, 50 kb, 40 kb, 30 kb, 25 kb, 20 kb, 15 kb, 10 kb, 7.5 kb, or 5 kb in length.

In further embodiments, polynucleotides of the invention comprise, or alternatively consisting of, at least 15, at least 30, at least 50, at least 100, or at least 250, at least 500, or at least 1000 contiguous nucleotides of DR5 coding sequence, but consist of less than or equal to 1000 kb, 500 kb, 250 kb, 200 kb, 150 kb, 100 kb, 75 kb, 50 kb, 30 kb, 25 kb, 20 kb, 15 kb, 10kb, or 5 kb of genomic DNA that flanks the 5' or 3' coding nucleotide set forth in FIGS. 1A–B (SEQ ID NO:1). In further embodiments, polynucleotides of the invention comprise, or alternatively consist of, at least 15, at least 30, at least 50, at least 100, or at least 250, at least 500, or at least 1000 contiguous nucleotides of DR5 coding sequence, but do not comprise, or alternatively consist of, all or a portion of any DR5 intron. In another embodiment, the nucleic acid comprising, or alternatively consisting of, DR5 coding sequence does not contain coding sequences of a genomic flanking gene (i.e., 5' or 3' to the DR5 gene in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

In another embodiment, the invention provides an isolated nucleic acid molecule comprising, or alternatively consisting of, a polynucleotide which hybridizes under stringent hybridization conditions to a portion of the polynucleotide in a nucleic acid molecule of the invention described above, for instance, the sequence complementary to the coding and/or noncoding (i.e., transcribed, untranslated) sequence depicted in SEQ ID NO:1, the cDNA contained in ATCC Deposit No. 97920, and the sequence encoding a DR5 domain, or a polynucleotide fragment as described herein. By "stringent hybridization conditions" is intended overnight incubation at 42° C. in a solution comprising, or alternatively consisting of: 50% formamide, 5×SSC (750 mM NaCl, 75 mM trisodium citrate), 50 mM sodium phosphate (pH 7.6). 5× Denhardt's solution, 10% dextran sulfate, and 20 pg/ml denatured, sheared salmon sperm DNA, followed by washing the filters in 0.1×SSC at about 65° C. Polypeptides encoded by these polynucleotides are also encompassed by the invention.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 or 80–150 nt, or the entire length of the reference polynucleotide. By a portion of a polynucleotide of "at least about 20 nt in length," for example, is intended 20 or more contiguous nucleotides from the nucleotide sequence of the reference polynucleotide (e.g., the deposited cDNA or the nucleotide sequence as shown in SEQ ID NO:1) In this context "about" includes the particularly recited size, larger or smaller by several (5, 4, 3, 2, or 1) nucleotides, at either terminus or at both termini. These have uses, which include, but are not limited to, as diagnostic probes and primers as discussed above and in more detail below.

Of course, a polynucleotide which hybridizes only to a poly A sequence (such as the 3' terminal poly(A) tract of the DR5 cDNA shown in FIGS. 1A–B (SEQ ID NO:1)), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA generated from an oligo-dT primed cDNA library).

As indicated, nucleic acid molecules of the present invention which encode a DR5 polypeptide may include, but are not limited to, the coding sequence for the mature polypeptide, by itself; the coding sequence for the mature polypeptide and additional sequences, such as those encoding a leader or secretory sequence, such as a pre-, pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al., *Proc. Natl. Acad. Sci. USA* 86: 821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37:767–778(1984). As discussed below, other such fusion proteins include the DR5 receptor fused to Fc at the N- or C-terminus.

The present invention further relates to variants of the nucleic acid molecules of the present invention, which encode portions, analogs, or derivatives of the DR5 receptor. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques Such variants include those produced by nucleotide substitutions, deletions or additions which may involve one or more nucleotides The variants may be altered in coding or non-coding regions or both. Alterations in the coding regions may produce conservative or non-conservative amino acid substitutions, deletions or additions. Especially preferred among these are silent substitutions, additions, and deletions, which do not alter the properties and activities of the DR5 receptor or portions thereof Also especially preferred in this regard are conservative substitutions.

Further embodiments of the invention include isolated nucleic acid molecules that are at least 80% identical, and more preferably at least 85%, 90%, 92%, 95%, 96%, 97%, 98% or 99% identical, to (a) a nucleotide sequence encoding the polypeptide comprising, or alternatively consisting of, the amino acid sequence in SEQ ID NO:2; (b) a nucleotide sequence encoding the polypeptide comprising, or alternatively consisting of the amino acid sequence in SEQ ID NO:2, but lacking the amino terminal methionine; (c) a nucleotide sequence encoding the polypeptide comprising, or alternatively consisting of, the amino acid sequence at positions from about 1 to about 360 in SEQ ID NO:2; (d) a nucleotide sequence encoding the polypeptide comprising, or alternatively consisting of, the amino acid sequence encoded by the cDNA contained in ATCC Deposit No. 97920, (e) a nucleotide sequence encoding the mature DR5 polypeptide comprising, or alternatively consisting of the amino acid sequence encoded by the cDNA contained in ATCC Deposit No. 97920; (f) a nucleotide sequence that encodes the DR5 extracellular domain comprising, or alternatively consisting of, the amino acid sequence at positions from about 1 to about 133 in SEQ ID NO:2, or the DR5 extracellular domain encoded by the cDNA contained in ATCC Deposit No. 97920; (g) a nucleotide sequence that encodes the DR5 cysteine rich domain comprising, or alternatively consisting of, the amino acid sequence at positions from about 33 to about 128 in SEQ ID NO:2, or the DR5 cysteine rich domain encoded by the cDNA contained in ATCC Deposit No. 97920; (h) a nucleotide sequence that encodes the DR5 transmembrane domain comprising, or alternatively consisting of, the amino acid sequence at positions from about 134 to about 157 of SEQ ID NO:2, or the DR5 transmembrane domain encoded by the cDNA contained in ATCC Deposit No. 97920; (i) a nucleotide sequence that encodes the DR5 intracellular domain comprising, or alternatively consisting of, the amino acid sequence at positions from about 158 to about 360 of SEQ ID NO:2, or the DR5 intracellular domain encoded by the cDNA contained in ATCC Deposit No. 97920; (j) a nucleotide sequence that encodes the DR5 receptor extracellular and intracellular domains with all or part of the transmembrane domain deleted; (k) a nucleotide sequence that encodes the DR5 death domain comprising, or alternatively consisting of, the amino acid sequence at positions from about 273 to about 340 of SEQ ID NO:2, or the DR5 death domain encoded by the cDNA contained in ATCC Deposit No. 97920; (l) a nucleotide sequence that encodes a fragment of the polypeptide of (c) having DR5 functional activity (e.g., antigenic or biological activity); and (m) a nucleotide sequence complementary to any of the nucleotide sequences in (a), (b), (c), (d), (e), (f), (g), (h), (i), (j), (k), or (l) above. Polypeptides encoded by these polynucleotides are also encompassed by the invention.

By a polynucleotide having a nucleotide sequence at least, for example, 95% "identical" to a reference nucleotide sequence encoding a DR5 polypeptide is intended that the nucleotide sequence of the polynucleotide is identical to the reference sequence except that the polynucleotide sequence may include up to five mismatches per each 100 nucleotides of the reference nucleotide sequence encoding the DR5 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The reference (query) sequence may be the entire DR5 nucleotide sequence shown in FIGS. 1A–B (SEQ ID NO:1) or any polynucleotide fragment (e.g., a polynucleotide encoding the amino acid sequence of a DR5 N and/or C terminal deletion described herein) as described herein.

As a practical matter, whether any particular nucleic acid molecule is at least 80%, 85%, 90%, 92%, 95%, 96%, 97%, 98% or 99% identical to, for instance, the nucleotide sequence shown in SEQ ID NO:1 or to the nucleotide sequence of the deposited cDNA can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

In a specific embodiment, the identity between a reference (query) sequence (a sequence of the present invention) and a subject sequence. also referred to as a global sequence alignment, is determined using the FASTDB computer program based on the algorithm of Brutlag et al. (Comp. App. Biosci. 6:237–245 (1990)). Preferred parameters used in a FASTDB alignment of DNA sequences to calculate percent identity are: Matrix=Unitary, k-tuple=4, Mismatch Penalty= 1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

The present application is directed to nucleic acid molecules at least 80%, 85%, 90%, 92%, 95%, 96%, 97%, 98% or 99% identical to the nucleic acid sequence shown in SEQ ID NO:1, the nucleic acid sequence of the deposited cDNAs, or fragments thereof, irrespective of whether they encode a polypeptide having DR5 functional activity. This is because even where a particular nucleic acid molecule does not encode a polypeptide having DR5 functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having DR5 functional activity include, inter alia: (1) isolating the DR5 gene or allelic variants thereof in a cDNA library; (2) in situ hybridization (e.g., "FISH") to metaphase chromosomal spreads to provide precise chromosomal location of the DR5 gene, as described in Verma et al., *Human Chromosomes: A Manual of Basic Techniques*, Pergamon Press, New York (1988); and (3) Northern Blot analysis for detecting DR5 mRNA expression in specific tissues.

Preferred, however, are nucleic acid molecules having sequences at least 80%, 85%, 90%, 92%, 95%, 96%, 97%, 98% or 99% identical to the nucleic acid sequence shown in SEQ ID NO:1, the nucleic acid sequence of the deposited cDNAs, or fragments thereof, which do, in fact, encode a polypeptide having DR5 protein functional activity. By "a polypeptide having DR5 functional activity" is intended polypeptides exhibiting activity similar, but not necessarily identical, to a functional activity of the DR5 protein of the invention (either the full-length (i.e., complete) protein or, preferably, the mature protein), as measured in a particular biological assay. For example, DR5 polypeptide functional activity can be measured by the ability of a polypeptide sequence described herein to form multimers (e.g., homodimers and homotrimers) with complete DR5, and to bind a DR5 ligand (e.g., TRAIL). DR5 polypeptide functional activity can be also be measured, for example, by determining the ability of a polypeptide of the invention to induce apoptosis in cells expressing the polypeptide. These functional assays can be routinely performed using techniques described herein and otherwise known in the art.

For example, DR5 protein functional activity (e.g., biological activity) can be measured using the cell death assays performed essentially as previously described (A. M. Chinnaiyan, et al., *Cell* 81:505–12 (1995); M. P. Boldin, et al, *J Biol Chem* 270:7795–8 (1995); F. C Kischkel, et al, *EMBO* 14:5579–5588 (1995); A. M. Chinnaiyan, et al., J Biol Chem 271:4961–4965 (1996)) and as set forth in Example 5, below. In MCF7 cells, plasmids encoding full-length DR5 or a candidate death domain containing receptor are co-transfected with the pLantern reporter construct encoding green fluorescent protein. Nuclei of cells transfected with DR5 will exhibit apoptotic morphology as assessed by DAPI staining. Similar to TNFR-1 and Fas/APO-1 (M. Muzio, et al., *Cell* 85:817–827 (1996), M. P. Boldin, et al., *Cell* 85:803–815 (1996); M. Tewari, et al., *J Biol Chem* 270:3255–60 (1995)), DR5-induced apoptosis is preferably blocked by the inhibitors of ICE-like proteases, CrmA and z-VAD-fmk.

Of course, due to the degeneracy of the genetic code, one of ordinary skill in the art will immediately recognize that a large number of the nucleic acid molecules having a sequence at least 80%, 85%, 90%, 92%, 95%, 96%, 97%, 98% or 99% identical to for example, the nucleic acid sequence of the deposited cDNA, the nucleic acid sequence shown in SEQ ID NO:1, or fragments thereof, will encode a polypeptide "having DR5 protein functional activity." In fact, since degenerate variants of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having DR5 protein functional activity. This is because the skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that proteins are surprisingly tolerant of amino acid substitutions Polynucleotide Assays This invention is also related to the use of the DR5 polynucleotides to detect complementary polynucleotides such as, for example, as a diagnostic reagent. Detection of a mutated form of DR5 associated with a dysfunction will provide a diagnostic tool that can add or define a diagnosis of a disease or susceptibility to a disease which results from under-expression, over-expression, or altered expression of DR5 or a soluble form thereof, such as, for example, tumors or autoimmune disease.

Individuals carrying mutations in the DR5 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR prior to analysis. (Saiki et al., *Nature* 324:163–166 (1986)). RNA or cDNA may also be used in the same ways. As an example, PCR primers complementary to the nucleic acid encoding DR5 can be used to identify and analyze DR5 expression and mutations. For example, deletions and insertions can be detected by a change in size of the amplified product in comparison to the normal genotype. Point mutations can be identified by hybridizing amplified DNA to radiolabeled DR5 RNA or alternatively, radiolabeled DR5 antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science* 230:1242 (1985)).

Sequence changes at specific locations also may be revealed by nuclease protection assays, such as RNase and S1 protection or the chemical cleavage method (e.g., Cotton et al., *Proc. Natl Acad. Sci. USA* 85: 4397–4401 (1985)).

Thus, the detection of a specific DNA sequence may be achieved by methods which include, but are not limited to, hybridization, RNase protection, chemical cleavage, direct DNA sequencing or the use of restriction enzymes, (e.g., restriction fragment length polymorphisms ("RFLP") and Southern blotting of genomic DNA).

In addition to more conventional gel-electrophoresis and DNA sequencing, mutations also can be detected by in situ analysis.

Vectors and Host Cells

The present invention also relates to vectors which include DNA molecules of the present invention, host cells which are genetically engineered with vectors of the invention and the production of polypeptides of the invention by recombinant techniques.

Host cells can be genetically engineered to incorporate nucleic acid molecules and express polypeptides of the present invention. The polynucleotides may be introduced alone or with other polynucleotides. Such other polynucleotides may be introduced independently, co-introduced or introduced joined to the polynucleotides of the invention.

In accordance with this aspect of the invention the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate transacting factors either are supplied by the host, supplied by a complementing vector or supplied by the vector itself upon introduction into the host.

A great variety of expression vectors can be used to express a polypeptide of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The DNA sequence in the expression vector is operatively linked to appropriate expression control sequence(s)), including, for instance, a promoter to direct mRNA transcription. Representatives of such promoters include the phage lambda PL promoter, the *E. coli* lac, trp and tac promoters, the SV40 early and late promoters and promoters of retroviral LTRs, to name just a few of the well-known promoters. In general, expression constructs will contain sites for transcription, initiation and termination, and, in the transcribed region, a ribosome binding site for translation. The coding portion of the mature transcripts expressed by the constructs will include a translation initiating AUG at the beginning and a termination codon (UAA, UGA or UAG) appropriately positioned at the end of the polypeptide to be translated.

In addition, the constructs may contain control regions that regulate as well as engender expression. Generally, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Such markers include, but are not limited to, dihydrofolate reductase or neomycin resistance for eukaryotic cell culture, and tetracycline or ampicillin resistance genes for culturing *E. coli* and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors available to those of skill in the art.

Selection of appropriate vectors and promoters for expression in a host cell is a well known procedure and the requisite techniques for expression vector construction, introduction of the vector into the host and expression in the host are routine skills in the art.

The present invention also relates to host cells containing the above-described vector constructs described herein, and additionally encompasses host cells containing nucleotide sequences of the invention that are operably associated with one or more heterologous control regions (e.g., promoter and/or enhancer) using techniques known of in the art. The host cell can be a higher eukaryotic cell, such as a mammalian cell (e.g., a human derived cell), or a lower eukaryotic cell, such as a yeast cell, or the host cell can be a prokaryotic cell, such as a bacterial cell. The host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., phosphorylation, cleavage) of proteins. Appropriate cell lines can be chosen to ensure the desired modifications and processing of the foreign protein expressed.

Introduction of the construct into the host cell can be effected by calcium phosphate transfection, DEAE-dextran mediated transfection, cationic lipid-mediated transfection, electroporation, transduction, infection or other methods Such methods are described in many standard laboratory manuals, such as Davis et al., *Basic Methods in Molecular Biology* (1986).

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., DR5 coding sequence), and/or to include genetic material (e.g., heterologous polynucleotide sequences) that is operably associated with DR5 polynucleotides of the invention, and which activates, alters, and/or amplifies endogenous DR5 polynucleotides. For example, techniques known in the art may be used to operably associate heterologous control regions (e.g., promoter and/or enhancer) and endogenous DR5 polynucleotide sequences via homologous recombination (see, e.g., U.S. Pat. No. 5,641,670, issued Jun. 24, 1997; International Publication Number WO 96/29411, published Sep. 26, 1996; International Publication Number WO 94/12650, published Aug. 4, 1994; Koller et al., Proc. Natl. Acad. Sci. USA 86:8932–8935 (1989); and Zijlstra et al., *Nature*

342:435–438 (1989), the disclosures of each of which are incorporated by reference in their entireties).

The polypeptide may be expressed in a modified form, such as a fusion protein (comprising the polypeptide joined via a peptide bond to a heterologous protein sequence (of a different protein)), and may include not only secretion signals but also additional heterologous functional regions. Such a fusion protein can be made by ligating polynucleotides of the invention and the desired nucleic acid sequence encoding the desired amino acid sequence to each other, by methods known in the art, in the proper reading frame, and expressing the fusion protein product by methods known in the art. Alternatively, such a fusion protein can be made by protein synthetic techniques, e.g., by use of a peptide synthesizer. Thus, for instance, a region of additional amino acids, particularly charged amino acids, may be added to the N-terminus of the polypeptide to improve stability and persistence in the host cell, during purification or during subsequent handling and storage. Also, region also may be added to the polypeptide to facilitate purification. Such regions may be removed prior to final preparation of the polypeptide. For example, in one embodiment, polynucleotides encoding DR5 polypeptides of the invention may be fused to the pelB pectate lyase signal sequence to increase the efficiency to expression and purification of such polypeptides in Gram-negative bacteria. See, U.S. Pat. Nos. 5,576,195 and 5,846,818, the contents of which are herein incorporated by reference in their entireties.

Alternatively, such a fusion protein can be made by protein synthetic techniques, e.g., by use of a peptide synthesizer. Thus, for instance, a region of additional amino acids, particularly charged amino acids, may be added to the N-terminus of the polypeptide to improve stability and persistence in the host cell, during purification or during subsequent handling and storage. Additionally, a region also may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when the Fc portion proves to be a hindrance to use in therapy and diagnosis, for example when the fusion protein is to be used as an antigen for immunizations. In drug discovery, for example, human proteins, such as the hIL-5-receptor, have been fused with Fc portions for the purpose of high-throughput screening assays to identify antagonists of hIL-5. See, D. Bennett et al., *Journal of Molecular Recognition*, 8:52–58 (1995) and K. Johanson et al., *The Journal of Biological Chemistry*, 270:9459–9471 (1995).

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Transgenics and "Knock-outs"

The DR5 polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., nucleic acids of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (NY) 11:1263–1270 (1993); Wright et al., Biotechnology (NY) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:6148–6152 (1985)), blastocysts or embryos; gene targeting in embryonic stem cells (Thompson et al., *Cell* 56:313–321 (1989)); electroporation of cells or embryos (Lo, Mol Cell Biol. 3 1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, "Transgenic Animals," Intl. Rev. Cytol. 115:171–229 (1989), which is incorporated by reference herein in its entirety. See also, U.S. Pat. No. 5,464,764 (Capecchi, et al., Positive-Negative Selection Methods and Vectors); U.S. Pat. No. 5,631,153 (Capecchi, et al., Cells and Non-Human Organisms Containing Predetermined Genomic Modifications and Positive-Negative Selection Methods and Vectors for Making Same); U.S. Pat. No. 4,736,866 (Leder, et al., Transgenic Non-Human Animals); and U.S. Pat. No. 4,873,191 (Wagner, et al., Genetic Transformation of Zygotes); each of which is hereby incorporated by reference in its entirety. Further, the contents of each of the documents recited in this paragraph is herein incorporated by reference in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., *Nature* 380:64–66 (1996); Wilmut et al., *Nature* 385:810–813 (1997)), each of which is herein incorporated by reference in its entirety).

The present invention provides for transgenic animals that carry the transgene in all their cells, as well as animals which carry the transgene in some, but not all their cells, i.e., mosaic animals or chimeric animals. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Science 265:103–106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic and "knock-out" animals of the invention have uses which include, but are not limited to, animal model systems useful in elaborating the biological function of DR5 polypeptides, studying conditions and/or disorders associated with aberrant DR5 expression, and in screening for compounds effective in ameliorating such conditions and/or disorders.

In further embodiments of the invention, cells that are genetically engineered to express the proteins of the invention, or alternatively, that are genetically engineered not to express the proteins of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells, etc The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally. Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959, each of which is incorporated by reference herein in its entirety).

When the cells to be administered are non-autologous or non-MHC compatible cells, they can be administered using well known techniques which prevent the development of a host immune response against the introduced cells For example, the cells may be introduced in an encapsulated form which, while allowing for an exchange of components with the immediate extracellular environment, does not allow the introduced cells to be recognized by the host immune system.

DR5 Proteins and Fragments

The invention further provides for the proteins containing polypeptide sequences encoded by the polynucleotides of the invention.

The DR5 proteins of the invention may be in monomers or multimers (i. e., dimers, trimers, tetramers, and higher multimers). Accordingly, the present invention relates to monomers and multimers of the DR5 proteins of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only DR5 proteins of the invention (including DR5 fragments, variants, and fusion proteins, as described herein). These homomers may contain DR5 proteins having identical or different polypeptide sequences. In a specific embodiment, a homomer of the invention is a multimer containing only DR5 proteins having an identical polypeptide sequence. In another specific embodiment, a homomer of the invention is a multimer containing DR5 proteins having different polypeptide sequences. In specific embodiments, the multimer of the invention is a homodimer (e.g., containing DR5 proteins having identical or different polypeptide sequences) or a homotrimer (e.g., containing DR5 proteins having identical or different polypeptide sequences). In additional embodiments, the homomeric multimer of the invention is at least a homodimer, at least a homotrimer, or at least a homotetramer.

As used herein, the term heteromer refers to a multimer containing heterologous proteins (i.e., proteins containing only polypeptide sequences that do not correspond to a polypeptide sequences encoded by the DR5 gene) in addition to the DR5 proteins of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when proteins of the invention contact one another in solution. In another embodiment, heteromultimers of the invention, such as, for example, heterotrimers or heterotetramers, are formed when proteins of the invention contact antibodies to the polypeptides of the invention (including antibodies to the heterologous polypeptide sequence in a fusion protein of the invention) in solution. In other embodiments, multimers of the invention are formed by covalent associations with and/or between the DR5 proteins of the invention. Such covalent associations may involve one or more amino acid residues contained in the polypeptide sequence of the protein (e.g., the polypeptide sequence recited in SEQ ID NO:2 or the polypeptide encoded by the deposited cDNA). In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a DR5 fusion protein. In one example, covalent associations are between the heterologous sequence contained in a fusion protein of the invention (see, e.g., U.S. Pat. No. 5,478,925). In a specific example, the covalent associations are between the heterologous sequence contained in a DR5-Fc fusion protein of the invention (as described herein). In another specific example, covalent associations of fusion proteins of the invention are between heterologous polypeptide sequences from another TNF family ligand/receptor member that is capable of forming covalently associated multimers, such as for example, oseteoprotegerin (see, e.g., International Publication No. WO 98/49305, the contents of which are herein incorporated by reference in its entirety). In another embodiment, two or more DR5 polypeptides of the invention are joined through synthetic linkers (e.g., peptide, carbohydrate or soluble polymer linkers). Examples include, but are not limited to, those peptide linkers described in U.S. Pat. No. 5,073,627 (hereby incorporated by reference). Proteins comprising multiple DR5 polypeptides separated by peptide linkers may be produced using conventional recombinant DNA technology.

Another method for preparing multimer DR5 polypeptides of the invention involves use of DR5 polypeptides fused to a leucine zipper or isoleucine zipper polypeptide sequence. Leucine zipper domains and isoleucine zipper domains are polypeptides that promote multimerization of the proteins in which they are found. Leucine zippers were originally identified in several DNA-binding proteins (Landschulz et al., *Science* 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric DR5 proteins are those described in PCT application WO 94/10308, hereby incorporated by reference. Recombinant fusion proteins comprising a soluble DR5 polypeptide fused to a peptide that dimerizes or trimerizes in solution are expressed in suitable host cells, and the resulting soluble multimeric DR5 is recovered from the culture supernatant using techniques known in the art.

Certain members of the TNF family of proteins are believed to exist in trimeric form (Beutler and Huffel, *Science* 264:667, 1994; Banner et al., *Cell* 73:431 (1993)). Thus, trimeric DR5 may offer the advantage of enhanced biological activity. Preferred leucine zipper moieties are those that preferentially form trimers. One example is a leucine zipper derived from lung surfactant protein D (SPD), as described in Hoppe et al. (*FEBS Letters* 344:191, (1994)) and in U.S. patent application Ser. No. 08/446,922, hereby incorporated by reference. Other peptides derived from naturally occurring trimeric proteins may be employed in preparing trimeric DR5.

In another example, proteins of the invention are associated by interactions between Flag® polypeptide sequence contained in Flag®R-DR5 or Flag®-DR5 fusion proteins of the invention. In a further embodiment, associations proteins of the invention are associated by interactions between heterologous polypeptide sequence contained in Flag®-DR5 or Flag®-DR5 fusion proteins of the invention and anti-Flag® antibody.

The multimers of the invention may be generated using chemical techniques known in the art. For example, proteins desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the polypeptide sequence of the proteins desired to be contained in the multimer (see, e.g., U.S. Pat. No. 5,478,925, which is herein incorporated by reference in its entirety).

Further, proteins of the invention may be routinely modified by the addition of cysteine or biotin to the C-terminus or N-terminus of the polypeptide sequence of the protein and techniques known in the art may be applied to generate multimers containing one or more of these modified proteins (see, e.g., U.S. Pat. No. 5,478,925, which is herein incorporated by reference in its entirety). Additionally, techniques known in the art may be applied to generate liposomes containing the protein components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, proteins contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain and which can be incorporated by membrane reconstitution techniques into liposomes (see, e.g., U.S. Pat. No. 5,478,925, which is herein incorporated by reference in its entirety).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the DR5 polypeptide can be substantially purified by the one-step method described in Smith and Johnson, Gene 67:31–40 (1988).

In one embodiment, the invention provides an isolated DR5 polypeptide having the amino acid sequence encoded by the deposited cDNA, or the amino acid sequence in SEQ ID NO:2, or a polypeptide or peptide comprising, or alternatively consisting of, a portion (i.e., fragment) of the above polypeptides. Polynucleotides encoding these polypeptides are also encompassed by the invention.

Polypeptide fragments of the present invention include polypeptides comprising, or alternatively consisting of, an amino acid sequence contained in SEQ ID NO:2, encoded by the cDNA contained in the deposited plasmid, or encoded by nucleic acids which hybridize (e.g., under stringent hybridization conditions) to the nucleotide sequence contained in the deposited plasmid, or shown in FIGS. 1A–B (SEQ ID NO:1) or the complementary strand thereto. Protein fragments may be "free-standing," or comprised within a larger polypeptide of which the fragment forms a part or region, most preferably as a single continuous region. Representative examples of polypeptide fragments of the invention, include, for example, fragments that comprise, or alternatively consist of, a member selected from the group consisting of from about amino acid residues –51 to –1, 1 to 27, 28 to 40, 41 to 60, 61 to 83, 84 to 100, 101 to 127, 128 to 133, 134 to 157, 158 to 167, 168 to 180, 181 to 200, 201 to 220, 221 to 240, 241 to 260, 261 to 272, 273 to 310, 311 to 340, and 341 to 360 of SEQ ID NO:2, as well as isolated polynucleotides which encode these polypeptides. Additional representative examples of polypeptide fragments of the invention, include, for example, fragments that comprise, or alternatively consist of, a member selected from the group consisting of from about amino acid residues 1–60, 11–70, 21–80, 31–90, 41–100, 51–110, 61–120, 71–130, 81–140, 91–150, 101–160, 111–170, 121–180, 131–190, 141–200, 151–210, 161–220, 171–230, 181–240, 191–250, 201–260, 211–270, 221–280, 231–290, 241–300, 251–310, 261–320, 271–330, 281–340, 291–350, and 301–360 of SEQ ID NO:2, as well as isolated polynucleotides which encode these polypeptides.

Moreover, polypeptide fragments can be at least about 10, 20, 30, 40, 50, 60, 70, 80, 90, 100, 110, 120, 130, 140, or 150 amino acids in length. In this context "about" includes the particularly recited value, larger or smaller by several (5, 4, 3, 2, or 1) amino acids, at either extreme or at both extremes. Polynucleotides encoding these polypeptides are also encompassed by the invention.

Preferred polypeptide fragments of the present invention include a polypeptide comprising, or alternatively consisting of, one, two, three, four, five or more amino acid sequences selected from the group consisting of: a polypeptide comprising, or alternatively consisting of, the DR5 receptor extracellular domain (predicted to constitute amino acid residues from about 1 to about 133 in SEQ ID NO:2); a polypeptide comprising, or alternatively consisting of, the DR5 cysteine rich domain (predicted to constitute amino acid residues from about 33 to about 128 in SEQ ID NO:2), a polypeptide comprising, or alternatively consisting of, the DR5 receptor transmembrane domain (predicted to constitute amino acid residues from about 134 to about 157 in SEQ ID NO:2); a polypeptide comprising, or alternatively consisting of, fragment of the predicted mature DR5 polypeptide, wherein the fragment has a DR5 functional activity (e.g., antigenic activity or biological activity); a polypeptide comprising, or alternatively consisting of, the DR5 receptor intracellular domain (predicted to constitute amino acid residues from about 158 to about 360 in SEQ ID NO:2); a polypeptide comprising, or alternatively consisting of, the DR5 receptor extracellular and intracellular domains with all or part of the transmembrane domain deleted; a polypeptide comprising, or alternatively consisting of, the DR5 receptor death domain (predicted to constitute amino acid residues from about 273 to about 340 in SEQ ID NO:2); and a polypeptide comprising, or alternatively consisting of, one, two, three, four or more epitope bearing portions of the DR5 receptor protein. In additional embodiments, the polypeptide fragments of the invention comprise, or alternatively consist of, any combination of 1, 2, 3, 4, 5, 6, 7, or all 8 of the above members. As above, with the leader sequence, the amino acid residues constituting the DR5 receptor extracellular, transmembrane and intracellular domains have been predicted by computer analysis. Thus, as one of ordinary skill would appreciate, the amino acid residues constituting these domains may vary slightly (e.g., by about 1 to about 15 amino acid residues) depending on the criteria used to define each domain. Polynucleotides encoding these polypeptides are also encompassed by the invention.

As discussed above, it is believed that one or both of the extracellular cysteine-rich motifs of DR5 is important for interactions between DR5 and its ligands. Accordingly, in preferred embodiments, polypeptide fragments of the invention comprise, or alternatively consist of, amino acid residues 33 to 80, and/or 81 to 128 of SEQ ID NO:2. In a specific embodiment the polypeptides of the invention comprise, or alternatively consist of, both of the extracellular cysteine-rich motifs disclosed in SEQ ID NO:2. Polynucleotides encoding these polypeptides are also encompassed by the invention.

Among the especially preferred fragments of the invention are fragments comprising, or alternatively consisting of, structural or functional attributes of DR5. Such fragments include amino acid residues that comprise, or alternatively consisting of, one, two, three, four or more of the following functional domains: alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophillic regions, hydrophobic regions, alpha amphipathic regions, beta amphipathic regions, surface forming regions, and high antigenic index regions (i.e., regions of polypeptides consisting of amino acid residues having an antigenic index of or equal to greater than 1.5, as identified using the default parameters of the Jameson-Wolf program) of DR5.

Certain preferred regions are those disclosed in FIG. 3 and Table I and include, but are not limited to, regions of the aforementioned types identified by analysis of the amino acid sequence depicted in FIGS. 1A–B, such preferred regions include; Garnier-Robson predicted alpha-regions, beta-regions, turn-regions, and coil-regions; Chou-Fasman predicted alpha-regions, beta-regions, and turn-regions; Kyte-Doolittle predicted hydrophilic regions and Hopp-Woods predicted hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

In another aspect, the invention provides a peptide or polypeptide comprising, or alternatively consisting of, one, two, three, four, five or more epitope-bearing portions of a polypeptide of the invention. The epitope of this polypeptide portion is an immunogenic or antigenic epitope of a polypeptide described herein Polynucleotides encoding these polypeptides are also encompassed by the invention.

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, J. G. Sutcliffe et al., "Antibodies That React With Predetermined Sites on Proteins," *Science* 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767–778 (1984) at 777. Antigenic epitope-bearing peptides and polypeptides of the invention preferably contain a sequence of at least seven, more preferably at least nine and most preferably between at least about 15 to about 30 amino acids contained within the amino acid sequence of a polypeptide of the invention. In the present invention, antigenic epitopes preferably contain a sequence of at least 4, at least 5, at least 6, at least 7, more preferably at least 8, at least 9, at least 10, at least 15, at least 20, at least 25, and, most preferably, between about 15 to about 30 amino acids. Preferred polypeptides comprising, or alternatively consisting of, immunogenic or antigenic epitopes are at least 10, 15, 20, 25, 30, 35, 40, 45, 50, 55, 60, 65, 70, 75, 80, 85, 90, 95, or 100 amino acid residues in length. Polynucleotides encoding these polypeptides are also encompassed by the invention Antigenic epitopes are useful, for example, to raise antibodies, including monoclonal antibodies, that specifically bind the epitope. Further, antigenic epitopes can be used as the target molecules in immunoassays. (See, for instance, Wilson et al., *Cell* 37:767–778 (1984); Sutcliffe et al, *Science* 219:660–666 (1983)).

Non-limiting examples of antigenic polypeptides or peptides that can be used to generate DR5 receptor-specific antibodies include: a polypeptide comprising, or alternatively consisting of, amino acid residues from about 11 to about 59 in SEQ ID NO:2, from about 68 to about 113 in SEQ ID NO:2, from about 173 to about 220 in SEQ ID NO:2, and from about 224 to about 319 in SEQ ID NO:2. In this context "about" includes the particularly recited ranges, larger or smaller by several (5, 4, 3, 2, or 1) amino acid residues, at either terminus or at both termini. As indicated above, the inventors have determined that the above polypeptide fragments are antigenic regions of the DR5 receptor protein. Polynucleotides encoding these polypeptides are also encompassed by the invention.

The epitope-bearing peptides and polypeptides of the invention may be produced by any conventional means. R. A. Houghten, "General Method for the Rapid Solid-Phase Synthesis of Large Numbers of Peptides: Specificity of Antigen-Antibody Interaction at the Level of Individual Amino Acids," *Proc. Natl. Acad. Sci. USA* 82:5131–5135 (1985). This "Simultaneous Multiple Peptide Synthesis (SMPS)" process is further described in U.S. Pat. No. 4,631,211 to Houghten et al. (1986).

Immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). A preferred immunogenic epitope includes the secreted protein. The polypeptides comprising one or more immunogenic epitopes may be presented for eliciting an antibody response together with a carrier protein, such as an albumin, to an animal system (such as, for example, rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as, for example, rabbits, rats, and mice are immunized with either free or carrier-coupled peptides, for instance, by intraperitoneal and/or intradermal injection of emulsions containing about 100 micrograms of peptide or carrier protein and Freund's adjuvant or any other adjuvant known for stimulating an immune response. Several booster injections may be needed, for instance, at intervals of about two weeks, to provide a useful titer of anti-peptide antibody that can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, DR5 receptor polypeptides of the present invention and the epitope-bearing fragments thereof described herein (e.g., corresponding to a portion of the extracellular domain, such as, for example, amino acid residues 1 to 133 of SEQ ID NO:2) can be combined with heterologous polypeptide sequences. For example, the polypeptides of the present invention may be fused with the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life. This has been shown, e.g., for chimeric proteins consisting of the first two domains of the human CD4-polypeptide and various domains of the constant regions of the heavy or light chains of mammalian immunoglobulins (EPA 394,827; Traunecker et al, *Nature* 331:84–86 (1988)). Fusion proteins that have a disulfide-linked dimeric structure due to the IgG part can also be more efficient in binding and neutralizing other molecules than the monomeric DR5 protein or protein fragment alone (Fountoulakis et al., *J. Biochem.* 270:3958–3964(1995)). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues. The tag serves as a matrix-binding domain for the fusion protein. Extracts from cells infected with the recombinant vaccinia virus are loaded onto $Ni^{2+}$ nitriloacetic acid-agarose column and histidine-tagged proteins can be selectively eluted with imidazole-containing buffers. Polynucleotides encoding these fusion proteins are also encompassed by the invention.

The techniques of gene-shuffling, motif-shuffling, exon-shuffling, and/or codon-shuffling (collectively referred to as "DNA shuffling") may be employed to modulate the activities of DR5 thereby effectively generating agonists and antagonists of DR5. See generally, U.S. Pat. Nos. 5,605,793, 5,811,238, 5,830,721, 5,834,252, and 5,837,458, and Patten, P. A., et al., *Curr. Opinion Biotechnol.* 8:724–33 (1997); Harayama, S. *Trends Biotechnol.* 16(2):76–82 (1998); Hansson, L. O., et al, *J. Mol. Biol.* 287:265–76 (1999); and Lorenzo, M. M. and Blasco, R. *BioTechniques* 24(2):308–13 (1998) (each of these patents and publications are hereby incorporated by reference). In one embodiment, alteration of DR5 polynucleotides and corresponding polypeptides may be achieved by DNA shuffling. DNA shuffling involves the assembly of two or more DNA segments into a desired DR5 molecule by homologous, or site-specific, recombination. In another embodiment, DR5 polynucleotides and corresponding polypeptides may be altered by being subjected to random mutagenesis by error-prone PCR, random nucleotide insertion or other methods prior to recombination.

In another embodiment, one or more components, motifs, sections, parts, domains, fragments, etc., of DR5 may be recombined with one or more components, motifs, sections, parts, domains, fragments, etc. of one or more heterologous molecules. In preferred embodiments, the heterologous molecules are, for example, TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4–1BBL, DcR3, OX40L, TNF-gamma (International Publication No. WO 96/14328), AIM-I (International Publication No. WO 97/33899), AIM-II (International Publication No. WO 97/34911), APRIL (J. Exp. Med. 188(6):1185–1190), endokine-alpha (International Publication No. WO 98/07880), Neutrokine-alpha (International Publication No. WO 98/18921), OPG, nerve growth factor (NGF), DR3 (International Publication No. WO 97/33904), DR4 (International Publication No. WO 98/32856), TR5 (International Publication No. WO 98/30693), TR6 (International Publication No. WO 98/30694), TRANK, TR9 (International Publication No. WO 98/56892), TR10 (International Publication No. WO 98/54202),3 12C2 (International Publication No. WO 98/06842), TR12, TNF-R1, TRAMP/DR3/APO-3/WSL/LARD, TRAIL-R1/DR4/APO-2, TRAIL-R2/DR5, DcR1/TRAIL-R3/TRID/LIT, DcR2/TRAIL-R4, CAD, TRAIL, TRAMP, and v-FLIP. In additional preferred embodiments, the heterologous molecules are, for example, soluble forms of Fas, CD30, CD27, CD40 and 4-IBB.

In further preferred embodiments, the heterologous molecules are any member of the TNF family.

To improve or alter the characteristics of DR5 polypeptides, protein engineering may be employed. Recombinant DNA technology known to those skilled in the art can be used to create novel mutant proteins or "muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

For instance, for many proteins, including the extracellular domain of a membrane associated protein or the mature form(s) of a secreted protein, it is known in the art that one or more amino acids may be deleted from the N-terminus or C-terminus without substantial loss of biological function. However, even if deletion of one or more amino acids from the N-terminus or C-terminus of a protein results in modification or loss of one or more biological functions of the protein, other DR5 functional activities may still be retained. For example, in many instances, the ability of the shortened protein to induce and/or bind to antibodies which recognize DR5 (preferably antibodies that bind specifically to DR5) will retained irrespective of the size or location of the deletion. In fact, polypeptides composed of as few as six DR5 amino acid residues may often evoke an immune response. Whether a particular polypeptide lacking N-terminal and/or C-terminal residues of a complete protein retains such immunologic activities can readily be determined by routine methods described herein and otherwise known in the art.

As mentioned above, even if deletion of one or more amino acids from the N-terminus of a protein results in modification or loss of one or more biological functions of the protein, other functional activities (e.g., biological activities, ability to multimerize, ability to bind DR5 ligand) may still be retained. For example, the ability of shortened DR5 muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a DR5 mutein with a large number of deleted N-terminal amino acid residues may retain some biological or immunogenic activities.

It will be recognized in the art that some amino acid sequence of DR5 can be varied without significant effect on the structure or function of the protein. If such differences in sequence are contemplated, it should be remembered that there will be critical areas on the protein which determine activity. Such areas will usually comprise residues which make up the ligand binding site or the death domain, or which form tertiary structures which affect these domains.

Accordingly, the present invention further provides polypeptides having one or more residues deleted from the amino terminus of the DR5 amino acid sequence shown in FIGS. 1A–B, up to the alanine residue at position number 406 and polynucleotides encoding such polypeptides. In particular, the present invention provides polypeptides comprising, or alternatively consisting of, the amino acid sequence of residues $n^1$-411 of FIGS. 1A–B where $n^1$ is an integer from 2 to 406 corresponding to the position of the amino acid residue in FIGS. 1A–B (which is identical to the sequence shown as SEQ ID NO:2, with the exception that the amino acid residues in FIGS. 1A–B are numbered consecutively from 1 through 411 from the N-terminus to the C-terminus, while the amino acid residues in SEQ ID NO:2 are numbered consecutively from –51 through 360 to reflect the position of the predicted signal peptide).

More in particular, the invention provides polynucleotides encoding polypeptides comprising, or alternatively consisting of, the amino acid sequence of a member selected from the group consisting of residues: E-2 to S-411; Q-3 to S-411; R-4 to S-411; G-5 to S-411; Q-6 to S-411; N-7 to S-411; A-8 to S-411; P-9 to S-411; A-10 to S-411; A-11 to S-411; S-12 to S-411; G-13 to S-411; A-14 to S-411; R-15 to S-411; K-16 to S-411; R-17 to S-411; H-18 to S-411; G-19 to S-411; P-20 to S-411; G-21 to S-411; P-22 to S-411; R-23 to S-411; E-24 to S-411; A-25 to S-411; R-26 to S-411; G-27 to S-411; A-28 to S-411; R-29 to S-411; P-30 to S-411; G-31 to S-411; P-32 to S-411; R-33 to S-411; V-34 to S-411; P-35 to S-411; K-36 to S-411; T-37 to S-411; L-38 to S-411; V-39 to S-411; L-40 to S-411; V-41 to S-411; V-42 to S-411; A-43 to S-411; A44 to S-411; V-45 to S-411; L-46 to S-411; L-47 to S-411; L-48 to S-411; V-49 to S-411; S-50 to S-411; A-51 to S-411; E-52 to S-411; S-53 to S-411; A-54 to S-411; L-55 to S-411; I-56 to S-411; T-57 to S-411; Q-58 to S-411; Q-59 to S-411; D-60 to S-411; L-61 to S-411; A-62 to S-411; P-63 to S-411; Q-64 to S-411; Q-65 to S-411; R-66 to S-411; A-67 to S-411; A-68 to S-411; P-69 to S-411; Q-70 to S-411; Q-71 to S-411; K-72 to S-411; R-73 to S-411; S-74 to S-411; S-75 to S-411; P-76 to S-411; S-77 to S-411; E-78 to S-411; G-79 to S-411; L-80 to S-411; C-81 to S-411; P-82 to S-411; P-83 to S-411; G-84 to S-411; H-85 to S-411; H-86 to S-411; I-87 to S-411; S-88 to S-411; E-89 to S-411; D-90 to S-411; G-91 to S-411; R-92 to S-411; D-93 to S-411; C-94 to S-411; I-95 to S-411; S-96 to S-411; C-97 to S-411; K-98 to S-411; Y-99 to S-411; G-100 to S-411; Q-101 to S-411; D-102 to S-411; Y-103 to S-411; S-104 to S-411; T-105 to S-411; H-105 to S-411; F-112 to S-411; C-113 to S-411; L-114 to S-411; R-115 to S-411; C-116 to S-411; T-117 to S-411; R-118 to S-411; C-119 to S-411; D-120 to S-411; S-121 to S-411; G-122 to S-411; E-123 to S-411; V-124 to S-411; E-125 to S-411; L-126 to S-411; S-127 to S-411; P-128 to S-411; C-129to S-411; T-130 to S-411; T-131 to S-411; T-132 to S-411; R-133 to S-411; N-134 to S-411; T-135 to S-411; V-136 to S-411; C-137 to S-411; Q-138 to S-411; C-139 to S-411; E-140 to S-411; E-141 to S-411; G-142 to S-411; T-143 to S-411; F-144 to S-411; R-145 to S-411; E-146 to S-411; E-147 to S-411 D-148 to S-411; S-149 to S-411; P-150 to S-411; E-151 to S-411; M-152 to S-411; C-153 to S-411; R-154 to S-411; K-155 to S-411; C-156 to S-411; R-157 to S-411; T-158 to S-411; G-159 to S-411; C-160 to S-411; P-161 to S-411; R-162 to S-411; G-163 to S-411; M-164 to S-411; V-165 to S-411; K-166 to S-411; V-167 to S-411; G-168 to S-411; D-169 to S-411; C-170 to S-411; T-171 to S-411; P-172 to S-411; W-173 to S-411; S-174 to S-411; D-175 to S-411; I-176 to S-411; E-177 to S-411; C-178 to S-411; V-179 to S-411; H-180 to S-411; K-181 to S-411; E-182 to S-411; S-183 to S-411; G-184 to S-411; I-185 to S-411; I-186 to S-411; I-187 to S-411; G-188 to S-411; V-189 to S-411; T-190 to S-411; V-191 to S-411; A-192 to S-411; A-193 to S-411; V-194to S-411; V-195 to S-411; L-196 to S-411; I-197 to S-411; V-198 to S-411; A-199 to S-411; V-200 to S-411; F-201 to S-411; V-202 to S-411; C-203 to S-411; K-204 to S-411; S-205 to S-411; L-206 to S-411; L-207 to S-411; W-208 to S-411; K-209 to S-411; K-210 to S-411; V-211 to S-411; L-212 to S-411; P-213 to S-411; Y-214to S-411; L-215 to S-411; K-216 to S-411; G-217 to S-411; I-218 to S-411; C-219 to S-411; S-220 to S-411; G-221 to S-411; G-222 to S-411; G-223 to S-411; G-224 to S-411; D-225 to S-411; P-226 to S-411; E-227 to S-411; R-228 to S-411; V-229 to S-411; D-230 to S-411; R-231 to S-411; S-232 to S-411; S-233 to S-411; Q-234 to S-411; R-235 to S-411; P-236 to S-411; G-237 to S-411; A-238 to S-411; E-239 to S-411; D-240 to S-411; N-241 to S-411; V-242 to S-411; L-243 to S-411; N-244 to S-411; E-245 to S-411; I-246 to S-411 V-247 to S-411; S-248 to S-411; I-249 to S-411; L-250 to S-411; Q-251 to S-411; P-252 to S-411; T-253 to S-411; Q-254 to S-411; V-255 to S-411; P-256 to S-411; E-257 to S-411; Q-258 to S-411; E-259 to S-411; M-260 to S-411; E-261 to S-411; V-262 to S-411; Q-263 to S-411; E-264 to S-411; P-265 to S-411; A-266 to S-411; E-267 to S-411; P-268to S-411; T-269to S-411; G-270 to S-411; V-271 to S-411; N-272 to S-411; M-273 to S-411; L-274 to S-411; S-275 to S-411; P-276 to S-411; G-277 to S-411; E-278 to S-411; S-279 to S-411; E-280 to S-411; H-281 to S-411; L-282 to S-411; L-283 to S-411; E-284 to S-411; P-285 to S-411; A-286 to S-411; E-287 to S-411; A-288 to S-411; E-289 to S-411; R-290 to S-411; S-291 to S-411; Q-292 to S-411; R-293 to S-411; R-294 to S-411; R-295 to S-411; L-296 to S-411; L-297 to S-411; V-298 to S-411; P-299 to S-411; A-300 to S-411; N-301 to S-411; E-302 to S-411; G-303 to S-411; D-304 to S-411; P-305 to S-411; T-306 to S-411; E-307 to S-411; T-308 to S-411; L-309 to S-411; R-310 to S-411; Q-311 to S-411; C-312 to S-411; F-313 to S-411; D-314 to S-411; D-315 to S-411; F-316 to S-411; A-317 to S-411; D-318 to S-411; L-319 to S-411; V-320 to S-411; P-321 to S-411; F-322 to S-411; D-323 to S-411; S-324 to S-411; W-325 to S-411; E-326 to S-411; P-327 to S-411; L-328 to S-411; M-329 to S-411; R-330 to S-411; K-331 to S-411; L-332 to S-411; G-333 to S-411; L-334 to S-411; M-335 to S-411; D-336 to S-411; N-337 to S-411; E-338 to S-411; I-339 to S-411; K-340 to S-411; V-341 to S-411; A-342 to S-411; K-343 to S-411; A-344 to S-411; E-345 to S-411; A-346 to S-411; A-347 to S-411; G-348 to S-411; H-349 to S-411; R-350 to S-411; D-351 to S-411; T-352 to S-411; L-353 to S-411; Y-354 to S-411; T-355 to S-411; M-356 to S-411; L-357 to S-411; I-358 to S-411; K-359 to S-411; W-360 to S-411; V-361 to S-411; N-362 to S-411; K-363 to S-411; T-364 to S-411; G-365 to S-411; R-366 to S-411; D-367 to S-411; A-368 to S-411; S-369 to S-411; V-370 to S-411; H-371 to S-411; T-372 to S-411; L-373 to S-411; L-374 to S-411; D-375 to S-411; A-376 to S-411; L-377 to S-411; E-378to S-411; T-379to S-411; L-380to S-411; G-381 to S-411; E-382 to S-411; E-383 to S-411; L-383 to S-411; A-385 to S-411; A-386 to S-411; Q-387 to S-411; K-388 to S-411; I-389 to S-411; E-390 to S-411; D-391 to S-411;

H-392 to S-411; L-393 to S-411; L-394 to S-411; S-395 to S-411; S-396 to S-411; G-397 to S-411; K-398 to S-411; F-399 to S-411; M-400 to S-411; Y-401 to S-411; L-402 to S-411; E-403 to S-411; G-404 to S-411; N-405 to S-411; and A-406 to S-411 of the DR5 sequence shown in FIGS. 1A–B (which is identical to the sequence shown as SEQ ID NO:2, with the exception that the amino acid residues in FIGS. 1A–B are numbered consecutively from 1 through 411 from the N-terminus to the C-terminus, while the amino acid residues in SEQ ID NO:2 are numbered consecutively from −51 through 360 to reflect the position of the predicted signal peptide).

The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The invention is further directed to nucleic acid molecules comprising, or alternatively consisting of, polynucleotide sequences which encode polypeptides that are at least 80%, 85%, 90%, 92%, 95%, 96%, 97%, 98%, or 99% identical to the polypeptides described above. The present invention also encompasses the above polynucleotide sequences fused to a heterologous polynucleotide sequence. Polypeptides encoded by these polynucleotides are also encompassed by the invention.

In another embodiment, N-terminal deletions of the DR5 polypeptide can be described by the general formula $n^2$ to 184 where $n^2$ is a number from 1 to 179 corresponding to the amino acid sequence identified in FIGS. 1A–B (or where $n^2$ is a number from −51 to 128 corresponding to the amino acid sequence identified in SEQ ID NO:2). In specific embodiments, N-terminal deletions of the DR5 of the invention comprise, or alternatively consist of, a member selected from the group consisting of amino acid residues: E-2 to G-184; Q-3 to G-184; R-4 to G-184; G-5 to G-184; Q-6 to G-184; N-7 to G-184; A-8 to G-184; P-9 to G-184; A-10 to G-184; A-11 to G-184; S-12 to G-184; G-13 to G-184; A-14 to G-184; R-15 to G-184; K-16 to G-184; R-17 to G-184; H-18 to G-184; G-19 to G-184; P-20 to G-184; G-21 to G-184; P-22 to G-184; R-23 to G-184; E-24 to G-184; A-25 to G-184; R-26 to G-184; G-27 to G-184; A-28 to G-184; R-29 to G-184; P-30 to G-184; G-31 to G-184; P-32 to G-184; R-33 to G-184; V-34 to G-184; P-35 to G-184; K-36 to G-184; T-37 to G-184; L-38 to G-184; V-39 to G-184; L-40 to G-184; V-41 to G-184; V-42 to G-184; A-43 to G-184; A-44 to G-184; V-45 to G-184; L-46 to G-184; L-47 to G-184; L-48 to G-184; V-49 to G-184; S-50 to G-184; A-51 to G-184; E-52 to G-184; S-53 to G-184; A-54 to G-184; L-55 to G-184; I-56 to G-184; T-57 to G-184; Q-58 to G-184; Q-59 to G-184; D-60 to G-184; L-61 to G-184; A-62 to G-184; P-63 to G-184; Q-64 to G-184; Q-65 to G-184; R-66 to G-184; A-67 to G-184; A-68 to G-184; P-69 to G-184; Q-70 to G-184; Q-71 to G-184; K-72 to G-184; R-73 to G-184; S-74 to G-184; S-75 to G-184; P-76 to G-184; S-77 to G-184; E78 to G-184; G-79 to G-184; L-80 to G-184; C-81 to G-184; P-82 to G-184; P-83 to G-184; G-84 to G-184; H-85 to G-184; H-86 to G-184; I-87 to G-184; S-88 to G-184; E-89 to G-184; D-90 to G-184; G-91 to G-184; R-92 to G-184; D-93 to G-184; C-94 to G-184; I-95 to G-184; S-96 to G-184; C-97 to G-184; K-98 to G-184; Y-99 to G-184; G-100 to G-184; Q-101 to G-184; D-102 to G-184; Y-103 to G-184; S-104 to G-184; T-105 to G-184; H-106 to G-184; W-107 to G-184; N-108 to G-184; D-109 to G-184; L-110 to G-184; L-111 to G-184; F-112 to G-184; C-113 to G-184; L-114 to G-184; R-115 to G-184; C-116 to G-184; T-117 to G-184; R-118 to G-184; C-119 to G-184; D-120 to G-184; S-121 to G-184; G-122 to G-184; E-123 to G-184; V-124 to G-184; E-125 to G-184; L-126 to G-184; S-127 to G-184; P-128 to G-184; C-129 to G-184; T-130 to G-184; T-131 to G-184; T-132 to G-184; R-133 to G-184; N-134 to G-184; T-135 to G-184; V-136 to G-184; C-137 to G-184; Q-138 to G-184; C-139 to G-184; E-140 to G-184; E-141 to G-184; G-142 to G-184; T-143 to G-184; F-144 to G-184; R-145 to G-184; E-146 to G-184; E-147 to G-184; D-148 to G-184; S-149 to G-184; P-150 to G-184; E-151 to G-184; M-152 to G-184; C-153 to G-184; R-154 to G-184; K-155 to G-184; C-156 to G-184; R-157 to G-184; T-158 to G-184; G-159 to G-184; C-160 to G-184; P-161 to G-184; R-162 to G-184; G-163 to G-184; M-164 to G-184; V-165 to G-184; K-166 to G-184; V-167 to G-184; G-168 to G-184; D-169 to G-184; C-170 to G-184; T-171 to G-184; P-172 to G-184; W-173 to G-184; S-174 to G-184; D-175 to G-184; I-176 to G-184; E-177 to G-184; C-178 to G-184; and V179 to G184 of the DR5 extracellular domain sequence shown$^2$ in FIGS. 1A–B (which is identical to the sequence shown as SEQ ID NO:2, with the exception that the amino acid residues in FIGS. 1A–B are numbered consecutively from 1 through 411 from the N-terminus to the C-terminus, while the amino acid residues in SEQ ID NO:2 are numbered consecutively from −51 through 360 to reflect the position of the predicted signal peptide).

The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The invention is further directed to nucleic acid molecules comprising, or alternatively consisting of, polynucleotide sequences which encode polypeptides that are at least 80%, 85%, 90%, 92%, 95%, 96%, 97%, 98%, or 99% identical to the polypeptides described above. The present invention also encompasses the above polynucleotide sequences fused to a heterologous polynucleotide sequence. Polypeptides encoded by these polynucleotides are also encompassed by the invention.

Also as mentioned above, even if deletion of one or more amino acids from the C-terminus of a protein results in modification of loss of one or more biological functions of the protein, other functional activities (e.g., biological activities, ability to multimerize, ability to bind DR5 ligand (e.g., TRAIL)) may still be retained. For example, the ability of the shortened DR5 mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a DR5 mutein with a large number of deleted C-terminal amino acid residues may retain some biological or immunogenic activities. In fact, peptides composed of as few as six DR5 amino acid residues may often evoke an immune response.

Accordingly, the present invention further provides polypeptides having one or more residues deleted from the carboxy terminus of the amino acid sequence of the DR5 polypeptide shown in FIGS. 1A–B (SEQ ID NO:2), up to the glutamic acid residue at position number 52, and polynucleotides encoding such polypeptides. In particular, the present invention provides polypeptides comprising, or alternatively consisting of, the amino acid sequence of residues 52-$m^1$ of FIGS. 1A–B (i.e., SEQ ID NO:2), where $m^1$ is an integer from 57 to 410 corresponding to the position of the amino acid residue in FIGS. 1A–B (or where $m^1$ is an integer from 6 to 360 corresponding to the position of the amino acid residue in SEQ ID NO:2). More in particular, the invention provides polynucleotides encoding polypeptides comprising, or alternatively consisting of, a member selected from the group consisting of residues: E-52 to M-410; E-52 to A-409; E-52 to S-408; E-52 to D-407; E-52 to A-406; E-52 to N-405; E-52 to G-404; E-52 to E-403; E-52 to L-402; E-52 to Y-401; E-52 to M-400; E-52 to F-399; E-52 to K-398 E-52 to G-397; E-52 to S-396; E-52 to S-395; E-52 to L-394; E-52 to L-393; E-52 to H-392; E-52 to D-391; E-52 to E-390; E-52 to I-389; E-52 to K-388; E-52 to Q-387; E-52 to K-386; E-52 to A-385; E-52 to L-384; E-52 to R-383; E-52 to E-382; E-52 to G-381; E-52 to L-380; E-52 to T-379; E-52 to E-378; E-52 to L-377; E-52 to A-376; E-52 to D-375; E-52 to L-374; E-52 to L-373; E-52 to T-372; E-52 to H-371; E-52 to V-370; E-52 to S-369; E-52 to A-368; E-52 to D-367; E-52 to R-366; E-52 to G-365; E-52 to T-364; E-52 to K-363; E-52 to N-362; E-52 to V-361; E-52 to W-360; E-52 to K-359; E-52 to I-358; E-52 to L-357; E-52 to M-356; E-52 to T-355; E-52 to Y-354; E-52 to L-353; E-52 to T-352; E-52 to D-351; E-52 to R-350; E-52 to H-349; E-52 to G-348; E-52 to A-347; E-52 to A-346; E-52 to E-345; E-52 to A-344; E-52 to K-343; E-52 to A-342; E-52 to V-341; E-52 to K-340; E-52 to I-339; E-52 to E-338; E-52 to N-337; E-52 to D-336; E-52 to M-335; E-52 to L-334; E-52 to G-333; E-52 to L-332; E-52 to K-331; E-52 to R-330; E-52 to M-329; E-52 to L-328; E-52 to P-327; E-52 to E-326; E-52 to W-325; E-52 to S-324; E-52 to D-323; E-52 to F-322; E-52 to P-321; E-52 to V-320; E-52 to L-319; E-52 to D-318; E-52 to A-317; E-52 to F-316; E-52 to D-315; E-52 to D-314; E-52 to F-313; E-52 to C-312; E-52 to Q-311; E-52 to R-310; E-52 to L-309; E-52 to T-308; E-52 to E-307; E-52 to T-306; E-52 to P-305; E-52 to D-304; E-52 to G-303; E-52 to E-302; E-52 to N-301; E-52 to A-300; E-52 to P-299; E-52 to V-298; E-52 to L-297; E-52 to L-296; E-52 to R-295; E-52 to R-294; E-52 to R-293; E-52 to Q-292; E-52 to S-291; E-52 to R-290; E-52 to E-289; E-52 to A-288; E-52 to E-287; E-52 to A-286; E-52 to P-285; E-52 to E-284; E-52 to L-283; E-52 to L-282; E-52 to H-281; E-52 to E-280; E-52 to S-279; E-52 to E-278; E-52 to G-277; E-52 to P-276; E-52 to S-275; E-52 to L-274; E-52 to M-273; E-52 to N-272; E-52 to V-271; E-52 to G-270; E-52 to T-269; E-52 to P-268; E-52 to E-267; E-52 to A-266; E-52 to P-265; E-52 to E-264; E-52 to Q-263; E-52 to V-262; E-52 to E-261; E-52 to M-260; E-52 to E-259; E-52 to Q-258; E-52 to E-257; E-52 to P-256; E-52 to V-255; E-52 to Q-254; E-52 to T-253; E-52 to P-252; E-52 to Q-251; E-52 to L-250; E-52 to I-249; E-52 to S-248; E-52 to V-247; E-52 to I-246; E-52 to E-245; E-52 to N-244; E-52 to L-243; E-52 to V-242; E-52 to N-241; E-52 to D-240; E-52 to E-239; E-52 to A-238; E-52 to G-237; E-52 to P-236; E-52 to R-235; E-52 to Q-234; E-52 to S-233; E-52 to S-232; E-52 to R-231; E-52 to D-230; E-52 to V-229; E-52 to R-228; E-52 to E-227; E-52 to P-226; E-52 to D-225; E-52 to G-224; E-52 to G-223; E-52 to G-222; E-52 to G-221; E-52 to S-220; E-52 to C-219; E-52 to I-218; E-52 to G-217; E-52 to K-216; E-52 to L-215; E-52 to Y-214; E-52 to P-213; E-52 to L-212; E-52 to V-211; E-52 to K-210; E-52 to K-209; E-52 to W-208; E-52 to L-207; E-52 to L-206; E-52 to S-205; E-52 to K-204; E-52 to C-203; E-52 to V-202; E-52 to F-201; E-52 to V-200; E-52 to A-199; E-52 to V-198; E-52 to I-197; E-52 to L-196; E-52 to V-195; E-52 to V-194; E-52 to A-193; E-52 to A-192; E-52 to V-191; E-52 to T-190; E-52 to V-189; E-52 to G-188; E-52 to I-187; E-52 to I-186; E-52 to V-191; E-52 to G-184; E-52 to S-183; E-52 to E-182; E-52 to K-181; E-52 to H-180; E-52 to V-179; E-52 to C-178; E-52 to E-177; E-52 to I-176; E-52 to D-175; E-52 to S-174; E-52 to W-173; E-52 to P-172; E-52 to T-171; E-52 to C-170; E-52 to D-169; E-52 to G-168; E-52 to V-167; E-52 to K-166; E-52 to V-165; E-52 to M-164; E-52 to G-163; E-52 to R-162; E-52 to P-161; E-52 to C-160; E-52 to G-159; E-52 to T-158; E-52 to R-157; E-52 to C-156; E-52 to K-155; E-52 to R-154; E-52 to C-153; E-52 to M-152; E-52 to E-151; E-52 to P-150; E-52 to S-149; E-52 to D-148; E-52 to E-147; E-52 to E-146; E-52 to R-145; E-52 to F-144; E-52 to T-143; E-52 to G-142; E-52 to E-141; E-52 to E-140; E-52 to C-139; E-52 to Q-138; E-52 to C-137; E-52 to V-136; E-52 to T-135; E-52 to N-134; E-52 to R-133; E-52 to T-132; E-52 to T-131; E-52 to T-130; E-52 to C-129; E-52 to P-128; E-52 to S-127; E-52 to L-126; E-52 to E-125; E-52 to V-124; E-52 to E-123; E-52 to G-122; E-52 to S-121; E-52 to D-120; E-52 to C-119; E-52 to R-118; E-52 to T-117; E-52 to C-116; E-52 to R-115; E-52 to L-114; E-52 to C-113; E-52 to F-112; E-52 to L-111; E-52 to L-110; E-52 to D-109; E-52 to N-108; E-52 to W-107; E-52 to H-106; E-52 to T-105; E-52 to S-104; E-52 to Y-103; E-52 to D-102; E-52 to Q-101; E-52 to G-100; E-52 to Y-99; E-52 to K-98; E-52 to C-97; E-52 to S-96; E-52 to I-95; E-52 to C-94; E-52 to D-93; E-52 to R-92; E-52 to G-91; E-52 to D-90; E-52 to E-89; E-52 to S-88; E-52 to I-87; E-52 to H-86; E-52 to H-85; E-52 to G-84; E-52 P-83; E-52 to P-82; E-52 to C-81; E-52 to L-80; E-52 to G-79; E-52 to E-78; E-52 to S-77; E-52 to P-76; E-52 to S-75; E-52 to S-74; E-52 to R-73; E-52 to K-72; E-52 to Q-71; E-52 to Q-70; E-52 to P-69; E-52 to A-68; E-52 to A-67; E-52 to R-66; E-52 to Q-65; E-52 to Q-64; E-52 to P-63; E-52 to A-62; E-52 to L-61; E-52 to D-60; E-52 to Q-59; E-52 to Q-58; and E-52 to T-57; of the DR5 sequence shown in FIGS. 1A–B (which is identical to the sequence shown as SEQ ID NO:2, with the exception that the amino acid residues in FIGS. 1A–B are numbered consecutively from 1 through 411 from the N-terminus to the C-terminus, while the amino acid residues in SEQ ID NO:2 are numbered consecutively from −51 through 360 to reflect the position of the predicted signal peptide).

The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The invention is further directed to nucleic acid molecules comprising, or alternatively consisting of, polynucleotide sequences which encode polypeptides that are at least 80%, 85%, 90%, 92%, 95%, 96%, 97%, 98%, or 99% identical to the polypeptides described above. The present invention also encompasses the above polynucleotide sequences fused to a heterologous polynucleotide sequence. Polypeptides encoded by these polynucleotides are also encompassed by the invention.

In another embodiment, C-terminal deletions of the DR5 polypeptide can be described by the general formula 52-$m^2$ where $m^2$ is a number from 57 to 183 corresponding to the amino acid sequence identified in FIGS. 1A–B (SEQ ID NO:2). In specific embodiments, C-terminal deletions of the DR5 of the invention comprise, or alternatively consist of, a member selected from the group consisting of residues: E-52 to S-183; E-52 to E-182; E-52 to K-181; E-52 to H-180; E-52 to V-179; E-52 to C-178; E-52 to E-177; E-52 to I-176; E-52 to D-175; E-52 to S-174; E-52 to W-173; E-52 to P-172; E-52 to T-171; E-52 to C-170; E-52 to D-169; E-52 to G-168; E-52 to V-167; E-52 to K-166; E-52 to V-165; E-52 to M-164; E-52 to G-163; E-52 to R-162; E-52 to P-161; E-52 to C-160; E-52 to G-159; E-52 to T-158; E-52 to R-157; E-52 to C-156; E-52 to K-155; E-52 to R-154; E-52 to C-153; E-52 to M-152; E-52 to E-151; E-52 to P-150; E-52 to S-149; E-52 to D-148; E-52 to E-147; E-52 to E-146; E-52 to R-145; E-52 to F-144; E-52 to T-143; E-52 to G-142; E-52 to E-141; E-52 to E-140; E-52 to C-139;E-52to Q-138; E-52 to C-137; E-52 to V-136; E-52 to T-135; E-52 to N-134; E-52 to R-133; E-52 to T-132; E-52 to T-131; E-52 to T-130; E-52 to C-129; E-52 to P-128; E-52 to S-127; E-52 to L-126; E-52 to E-125; E-52 to V-124; E-52 to E-123; E-52 to G-122; E-52to S-121; E-52 to D-120; E-52 to C-119; E-52 to R-118; E-52 to T-117; E-52 to C-116; E-52 to R-115; E-52 to L-114; E-52 to C-113; E-52 to F-112; E-52 to L-111; E-52 to L-110; E-52 to D-109; E-52 to N-108; E-52 to W-107; E-52 to H-106; E-52 to T-105; E-52 to S-104; E-52 to Y-103; E-52 to D-102; E-52 to Q-101; E-52 to G-100; E-52 to Y-99; E-52 to K-98; E-52 to C-97; E-52 to S-96; E-52 to I-95; E-52 to C-94; E-52 to D-93; E-52 to R-92; E-52 to G-91; E-52 to D-90; E-52 to E-89; E-52 to S-88; E-52 to I-87; E-52 to H-86; E-52 to H-85; E-52 to G-84; E-52 to P-83; E-52 to P-82; E-52 to C-81; E-52 to L-80; E-52 to G-79; E-52 to E-78; E-52 to S-77; E-52 to P-76; E-52 to S-75; E-52 to S-74; E-52 to R-73; E-52 to K-72; E-52 to Q-71; E-52 to Q-70; E-52 to P-69; E-52 to A-68; E-52 to A-67; E-52 to R-66; E-52 to Q-65; E-52 to Q-64; E-52 to P-63; E-52 to A-62; E-52 to L-61; E-52 to D-60; E-52 to Q-59; E-52 to Q-58; and E-52 to T-57 of the DR5 extracellular domain sequence shown in FIGS. 1A–B (SEQ ID NO:2).

The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The invention is further directed to nucleic acid molecules comprising, or alternatively consisting of, polynucleotide sequences which encode polypeptides that are at least 80%, 85%, 90%, 92%, 95%, 96%, 97%, 98%, or identical to the polypeptides described above. The present invention also encompasses the above polynucleotide sequences fused to a heterologous polynucleotide sequence. Polypeptides encoded by these polynucleotides are also encompassed by the invention.

The invention also provides polypeptides having one or more amino acids deleted from both the amino and the carboxyl termini of a DR5 polypeptide, which may be described generally as having residues $n^1-m^1$ and/or $n^2-m^2$ of FIGS. 1A–B (i.e., SEQ ID NO:2), where $n^1$, $n^2$, $m^1$, and $m^2$ are integers as described above.

Also included are a nucleotide sequence encoding a polypeptide consisting of a portion of the complete DR5 amino acid sequence encoded by the cDNA contained in ATCC Deposit No. 97920, where this portion excludes from 1 to about 78 amino acids from the amino terminus of the complete amino acid sequence encoded by the cDNA contained in ATCC Deposit No. 97920, or from 1 to about 233 amino acids from the carboxy terminus, or any combination of the above amino terminal and carboxy terminal deletions, of the complete amino acid sequence encoded by the cDNA contained in ATCC Deposit No. 97920. Polynucleotides encoding all of the above deletion mutant polypeptide forms also are provided.

Preferred amongst the N- and C-terminal deletion mutants are those comprising, or alternatively consisting of, only a portion of the extracellular domain; i.e., within residues 52–184, since any portion therein is expected to be soluble.

It will be recognized in the art that some amino acid sequence of DR5 can be varied without significant effect of the structure or function of the protein. If such differences in sequence are contemplated, it should be remembered that there will be critical areas on the protein which determine activity. Such areas will usually comprise residues which make up the ligand binding site or the death domain, or which form tertiary structures which affect these domains.

Thus, the invention further includes variations of the DR5 protein which show substantial DR5 protein activity or which include regions of DR5, such as the protein portions discussed below. Such mutants include deletions, insertions, inversions, repeats, and type substitutions. As indicated above, guidance concerning which amino acid changes are likely to be phenotypically silent can be found in Bowie, J. U. et al., *Science* 247:1306–1310 (1990).

Thus, the fragment, derivative, or analog of the polypeptide of SEQ ID NO:2, or that encoded by the deposited cDNA, may be (i) one in which at least one or more of the amino acid residues are substituted with a conserved or non-conserved amino acid residue (preferably a conserved amino acid residue(s) and more preferably at least one but less than ten conserved amino acid residues) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein. Polynucleotides encoding these fragments, derivatives or analogs are also encompassed by the invention.

Of particular interest are substitutions of charged amino acids with another charged amino acids and with neutral or negatively charged amino acids. The latter results in proteins with reduced positive charge to improve the characteristics of the DR5 protein. Additionally, one or more of the amino acid residues of the polypeptides of the invention (e.g., arginine and lysine residues) may be deleted or substituted with another residue to eliminate undesired processing by proteases such as, for example, furins or kexins. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al. *Crit Rev. Therapeutic Drug Carrier Systems* 10:307–377 (1993)).

The replacement of amino acids can also change the selectivity of binding to cell surface receptors. Ostade et al., *Nature* 361:266–268 (1993) describes certain mutations resulting in selective binding of TNF-alpha to only one of the two known types of TNF receptors. Thus, the DR5 receptor of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table II).

TABLE II

Conservative Amino Acid Substitution

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

In specific embodiments, the number of substitutions, additions or deletions in the amino acid sequence of FIGS. 1A–B and/or any of the polypeptide fragments described herein (e.g., the extracellular domain or intracellular domain) is 75, 70, 60, 50, 40, 35, 30, 25, 20, 15, 10, 9, 8, 7, 6, 5, 4, 3, 2, 1 or 30–20, 20–15, 20–10, 15–10, 10–1, 5–10, 1–5, 1–3 or 1–2. Polynucleotides encoding these polypeptides are also encompassed by the invention.

Amino acids in the DR5 protein of the present invention that are essential for function can be identified by methods known in the art, such as site-directed mutagenesis or alanine-scanning mutagenesis (Cunningham and Wells, Science 244:1081–1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

Additionally, protein engineering may be employed to improve or alter the characteristics of DR5 polypeptides. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

Non-naturally occurring variants may be produced using art-known mutagenesis techniques, which include, but are not limited to oligonucleotide mediated mutagenesis, alanine scanning, PCR mutagenesis, site directed mutagenesis (see e.g., Carter et al., *Nucl. Acids Res.* 13:4331 (1986); and Zoller et al., *Nucl. Acids Res.* 10:6487 (1982)), cassette mutagenesis (see e.g., Wells et al., *Gene* 34:315 (1985)), and restriction selection mutagenesis (see e.g., Wells et al, *Philos. Trans. R. Soc. London SerA* 317:415 (1986)).

Thus, the invention also encompasses DR5 derivatives and analogs that have one or more amino acid residues deleted, added, or substituted to generate DR5 polypeptides that are better suited for expression, scale up, etc., in the host cells chosen. For example, cysteine residues can be deleted or substituted with another amino acid residue in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions on any one or more of the glycosylation recognitions sequences in the DR5 polypeptides of the invention, and/or an amino acid deletion at the second position of any one or more such recognition sequences will prevent glycosylation of the DR5 at the modified tripeptide sequence (see, e.g., Miyajimo et al., *EMBO J* 5(6): 1193–1197).

The polypeptides of the present invention also include a polypeptide comprising, or alternatively consisting of, one, two, three, four, five or more amino acid sequences selected from the group consisting of: the polypeptide encoded by the deposited cDNA (the deposit having ATCC Accession Number 97920) including the leader; the mature polypeptide encoded by the deposited the cDNA minus the leader (i.e., the mature protein); a polypeptide comprising, or alternatively consisting of, amino acids from about −51 to about 360 in SEQ ID NO:2; a polypeptide comprising, or alternatively consisting of, amino acids from about −50 to about 360 in SEQ ID NO:2; a polypeptide comprising, or alternatively consisting of, amino acids from about 1 to about 360 in SEQ ID NO:2; a polypeptide comprising, or alternatively consisting of, the DR5 extracellular domain; a polypeptide comprising, or alternatively consisting of, the DR5 cysteine rich domain; a polypeptide comprising, or alternatively consisting of, the DR5 transmembrane domain; a polypeptide comprising, or alternatively consisting of, the DR5 intracellular domain; a polypeptide comprising, or alternatively consisting of, the extracellular and intracellular domains with all or part of the transmembrane domain deleted; and a polypeptide comprising, or alternatively consisting of, the DR5 death domain; as well as polypeptides which are at least 80% identical, more preferably at least 90% or 95% identical, still more preferably at least 96%, 97%, 98%, or 99% identical to the polypeptides described above, and also include portions of such polypeptides with at least 30 amino acids and more preferably at least 50 amino acids. Polynucleotides encoding these polypeptides are also encompassed by the invention.

By a polypeptide having an amino acid sequence at least, for example, 95% "identical" to a reference amino acid sequence of a DR5 polypeptide is intended that the amino acid sequence of the polypeptide is identical to the reference sequence except that the polypeptide sequence may include up to five amino acid alterations per each 100 amino acids of the reference amino acid of the DR5 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 92%, 95%, 96%, 97%, 98% or 99% identical to, for instance, the amino acid sequence shown in FIGS. 1A–B (SEQ ID NO:2), the amino acid sequence encoded by the deposited cDNA, or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty= 0.05, Window Size=500 or the length of the subject amino acid sequence, whichever is shorter According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by, the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The polypeptide of the present invention have uses that include, but are not limited to, use as a molecular weight marker on SDS-PAGE gels or on molecular sieve gel filtration columns and as a source for generating antibodies that bind the polypeptides of the invention, using methods well known to those of skill in the art.

The present application is also directed to proteins containing polypeptides at least 80%, 85%, 90%, 92%, 95%, 96%, 97%, 98% or 99% identical to the DR5 polypeptide sequence set forth herein as $n^1-m^1$, and/or $n^2-m^2$. In preferred embodiments, the application is directed to proteins containing polypeptides at least 80%, 85%, 90%, 92%, 95%, 96%, 97%, 98% or 99% identical to polypeptides having the amino acid sequence of the specific DR5 N- and C-terminal deletions recited herein. Polynucleotides encoding these polypeptides are also encompassed by the invention.

In certain preferred embodiments, DR5 proteins of the invention comprise fusion proteins as described above wherein the DR5 polypeptides are those described as $n^1-m^1$, and $n^2-m^2$, herein. In preferred embodiments, the application is directed to nucleic acid molecules at least 80%, 85%, 90%, 92%, 95%, 96%, 97%, 98% or 99% identical to the nucleic acid sequences encoding polypeptides having the amino acid sequence of the specific N- and C-terminal deletions recited herein. Polynucleotides encoding these polypeptides are also encompassed by the invention.

The present inventors have discovered that the DR5 polypeptide is a 411 residue protein exhibiting three main structural domains. First, the ligand binding domain (extracellular domain) was identified within residues from about 52 to about 184 in FIGS. 1A–B (amino acid residues from about 1 to about 133 in SEQ ID NO:2). Second, the transmembrane domain was identified within residues from about 185 to about 208 in FIGS. 1A–B (amino acid residues from about 134 to about 157 in SEQ ID NO:2). Third, the intracellular domain was identified within residues from about 209 to about 411 in FIGS. 1A–B (amino acid residues from about 158 to about 360 in SEQ ID NO:2). Importantly, the intracellular domain includes a death domain at residues from about 324 to about 391 (amino acid residues from about 273 to about 340 in SEQ ID NO:2). Further preferred fragments of the polypeptide shown in FIGS. 1A–B include the mature protein from residues about 52 to about 411 (amino acid residues from about 1 to about 360 in SEQ ID NO:2), and soluble polypeptides comprising all or part of the extracellular and intracellular domains but lacking the transmembrane domain.

The invention further provides DR5 polypeptides encoded by the deposited cDNA including the leader and DR5 polypeptide fragments selected from the mature protein, the extracellular domain, the transmembrane domain, the intracellular domain, the death domain, and all combinations thereof.

In addition, proteins of the invention can be chemically synthesized using techniques known in the art (e.g., see Creighton, 1983, Proteins: Structures and Molecular Principles, W. H. Freeman & Co., N.Y., and Hunkapiller, M., et al., Nature 310:105–111 (1984)). For example, a peptide corresponding to a fragment of the DR5 polypeptides of the invention can be synthesized by use of a peptide synthesizer.

Furthermore, if desired, nonclassical amino acids or chemical amino acid analogs can be introduced as a substitution or addition into the DR5 polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

Non-naturally occurring variants may be produced using art-known mutagenesis techniques, which include, but are not limited to oligonucleotide mediated mutagenesis, alanine scanning, PCR mutagenesis, site directed mutagenesis (see, e.g., Carter et al, *Nucl. Acids Res.* 13:4331 (1986); and Zoller et al., *Nucl. Acids Res.* 10:6487 (1982)), cassette mutagenesis (see, e.g., Wells et al., *Gene* 34:315 (1985)), restriction selection mutagenesis (see, e.g., Wells et al., *Philos. Trans. R. Soc. London SerA* 317:415 (1986)).

The invention additionally, encompasses DR5 polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin; etc.

Additional post-translational modifications encompassed by the invention include, for example, e.g., N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of DR5 which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al, *Appl. Biochem. Biotechnol.* 56:59–72 (1996); Vorobjev et al., *Nucleosides Nucleotides* 18:2745–2750 (1999); and Caliceti et al., *Bioconjug. Chem.* 10:638–646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic-acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g. lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249–304 (1992); Francis et al., *Intern. J. of Hematol.* 68:1–18 (1998); U.S. Pat. Nos. 4,002,531; 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1–3, 2–4, 3–5, 4–6, 5–7, 6–8, 7–9, 8–10, 9–11, 10–12, 11–13, 12–14, 13–15, 14–16, 15–17, 16–18, 17–19, or 18–20 polyethylene glycol moieties per protein molecule. Methods for determining the degree of substitution are discussed, for example, in Delgado et al., *Crit. Rev. Thera. Drug Carrier Sys.* 9:249–304 (1992).

As mentioned, DR5 polypeptides may be modified by either natural processes, such as posttranslational processing, or by chemical modification techniques which are well known in the art. It will be appreciated that the same type of modification may be present in the same or varying degrees at several sites in a given DR5 polypeptide. Also, a given DR5 polypeptide may contain many types of modifications. DR5 polypeptides may be branched, for example, as a result of ubiquitination, and they may be cyclic, with or without branching. Cyclic, branched, and branched cyclic DR5 polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992)).

The DR5 polypeptides can be recovered and purified from chemical synthesis and recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and/or purification.

DR5 polynucleotides and polypeptides may be used in accordance with the present invention for a variety of applications, particularly those that make use of the chemical and biological properties of DR5. Among these are applications in the treatment and/or prevention of tumors, parasitic infections, bacterial infections, viral infections, restenosis, and graft vs. host disease; to induce resistance to parasites, bacteria and viruses; to induce proliferation of T-cells, endothelial cells and certain hematopoietic cells; to regulate anti-viral responses; and to treat and/or prevent certain autoimmune diseases after stimulation of DR5 by an agonist. Additional applications relate to diagnosis, treatment, and/or prevention of disorders of cells, tissues and organisms These aspects of the invention are discussed further below.

The present invention encompasses polypeptides comprising, or alternatively consisting of, an epitope of the polypeptide having an amino acid sequence of SEQ ID NO:2, or an epitope of the polypeptide sequence encoded by a polynucleotide sequence contained in the cDNA deposited as ATCC Deposit No. 97920 or encoded by a polynucleotide that hybridizes to the complement of the sequence of SEQ ID NO:1 or contained in the cDNA deposited as ATCC Deposit No. 97920 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

In another aspect, the invention provides a peptide or polypeptide comprising an epitope-bearing portion of a polypeptide described herein. The epitope of this polypeptide portion is an immunogenic or antigenic epitope of a polypeptide of the invention. The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

Fragments that function as epitopes may be produced by any conventional means. (See, e.g., Houghten, *Proc. Natl Acad. Sci. USA* 82:5131–5135 (1985), further described in U.S. Pat. No. 4,631,211).

As to the selection of peptides or polypeptides bearing an antigenic epitope (i. e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A., "Antibodies That React With Predetermined Sites on Proteins," *Science* 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Non-limiting examples of antigenic polypeptides or peptides that can be used to generate DR5-specific antibodies include: a polypeptide comprising, or alternatively consisting of, amino acid residues from about 62 to about 110 in FIGS. 1A–B (about 11 to about 59 in SEQ ID NO:2); a polypeptide comprising, or alternatively consisting of, amino acid residues from about 119 to about 164 in FIGS. 1A–B (about 68 to about 113 in SEQ ID NO:2); a polypeptide comprising, or alternatively consisting of, amino acid residues from about 224 to about 271 in FIGS. 1A–B (about 173 to about 220 in SEQ ID NO:2); and a polypeptide comprising, or alternatively consisting of, amino acid residues from about 275 to about 370 in FIGS. 1A–B (about 224 to about 319 in SEQ ID NO:2). As indicated above, the inventors have determined that the above polypeptide fragments are antigenic regions of the DR5 protein.

The epitope-bearing peptides and polypeptides of the invention may be produced by any conventional means. Hougthen, R. A., "General Method for the Rapid Solid-Phase Synthesis of Large Numbers of Peptides: Specificity of Antigen-Antibody Interaction at the Level of Individual Amino Acids," *Proc. Natl. Acad. Sci. USA* 82:5131–5135 (1985). This "Simultaneous Multiple Peptide Synthesis (SMPS)" process is further described in U.S. Pat. No. 4,631,211 to Hougthen et al. (1986). As one of skill in the art will appreciate, DR5 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84–86 (1988)). Fusion proteins that have a disulfide-linked dimeric structure due to the IgG part can also be more efficient in binding and neutralizing other molecules than the monomeric DR5 protein or protein fragment alone (Fountoulakis et al., *J. Biochem.* 270:3958–3964 (1995)).

Antibodies

The present invention further relates to antibodies and T-cell antigen receptors (TCR) which immunospecifically bind a polypeptide, preferably an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a $V_L$ or $V_H$ domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine, donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt et al., J. Immunol. 147:60–69 (1991); U.S.

Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention that they recognize or specifically bind. The epitope(s) or polypeptide portion(s) may be specified as described herein, e.g., by N-terminal and C-terminal positions, by size in contiguous amino acid residues, or listed in the Tables and Figures. Antibodies that specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies that bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5 \times 10^{-2}$M, $10^{-2}$M, $5 \times 10^{-3}$M, $10^{-3}$M, $5 \times 10^{-4}$M, $10^{-4}$M, $5 \times 10^{-5}$M, $10^{-5}$M, $5 \times 10^{-6}$M, $10^{-6}$M, $10^{-7}$M, $5 \times 10^{-8}$M, $10^{-8}$M, $5 \times 10^{-9}$M, $10^{-9}$M, $5 \times 10^{-10}$M, $10^{-10}$M, $5 \times 10^{-11}$M, $10^{-11}$M, $5 \times 10^{-12}$M, $10^{-12}$M, $5 \times 10^{13}$M, $10^{-13}$M, $5 \times 10^{-14}$M, $10^{-14}$M, $5 \times 10^{-15}$M, and $10^{-15}$M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 90%, at least 80%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand or receptor activity by at least 90%, at least 80%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation. The antibodies may be specified as agonists, antagonists or inverse agonists for biological activities comprising the specific biological activities of the peptides of the invention disclosed herein. Thus, the invention further relates to antibodies which act as agonists or antagonists of the polypeptides of the present invention. The above antibody agonists can be made using methods known in the art. See, e.g., PCT publication WO 96/40281; U.S. Pat. No. 5,811,097, Deng et al., Blood 92(6):1981–1988 (1998); Chen et al., Cancer Res. 58(16):3668–3678 (1998); Harrop et al, J. Immunol. 161(4):1786–1794 (1998); Zhu et al., Cancer Res. 58(15):3209–3214 (1998); Yoon et al., J. Immunol. 160(7):3170–3179 (1998); Prat et al., J. Cell. Sci. 111(Pt2):237–247 (1998); Pitard et al., J. Immunol. Methods 205(2):177–190 (1997); Liautard et al., Cytokine 9(4):233–241 (1997); Carlson et al., J. Biol. Chem. 272(17) 11295–11301 (1997); Taryman et al., Neuron 14(4):755–762 (1995); Muller et al., Structure 6(9): 1153–1167(1998); Bartunek et al., Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides. drugs, or toxins See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen of interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling et al., in: Monoclonal Antibodies and T-Cell Hybridomas 563–681 (Elsevier, N.Y, 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. Monoclonal antibodies can be prepared using a wide variety of techniques known in the art including the use of hybridoma and recombinant and phage display technology.

Methods for producing and screening for specific antibodies using hybridoma technology are routine and well-known in the art and are discussed in detail in Example 11. Briefly, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods* 182:41–50 (1995); Ames et al., *J. Immunol. Methods* 184:177–186 (1995); Kettleborough et al., *Eur. J. Immunol.* 24:952–958 (1994); Persic et al., *Gene* 187:9–18 (1997); Burton et al., *Advances in Immunology* 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below, For example, techniques to recombinantly produce Fab, Fab' and F(ab')2 fragments can also be employed using methods known in the art such as those disclosed in PCT publication WO 92/22324; Mullinax et al., *BioTechniques* 12(6):864–869 (1992); and Sawai et al, *AJRI* 34:26–34 (1995); and Better et al., *Science* 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46–88 (1991); Shu et al., *PNAS* 90:7995–7999 (1993); and Skerra et al., *Science* 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, *Science* 229:1202 (1985); Oi et al., *BioTechniques* 4:214 (1986);

Gillies et al., (1989) *J. Immunol. Methods* 125:191–202; U.S. Pat. Nos. 5,807,715; 4,816,567; and 4,816397, which are incorporated herein by reference in their entireties. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530, 101, and 5,585,089), veneering or resurfacing (EP 592,106; EP 519,596; Padlan, Molecular Immunology 28(4/5) :489–498 (1991); Studnicka et al., Protein Engineering 7(6):805–814 (1994); Roguska. et al., PNAS 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716, 111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65–93). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/technology* 12:899–903 (1988)).

Further, antibodies to the polypeptides of the invention can, in turn,-be utilized to generate anti-idiotype antibodies that "mimic" polypeptides of the invention using techniques well known to those skilled in the art. (See, e.g., Greenspan & Bona, *FASEB J.* 7(5):437–444 (1989) and Nissinoff, *J. Immunol.* 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

A. Polynucleotides Encoding Antibodies.

The invention further provides polynucleotides comprising a nucleotide sequence encoding an antibody of the invention and fragments thereof The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., *BioTechniques* 17:242 (1994)), which, briefly, involves the synthesis of overlapping oligonucleotides containing portions of the sequence encoding the antibody, annealing and ligation of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be obtained from a suitable source (e.g., an antibody cDNA library, or a cDNA library generated from, or nucleic acid, preferably polyA+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., *J. Mol. Biol.* 278:457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., 1984, *Proc. Natl. Acad. Sci.* 81:851–855; Neuberger et al., 1984, *Nature* 312:604–608; Takeda et al., 1985, *Nature* 314–452–454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine monoclonal antibody and a human immunoglobulin constant region, e.g., humanized antibodies.

Alternatively, techniques described for the production of single chain antibodies (U.S. Pat. No. 4,694,778; Bird, 1988, *Science* 242:423–42; Huston et al., 1988, *Proc. Natl. Acad. Sci. USA* 85:5879–5883; and Ward et al., 1989, *Nature* 334:544–554) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., 1988, *Science* 242:1038–1041).

B. Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, e.g., a heavy or light chain of an antibody of the invention, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, *Gene* 45:101; Cockett et al., 1990, *Bio/Technology* 8:2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., 1983, *EMBO J.* 2:1791), in which the antibody coding sequence may be ligated individually into the vector in frame with the lacZ coding region so that a fusion protein is produced; pIN vectors (Inouye & Inouye, 1985, *Nucleic Acids Res.* 13:3101–3109; Van Heeke & Schuster, 1989, *J. Biol. Chem.* 24:5503–5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, 1984, *Proc. Natl. Acad. Sci. USA* 81:355–359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, *Methods in Enzymol.* 153:51–544).

In addition, a host cell strain may be chosen which modulates the expression of the inserted sequences, or modifies and processes the gene product in the specific fashion desired. Such modifications (e.g. glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of-the gene product may be used. Such mammalian host cells include but are not limited to CHO, VERY, BHK, HeLa, COS, MDCK, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., 1977, *Cell* 11:223), hypoxanthine-guanine phosphoribosyltransferase (Szybalska & Szybalski, 192, *Proc. Natl. Acad. Sci. USA* 48:202), and adenine phosphoribosyltransferase (Lowy et al., 1980, *Cell* 22:817) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIB TECH 11(5):155–215); and hygro, which confers resistance to hygromycin (Santerre et al, 1984, Gene 30: 147). Methods commonly known in the art of recombinant DNA technology which can be used are described in Ausubel et al. (eds.), 1993, *Current Protocols in Molecular Biology*, John Wiley & Sons, NY; Kriegler, 1990, *Gene Transfer and Expression, A Laboratory Manual*, Stockton Press, NY; and in Chapters 12 and 13, Dracopoli et al. (eds), 1994, *Current Protocols in Human Genetics*, John Wiley & Sons, NY.; Colberre-Garapin et al., 1981, *J. Mol. Biol.* 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, *Mol. Cell. Biol.* 3:257)

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, *Nature* 322:52; Kohler, 1980, *Proc. Natl. Acad. Sci. USA* 77:2197). The coding sequences for the heavy and light chains may comprise cDNA or genomic DNA.

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins.

C. Antibody Conjugates

The present invention encompasses antibodies recombinantly fused or chemically conjugated (including both covalently and non-covalently conjugations) to a polypeptide (or portion thereof, preferably at least 10, 20 or 50 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20 or 50 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., *Immunol. Lett.* 39:91–99 (1994); U.S. Pat. No. 5,474,981; Gillies et al., *PNAS* 89:1428–1432 (1992); Fell et al., *J. Immunol.* 146:2446–2452 (1991), which are incorporated by reference in their entireties The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., *Proc. Natl. Acad. Sci. USA* 88:10535–10539 (1991); Zheng et al., *J. Immunol.* 154:5590–5600 (1995); and Vil et al., *Proc. Natl. Acad. Sci. USA* 89:11337–11341(1992) (said references incorporated by reference in their entireties).

As discussed, supra, the polypeptides of the present invention may be fused or conjugated to the above antibody portions to increase the in vivo half life of the polypeptides or for use in immunoassays using methods known in the art. Further, the polypeptides of the present invention may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., *Nature* 331:84–86 (1988). The polypeptides of the present invention fused or conjugated to an antibody having disulfide- linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5 receptor, have been fused with Fc portions for the purpose of high-throughput screening assays to identify antagonists of hIL-5. (See, D. Bennett et al., *J. Molecular Recognition* 8:52–58 (1995); K. Johanson et al., *J. Biol. Chem.* 270:9459–9471 (1995).

Moreover, the antibodies or fragments thereof of the present invention can be fused to marker sequences, such as a peptide to facilitates their purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell* 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment and/or prevention regimens. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic met al ions. See, for example, U.S. Pat. No. 4,741,900 for metal ions which can be conjugated to antibodies for use as diagnostics according to the present invention. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$J, $^{111}$In or $^{99}$Tc.

Further, an antibody or fragment thereof may be conjugated to a therapeutic moiety such as a cytotoxin, e.g., a cytostatic or cytocidal agent, a therapeutic agent or a radioactive met al ion. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in *Monoclonal Antibodies And Cancer Therapy*, Reisfeld et al. (eds.), pp. 243–56 (Alan R. Liss, Inc. 1985); Hellstrom et al., "Antibodies For Drug Delivery", in *Controlled Drug Delivery* (2nd Ed.), Robinson et al. (eds.), pp. 623–53 (Marcel Dekker, Inc. 1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475–506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), pp. 303–16 (Academic Press 1985), and Thorpe et al., "The Preparation And Cytotoxic Properties Of Antibody-Toxin Conjugates", *Immunol. Rev.* 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

D. Assays For Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period_of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al., eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3H$ or $^{125}I$) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest is conjugated to a labeled compound (e.g., $^3H$ or $^{125}I$) in the presence of increasing amounts of an unlabeled second antibody.

E. Antibody Based Therapies

The present invention is further directed to antibody-based therapies which involve administering antibodies of the invention to an animal, preferably a mammal, and most preferably a human, patient for treating and/or preventing one or more of the disorders or conditions described herein. Therapeutic compounds of the invention include, but are not limited to, antibodies of the invention (including fragments, analogs and derivatives thereof as described herein) and nucleic acids encoding antibodies of the invention (including fragments, analogs and derivatives thereof as described herein).

While not intending to be bound to theory, DR5 receptors are believed to induce programmed cell death by a process which involves the association/cross-linking of death domains between different receptor molecules. Further, DR5 ligands (e.g., TRAIL) which induce DR5 mediated programmed cell death are believed to function by causing the association/cross-linking of DR5 death domains. Thus, agents (e.g., antibodies) which prevent association/cross-linking of DR5 death domains will prevent DR5 mediated programmed cell death, and agents (e.g., antibodies) which facilitate the association/cross-linking of DR5 death domains will induce DR5 mediated programmed cell death.

As noted above, DR5 receptors have been shown to bind TRAIL. DR5 receptors are also known to be present in a number of tissues and on the surfaces of a number of cell types. These tissues and cell types include primary dendritic cells, endothelial tissue, spleen, lymphocytes of patients with chronic lymphocytic leukemia, and human thymus stromal cells. Further, as explained in more detail below, TRAIL has been shown to induce apoptosis and to inhibit the growth of tumor cells in vivo. Additionally, TRAIL activities are believed to be modulated, at least in part, through interaction with DR4 and DR5 receptors.

TRAIL is a member of the TNF family of cytokines which has been shown to induce apoptotic cell death in a number of tumor cell lines and appears to mediate its apoptosis inducing effects through interaction with DR4 and DR5 receptors. These death domain containing receptors are believed to form membrane-bound self-activating signaling complexes which initiate apoptosis through cleavage of caspases.

In addition to DR4 and DR5 receptors, TRAIL also binds to several receptors proposed to be "decoy" receptors, DcR2 (a receptor with a truncated death domain), DcR1 (a GPI-anchored receptor), and OPG (a secreted protein which binds to another member of the TNF family, RANKL).

Further, recent studies have shown that the rank-order of affinities of TRAIL for the recombinant soluble forms of its receptors is strongly temperature dependent. In particular, at 37° C., DR5 has the highest affinity for TRAIL and OPG having the lowest affinity.

The DR4 and DR5 receptor genes, as well as genes encoding two decoy receptors, have been shown to be located on human chromosome 8p21–22. Further, this region of the human genome is frequently disrupted in head and neck cancers.

It has recently been found that the FaDu nasopharyngeal cancer cell line contains an abnormal chromosome 8p21–22 region. (Ozoren et al., *Int. J. Oncol.* 16:917–925 (2000).) In particular, a homozygous deletion involving DR4, but not DR5, has been found in these cells. (Ozoren et al., *Int. J. Oncol* 16:917–925 (2000).) The homozygous loss within the DR4 receptor gene in these FaDu cells encompasses the DR4 receptor death domain. This disruption of the DR4 receptor death domain is associated with resistance to TRAIL-mediated cytotoxicity. Further, re-introduction of a wild-type DR4 receptor gene has been shown to both lead to apoptosis and restoration of TRAIL sensitivity of FaDu cells. (Ozoren et al., *Int. J. Oncol.* 6:917–925 (2000).) These data indicate that the DR4 receptor gene may be inactivated in human cancers and DR4 receptor gene disruption may contribute to resistance to TRAIL therapy. It is expected that similar results would be found in cells having analogous deletions in the DR5 gene.

It has also been shown that overexpression of the cytoplasmic domain of the DR4 receptor in human breast, lung, and colon cancer cell lines leads to p53-independent apoptotic cell death which involves the cleavage of caspases. (Xu et al., *Biochem. Biophys. Res. Commun.* 269:179–190 (2000).) Further, DR4 cytoplasmic domain overexpression has also been shown to result in cleavage of both poly(ADP-ribose) polymerase (PARP) and a DNA fragmentation factor (i.e., ICAD-DFF45). (Xu et al., *Biochem. Biophys. Res. Commun.* 269:179–190 (2000).) In addition, despite similar levels of DR4 cytoplasmic domain protein as compared to cancer cells tested, normal lung fibroblasts have been shown to be resistant to DR4 cytoplasmic domain overexpression and show no evidence of caspase-cleavage. (Xu et al., *Biochem. Biophys. Res. Commun.* 269:179–190 (2000).) Again, similar results are expected with cells that overexpress the cytoplasmic domain of DR5. Thus, the cytoplasmic domains of the DR4 and DR5 receptors are useful as agents for inducing apoptosis, for example, in cancer cells.

Further, overexpression of the cyclin-dependent kinase inhibitor p21 (WAF1/CIP1), as well as the N-terminal 91 amino acids of this protein, has cell cycle-inhibitory activity and inhibits DR4 cytoplasmic domain-dependent caspase cleavage. Thus, DR4 receptors are also involved in the regulation of cell cycle progression. As above, similar results are expected with the DR5 receptor. Thus, the DR4 and DR5 receptors, as well as agonists and antagonists of these receptors, are useful for regulating cell cycle progression.

Antibodies which bind to DR5 receptors are useful for treating and/or preventing diseases and conditions associated with increased or decreased DR5-induced apoptotic cells death. Further, these antibodies vary in the effect they have on DR5 receptors. These effects differ based on the specific portions of the DR5 receptor to which the antibodies bind, the three-dimensional conformation of the antibody molecules themselves, and/or the manner in which they interact with the DR5 receptor. Thus, antibodies which bind to the extracellular domain of a DR5 receptor can either stimulate or inhibit DR5 activities (e.g., the induction of apoptosis). Antibodies which stimulate DR5 receptor activities (e.g., by facilitating the association between DR5 receptor death domains) are DR5 agonists, and antibodies which inhibit DR5 receptor activities (e.g., by blocking the binding of TRAIL and/or preventing the association between DR5 receptor death domains) are DR5 antagonists.

Antibodies of the invention which function as agonists and antagonists of DR5 receptors include antigen-binding antibody fragments such as Fab and F(ab')$_2$ fragments, Fd, single-chain Fvs (scFv), disulfide-linked Fvs (sdFv) and fragments comprising either a V$_L$ or V$_H$ domain, as well as polyclonal, monoclonal and humanized antibodies. Divalent antibodies are preferred as agonists. Each of these antigen-binding antibody fragments and antibodies are described in more detail elsewhere herein.

In view of the above, antibodies of the invention, as well as other agonists, are useful for stimulating DR5 death domain activity to promote apoptosis in cells which express DR5 receptors (e.g., cancer cells). Antibodies of this type are useful for prevention and/or treating diseases and conditions associated with increased cell survival and/or insensitivity to apoptosis-inducing agents (e.g., TRAIL), such as solid tissue cancers (e.g., skin cancer, head and neck tumors, breast tumors, endothelioma, lung cancer, osteoblastoma, osteoclastoma, and Kaposi's sarcoma) and leukemias.

Antagonists of the invention (e.g., anti-DR5 antibodies) function by preventing DR5 mediated apoptosis and are useful for preventing and/or treating diseases associated with increased apoptotic cell death. Examples of such diseases include diabetes mellitus, AIDS, neurodegenerative disorders, myelodysplastic syndromes, ischemic injury, toxin-induced liver disease, septic shock, cachexia and anorexia.

As noted above, DR5 receptors are present on the surfaces of T-cells. Thus, agonists of the invention (e.g., anti-DR5 receptor antibodies) are also useful for inhibiting T-cell mediated immune responses, as well as preventing and/or treating diseases and conditions associated with increased T-cell proliferation. Diseases and conditions associated with T-cell mediated immune responses and increased T-cell proliferation include graft-v-host responses and diseases, osteoarthritis, psoriasis, septicemia, inflammatory bowel disease, inflammation in general, autoimmune diseases, and T-cell leukemias.

When an agonist of the invention is administered to an individual for the treatment and/or prevention of a disease or condition associated with increased T-cell populations or increased cell proliferation (e.g., cancer), the antagonist may be co-administered with another agent which induces apoptosis (e.g., TRAIL) or otherwise inhibits cell proliferation (e.g., an anti-cancer drug). Combination therapies of this nature, as well as other combination therapies, are discussed below in more detail Further, antagonists of the invention (e.g., anti-DR5 receptor antibodies) are also useful for enhancing T-cell mediated immune responses, as well as preventing and/or treating diseases and conditions associated with decreased T-cell proliferation. Antibodies of the invention which block the binding of DR5 receptor ligands to DR5 receptors or interfere with DR5 receptor conformational changes associated with membrane signal transduction can inhibit DR5 mediated T-cell apoptosis. The inhibition of DR5 mediated apoptosis can, for examples, either result in an increase in the expansion rate of in vivo T-cell populations or prevent a decrease in the size of such populations. Thus, antagonists of the invention can be used to prevent and/or treat diseases or conditions associated with decreased or decreases in T-cell populations. Examples of such diseases and conditions included acquired immune deficiency syndrome (AIDS) and related afflictions (e.g., AIDS related complexes), T-cell immunodeficiencies, radiation sickness, and T-cell depletion due to radiation and/or chemotherapy.

When an antagonist of the invention is administered to an individual for the treatment and/or prevention of a disease or condition associated with decreased T-cell populations, the antagonist may be co-administered with an agent which activates and/or induces lymphocyte proliferation (e.g., a cytokine). Combination therapies of this nature, as well as other combination therapies, are discussed below in more detail.

Similarly, agonists and antagonists of the invention (e.g., anti-DR5 receptor antibodies) are also useful when administered alone or in combination with another therapeutic agent for either inhibiting or enhancing B-cell mediated immune responses, as well as preventing and/or treating diseases and conditions associated with increased or decreased B-cell proliferation.

Anti-DR5 antibodies are thus useful for treating and/or preventing malignancies, abnormalities, diseases and/or conditions involving tissues and cell types which express DR5 receptors (e.g., endothelial cells). Further, malignancies, abnormalities, diseases and/or conditions which can be treated and/or prevented by the induction of programmed cell death in cells which express DR5 receptors can be treated and/or prevented using DR5 receptor agonists of the invention. Similarly, malignancies, abnormalities, diseases and/or conditions which can be treated and/or prevented by inhibiting programmed cell death in cells which express DR5 receptors can be treated and/or prevented using DR5 receptor antagonists of the invention.

Further, antibodies of the invention, as well as other agonists, are useful for stimulating DR5 death domain activity in endothelial cells, resulting in anti-angiogenic activity. Antibodies of this type are useful for prevention and/or treating diseases and conditions associated with hypervascularization and neovascularization, such as rheumatoid arthritis and solid tissue cancers (e.g., skin cancer, head and neck tumors, breast tumors, endothelioma, osteoblastoma, osteoclastoma, and Kaposi's sarcoma), as well as diseases and conditions associated with chronic inflammation.

Diseases and conditions associated with chronic inflammation, such as ulcerative colitis and Crohn's disease, often show histological changes associated with the ingrowth of new blood vessels into the inflamed tissues. Agonists of the invention which stimulate the activity of DR5 death domains will induce apoptosis in endothelial cells which express these receptors. As a result, agonists of the invention can inhibit the formation of blood and lymph vessels and thus, can be used to prevent and/or treat diseases and conditions associated with hypervascularization and neovascularization.

Other diseases and conditions associated with angiogenesis which can be prevented and/or treated using agonists of the invention include hypertrophic and keloid scarring, proliferative diabetic retinopathy, arteriovenous malformations, atherosclerotic plaques, hemophilic joints, nonunion fractures, Osler-Weber syndrome, psoriasis, pyogenic granuloma, scleroderma, tracoma, menorrhagia, and vascular adhesions.

Further, agents which inhibit DR5 death domain activity (e.g. DR5 antagonists) are also useful for preventing and/or treating a number of diseases and conditions associated with decreased vascularization. As indicated above, examples of antagonists of DR5 receptor activity include anti-DR5 receptor antibodies. These antibodies can function, for examples, by either binding to DR5 receptors and blocking the binding of ligands which stimulate DR5 death domain activity (e.g., TRAIL) or inhibiting DR5 receptor conformational changes associated with membrane signal transduction.

An example of a condition associated with decreased vascularization that can be treated using antagonists of the invention is delayed wound healing. The elderly, in particular, often heal at a slower rate than younger individuals. Antagonists of the invention can thus prevent and/or inhibit apoptosis from occurring in endothelial cells at wound sites and thereby promote wound healing in healing impaired individuals, as well as in individuals who heal at "normal" rates. Thus, antagonists of the invention can be used to promote and/or accelerate wound healing. Antagonists of the invention are also useful for treating and/or preventing other diseases and conditions including restenosis, myocardial infarction, peripheral arterial disease, critical limb ischemia, angina, atherosclerosis, ischemia, edema, liver cirrhosis, osteoarthritis, and pulmonary fibrosis.

A number of additional malignancies, abnormalities, diseases and/or conditions which can be treated using the agonists and antagonists of the invention are set out elsewhere herein, for example, in the section below entitled "Therapeutics".

The antibodies of the present invention may be used therapeutically in a number of ways. For example, antibodies which bind polynucleotides or polypeptides of the present invention can be administered to an individual (e.g., a human) either locally or systemically. Further, these antibodies can be administered alone, in combination with another therapeutic agent, or associated with or bound to a toxin.

Anti-DR5 antibodies may be utilized in combination with other monoclonal or chimeric antibodies, or with lymphokines, tumor necrosis factors or TNF-related molecules (e.g., TNF-α, TNF-β, TNF-γ, TNF-γ-α, TNF-γ-β, and TRAIL), or hematopoietic growth factors (e.g., IL-2, IL-3 and IL-7). For example, agonistic anti-DR5 antibodies may be administered in conjunction with TRAIL when one seeks to induce DR5 mediated cell death in cells which express DR5 receptors of the invention. Combination therapies of this nature, as well as other combination therapies, are discussed below in more detail.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides, including fragments thereof Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{31\ 11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

Polypeptide Assays

The present invention also relates to diagnostic assays such as quantitative and diagnostic assays for detecting levels of DR5 protein, or the soluble form thereof, in cells and tissues, including determination of normal and abnormal levels. Thus, for instance, a diagnostic assay in accordance with the invention for detecting over-expression of DR5, or soluble form thereof, compared to normal control tissue samples may be used to detect the presence of tumors, for example. Assay techniques that can be used to determine levels of a protein, such as a DR5 protein of the present invention, or a soluble form thereof, in a sample derived from a host are well-known to those of skill in the art. Such assay methods include radioimmunoassays, competitive-binding assays, Western Blot analysis, and ELISA assays.

Assaying DR5 protein levels in a biological sample can occur using any art-known method. By "biological sample" is intended any biological sample obtained from an individual, cell line, tissue culture, or other source containing DR5 receptor protein or mRNA. Preferred for assaying DR5 protein levels in a biological sample are antibody-based techniques. For example, DR5 protein expression in tissues can be studied with classical immunohistological methods. (Jalkanen, M. et al., *J. Cell. Biol.* 101:976–985

(1985); Jalkanen, M. et al., *J. Cell. Biol.* 105:3087–3096 (1987)). Other antibody-based methods useful for detecting DR5 protein gene expression include immunoassays, such as the enzyme linked immunosorbent assay (ELISA) and the radioimmunoassay (RIA).

Suitable labels are known in the art and include enzyme labels, such as glucose oxidase, radioisotopes, such as iodine ($^{125}$I, $^{121}$I), carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

Therapeutics

The Tumor Necrosis Factor (TNF) family ligands are known to be among the most pleiotropic cytokines, inducing a large number of cellular responses, including cytotoxicity, anti-viral activity, immunoregulatory activities, and the transcriptional regulation of several genes (Goeddel, D. V. et al., "Tumor Necrosis Factors Gene Structure and Biological Activities," *Symp. Quant. Biol.* 51:597–609 (1986), Cold Spring Harbor; Beutler, B., and Cerami, A., *Annu. Rev. Biochem.* 57:505–518 (1988); Old, L. J., *Sci. Am.* 258:59–75 (1988); Fiers, W., *FEBS Lett.* 285:199–224 (1991)). The TNF-family ligands induce such various cellular responses by binding to TNF-family receptors, including the DR5 of the present invention.

DR5 polynucleotides, polypeptides, agonists and/or antagonists of the invention may be administered to a patient (e.g., mammal, preferably human) afflicted with any disease or disorder mediated (directly or indirectly) by defective, or deficient levels of, DR5. Alternatively, a gene therapy approach may be applied to treat and/or prevent such diseases or disorders. In one embodiment of the invention, DR5 polynucleotide sequences are used to detect mutein DR5 genes, including defective genes. Mutein genes may be identified in in vitro diagnostic assays, and by comparison of the DR5 nucleotide sequence disclosed herein with that of a DR5 gene obtained from a patient suspected of harboring a defect in this gene. Defective genes may be replaced with normal DR5-encoding genes using techniques known to one skilled in the art.

In another embodiment, the DR5 polypeptides, polynucleotides, agonists and/or antagonists of the present invention are used as research tools for studying the phenotypic effects that result from inhibiting TRAIL/DR5 interactions on various cell types. DR5 polypeptides and antagonists (e.g. monoclonal antibodies to DR5) also may be used in in vitro assays for detecting TRAIL or DR5 or the interactions thereof.

It has been reported that certain ligands of the TNF family (of which TRAIL is a member) bind to more than one distinct cell surface receptor protein. For example, a receptor protein designated DR4 reportedly binds TRAIL, but is distinct from the DR5 of the present invention (Pan et al., *Science* 276: 111–113, (1997); hereby incorporated by reference). In another embodiment, a purified DR5 polypeptide, agonist and/or antagonist is used to inhibit binding of TRAIL to endogenous cell surface TRAIL. By competing for TRAIL binding, soluble DR5 polypeptides of the present invention may be employed to inhibit the interaction of TRAIL not only with cell surface DR5, but also with TRAIL receptor proteins distinct from DR5. Thus, in a further embodiment, DR5 polynucleotides, polypeptides, agonists and/or antagonists of the invention are used to inhibit a functional activity of TRAIL, in in vitro or in vivo procedures. By inhibiting binding of TRAIL to cell surface receptors, DR5 also inhibits biological effects that result from the binding of TRAIL to endogenous receptors. Various forms of DR5 may be employed, including, for example, the above-described DR5 fragments, derivatives, and variants that are capable of binding TRAIL. In a preferred embodiment, a soluble DR5, is employed to inhibit a functional activity of TRAIL, e.g., to inhibit TRAIL-mediated apoptosis of cells susceptible to such apoptosis. Thus, in an additional embodiment, DR5 is administered to a mammal (e.g., a human) to treat and/or prevent a TRAIL-mediated disorder. Such TRAIL-mediated disorders include conditions caused (directly or indirectly) or exacerbated by TRAIL.

Cells which express the DR5 polypeptide and are believed to have a potent cellular response to DR5 ligands include primary dendritic cells, endothelial tissue, spleen, chronic lymphocytic leukemia, and human thymus stromal cells. By "a cellular response to a TNF-family ligand" is intended any genotypic, phenotypic, and/or morphologic change to a cell, cell line, tissue, tissue culture or patient that is induced by a TNF-family ligand. As indicated, such cellular responses include not only normal physiological responses to TNF-family ligands, but also diseases associated with increased apoptosis or the inhibition of apoptosis. Apoptosis (programmed cell death) is a physiological mechanism involved in the deletion of peripheral T lymphocytes of the immune system, and its dysregulation can lead to a number of different pathogenic processes (Ameisen, J. C., *AIDS* 8:1197–1213 (1994); Krammer, P. H. et al, *Curr. Opin. Immunol.* 6:279–289 (1994)).

Diseases associated with increased cell survival, or the inhibition of apoptosis, that may be treated, prevented, diagnosed and/or prognosed with the DR5 polynucleotides, polypeptides and/or agonists or antagonists of the invention include, but are not limited to, include cancers (such as follicular lymphomas, carcinomas with p53 mutations, and hormone-dependent tumors including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, DR5 polynucleotides, polypeptides, and/or antagonists of the invention are used to inhibit growth, progression, and/or metastasis of cancers, in particular those listed above.

Additional diseases or conditions associated with increased cell survival that may be treated, prevented, diagnosed and/or prognosed with the DR5 polynucleotides, polypeptides and/or agonists or antagonists of the invention include, but are not limited to, progression, and/or metastases of malignancies and related disorders such as leukemia (including acute leukemias (e.g. acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that may be treated, prevented, diagnosed and/or prognosed with the DR5 polynucleotides, polypeptides and/or agonists or antagonists of the invention include, but are not limited to, AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia. In preferred embodiments, DR5 polynucleotides, polypeptides and/or agonists are used to treat and/or prevent the diseases and disorders listed above.

The state of Immunodeficiency that defines AIDS is secondary to a decrease in the number and function of CD4+ T-lymphocytes. Recent reports estimate the daily loss of CD4+ T-cells to be between $3.5 \times 10^7$ and $2 \times 10^9$ cells (Wei X. et al., *Nature* 373:117–122 (1995)). One cause of CD4+ T-cell depletion in the setting of HIV infection is believed to be HIV-induced apoptosis (see, for example, Meyaard et al., *Science* 257:217–219, 1992; Groux et al., *J Exp. Med.*, 175:331, 1992; and Oyaizu et al., in *Cell Activation and Apoptosis ill HIV Infection*, Andrieu and Lu, Eds., Plenum Press, New York, 1995, pp. 101–114). Indeed, HIV-induced apoptotic cell death has been demonstrated not only in vitro but also, more importantly, in infected individuals (Ameisen, J. C., *AIDS* 8:1197–1213 (1994); Finkel, T. H., and Banda, N. K., *Curr. Opin. Immunol.* 6:605–615(1995); Muro-Cacho, C. A. et al, *J. Immunol.* 154:5555–5566 (1995)). Furthermore, apoptosis and CD4+ T-lymphocyte depletion is tightly correlated in different animal models of AIDS (Brunner, T., et al., *Nature* 373:441–444 (1995); Gougeon, M. L., et al, *AIDS Res. Hum. Retroviruses* 9:553–563 (1993)) and, apoptosis is not observed in those animal models in which viral replication does not result in AIDS (Gougeon, M. L. et al., *AIDS Res. Hum. Retroviruses* 9:553–563 (1993)). Further data indicates that uninfected but primed or activated T lymphocytes from HIV-infected individuals undergo apoptosis after encountering the TNF-family ligand FasL. Using monocytic cell lines that result in death following HIV infection, it has been demonstrated that infection of U937 cells with HIV results in the de novo expression of FasL and that FasL mediates HIV-induced apoptosis (Badley, A.D. et al., *J. Virol.* 70:199–206 (1996)). Further the TNF-family ligand was detectable in uninfected macrophages and its expression was upregulated following HIV infection resulting in selective killing of uninfected CD4 T-lymphocytes (Badley, A. D et al., *J. Virol.* 70–199–206 (1996)). Further. additional studies have implicated Fas-mediated apoptosis in the loss of T-cells in HIV individuals (Katsikis et al., *J. Exp. Med.* 181:2029–2036, 1995).

Thus, by the invention, a method for treating and/or preventing HIV+ individuals is provided which involves administering DR5, DR5 antagonists, and/or DR5 agonists of the present invention to reduce selective killing of $CD^{4+}$ T-lymphocytes. Modes of administration and dosages are discussed in detail below.

In rejection of an allograft, the immune system of the recipient animal has not previously been primed to respond because the immune system for the most part is only primed by environmental antigens. Tissues from other members of the same species have not been presented in the same way that, for example, viruses and bacteria have been presented. In the case of allograft rejection, immunosuppressive regimens are designed to prevent the immune system from reaching the effector stage. However, the immune profile of xenograft rejection may resemble disease recurrence more than allograft rejection. In the case of disease recurrence, the immune system has already been activated, as evidenced by destruction of the native islet cells. Therefore, in disease recurrence the immune system is already at the effector stage. Agonists of the present invention are able to suppress the immune response to both allografts and xenografts because lymphocytes activated and differentiated into effector cells will express the DR5 polypeptide, and thereby are susceptible to compounds which enhance apoptosis. Thus, the present invention further provides a method for creating immune privileged tissues.

DR5 antagonists or agonists of the invention may be useful for treating and/or preventing inflammatory diseases, such as rheumatoid arthritis, osteoarthritis, psoriasis, septicemia, and inflammatory bowel disease.

In addition, due to lymphoblast expression of DR5, soluble DR5 agonist or antagonist mABs may be used to treat and/or prevent this form of cancer. Further, soluble DR5 or neutralizing mABs may be used to treat and/or prevent various chronic and acute forms of inflammation such as rheumatoid arthritis, osteoarthritis, psoriasis, septicemia, and inflammatory bowel disease.

Polynucleotides and/or polypeptides of the invention and/or agonists and/or antagonists thereof are useful in the diagnosis, prognosis, treatment and/or prevention of a wide range of diseases and/or conditions. Such diseases and conditions include, but are not limited to, cancer (e.g., immune cell related cancers, breast cancer, prostate cancer, ovarian cancer, follicular lymphoma, glioblastoma, cancer associated with mutation or alteration of p53, brain tumor, bladder cancer, uterocervical cancer, colon cancer, colorectal cancer, non-small cell carcinoma of the lung, small cell carcinoma of the lung, stomach cancer, etc.), lymphoproliferative disorders (e.g., lymphadenopathy and lymphomas (e.g., Hodgkin's disease)), microbial (e.g., viral, bacterial, etc.) infection (e.g., HIV-1 infection, HIV-2 infection, herpesvirus infection (including, but not limited to, HSV-1, HSV-2, CMV, VZV, HHV-6, HHV-7, EBV), adenovirus infection, poxvirus infection, human papilloma virus infection, hepatitis infection (e.g., HAV, HBV, HCV, etc.), *Helicobacter pylori* infection, invasive Staphylococcia, etc.), parasitic infection, nephritis, bone disease (e.g., osteoporosis), atherosclerosis, pain, cardiovascular disorders (e.g., neovascularization, hypovascularization or reduced circulation (e.g., ischemic disease (e.g., myocardial infarction, stroke, etc.)), AIDS, allergy, inflammation, neurodegenerative disease (e.g., Alzheimer's disease, Parkinson's disease, amyotrophic lateral sclerosis, pigmentary retinitis, cerebellar degeneration, etc.), graft rejection (acute and chronic), graft vs. host disease, diseases due to osteomyelodysplasia (e.g., aplastic anemia, etc.), joint tissue destruction in rheumatism, liver disease (e.g., acute and chronic hepatitis, liver injury, and cirrhosis), autoimmune disease (e.g., multiple sclerosis, myasthenia gravis, rheumatoid arthritis, systemic lupus erythematosus, immune complex glomerulonephritis, autoimmune diabetes, autoimmune thrombocytopenic purpura, Grave's disease, Hashimoto's thyroiditis, inflammatory autoimmune diseases, etc.), cardiomyopathy (e.g., dilated cardiomyopathy), diabetes, diabetic complications (e.g., diabetic nephropathy, diabetic neuropathy, diabetic retinopathy), influenza, asthma, psoriasis, osteomyelitis, glomerulonephritis, septic shock, and ulcerative colitis.

Polynucleotides and/or polypeptides of the invention and/or agonists and/or antagonists thereof are useful in promoting regulating hematopoiesis, regulating (e.g., promoting) angiogenesis, wound healing (e.g., wounds, burns, and bone fractures), and regulating bone formation.

DR5 polynucleotides or polypeptides, or agonists of DR5, can be used in the treatment and/or prevention of infectious agents. For example, by increasing the immune response, particularly increasing the proliferation and differentiation of B-cells in response to an infectious agent, infectious diseases may be treated and/or prevented. The immune response may be increased by either enhancing an existing immune response, or by initiating a new immune response. Alternatively, DR5 polynucleotides or polypeptides, or agonists or antagonists of DR5, may also directly inhibit the infectious agent, without necessarily eliciting an immune response.

Viruses are one example of an infectious agent that can cause disease or symptoms that can be treated and/or prevented by DR5 polynucleotides or polypeptides, or agonists of DR5. Examples of viruses, include, but are not limited to the following DNA and RNA viruses and viral families: arbovirus. adenoviridae, arenaviridae, arterivirus, birnaviridae, bunyaviridae, caliciviridae. circoviridae, coronaviridae, Dengue virus, HIV-1, HIV-2, flaviviridae. hepadnaviridae (e.g., hepatitis B virus), herpesviridae (e.g., cytomegalovirus, herpes simplex viruses 1 and 2, varicella-zoster virus, Epstein-Barr virus (EBV), herpes B virus, and human herpesviruses 6, 7, and 8), morbillivirus, rhabdoviridae (e.g., rabies virus), orthomyxoviridae (e.g., influenza A virus, and influenza B), paramyxoviridae (e.g., parainfluenza virus), papilloma virus. papovaviridae, parvoviridae, picornaviridae (e.g., EMCV and poliovirus). poxviridae (e.g., variola or vaccinia virus), reoviridae (e.g., rotavirus). retroviridae (HTLV-I, HTLV-II, lentivirus), and togaviridae (e.g., rubivirus) These viruses and virus families can cause a variety of diseases or symptoms, including, but not limited to: arthritis, bronchiollitis, respiratory diseases, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, smallpox, opportunistic infections (e.g., AIDS, Kaposi's sarcoma), pneumonia, Burkitt's lymphoma, chickenpox, zoster, hemorrhagic fever, measles, mumps. parainfluenza, rabies, the common cold, polio, leukemia, rubella, sexually transmitted diseases, skin diseases (e.g., Kaposi's, warts), and viremia, DR5 polynucleotides or polypeptides, or agonists or antagonists of DR5, can be used to treat, prevent, and/or detect any of these symptoms or diseases. In specific embodiments, DR5 polynucleotides, polypeptides, or agonists are used to treat and/or prevent: meningitis, Dengue, EBV, and/or hepatitis. In an additional specific embodiment DR5 polynucleotides, polypeptides, or agonists are used to treat patients non-responsive to one or more other commercially available hepatitis vaccines. In a further specific embodiment, DR5 polynucleotides, polypeptides, or agonists are used to treat AIDS.

Similarly, bacteria and fungi that can cause disease or symptoms and that can be treated and/or prevented by DR5 polynucleotides or polypeptides, or agonists or antagonists of DR5, include, but are not limited to the following organisms. Bacteria include, but are not limited to Actinonmyces, Bacillus (e.g., *B. anthracis*), Bacteroides, Bordetella, Bartonella, Borrelia (e.g., *B. burgdorferi*), Brucella, Campylobacter, Capnocytophaga, Chlamydia, Clostridium, Corynebacterium, Coxiella, Dermatophilus, Enterococcus, Ehrlichia, Escherichia (e.g., enterotoxigenic *E. coli* and enterohemorrhagic *E. coli*), Francisella, Fusobacteriurn, Haemobartonella, Haemophilus (e.g. *H. influenzae* type b), Helicobacter, Klebsiella, L-form bacteria, Legionella, Leptospira, Listeria, Mycobacteria (e.g., *M. leprae* and *M. tuberculosis*), Mycoplasma, Neisseria (e.g., *N. gonorrheae* and *N. meningitidis*), Neorickettsia, Nocardia, Pasteurella, Peptococcus, Peptostreptococcus, Pneumococcus, Proteus, Pseudomnonas, Rickettsia, Rochalimaea, Salmonella (e.g., *S. typhimurium* and *S. typhi*), Seratia, Shigella, Staphylococcus (e.g., *S. aureus*), Streptococcus (e.g., *S. pyogenes, S. pneumoniae*, and Group B streptococcus), Streptomyces, Treponema, Vibrio (e.g., *Vibrio cholerae*) and Yersinia (e.g., *Y. pestis*). Fungi include, but are not limited to: Absidia, Acremonium, Alternaria, Aspergillus, Basidiobolus, Bipolaris, Blastomyces, Candida (e.g., *C. albicans*), Coccidioides, Conidiobolus, Cryptococcus (e.g., *C. neoformans*), Curvalaria, Erysipelothrix, Epidermophyton, Exophiala, Geotrichumn, Histoplasma, Madurella, Malassezia, Microsporum, Monihella, Mortierella, Mucor, Paecilomyces, Penicillium, Phialemonium, Phialophora, Prototheca, Pseudallescheria, Pseudomicrodochium, Pythium, Rhinosporidium, Rhizopus, Scolecobasidium, Sporothrix, Stemphylium, Trichophyton, Trichosporon, and Xylohypha. These and other bacteria or fungi can cause diseases or symptoms including, but not limited to: bacteremia, endocarditis, eye infections (conjunctivitis, uveitis), gingivitis, opportunistic infections (e.g., AIDS related infections), paronychia, prosthesis-related infections, Reiter's Disease, respiratory tract infections, such as whooping cough or emphysema, sepsis, Lyme Disease, cat-scratch disease, dysentery, paratyphoid fever, food poisoning, typhoid, pneumonia, gonorrhea, meningitis, chlamydia, syphilis, diphtheria, leprosy, paratuberculosis, tuberculosis, lupus, botulism, gangrene, tetanus, impetigo, rheumatic fever, scarlet fever, sexually transmitted diseases, skin diseases (e.g., cellulitis, dermatocycoses), toxemia, urinary tract infections, and wound infections. DR5 polynucleotides or polypeptides, or agonists or antagonists of DR5, can be used to treat, prevent and/or detect any of these symptoms or diseases. In specific embodiments, DR5 polynucleotides, polypeptides, or agonists thereof are used to treat and/or prevent: tetanus, diphtheria, botulism, and/or meningitis type B.

Moreover, parasites causing parasitic diseases or symptoms that can be treated and/or prevented by DR5 polynucleotides or polypeptides, or agonists of DR5, include, but are not limited to: protozoan parasites including, but not limited to, Babesia, Balantidium, Besnoitia, Cryptosporidium, Eimeria, Encephalitozoon, Entamoeba, Giardia, Hammondia, Hepatozoon, Isospora, Leishmania, Microsporidia, Neospora, Nosema, Pentatrichomonas, Plasmodium (e.g., *Plasmodium virax, Plasmodium falciparium, Plasmodium malariae* and *Plasmodium ovale*), Pneumocystis, Sarcocystis, Schistosoma, Theileria, Toxoplasma, and Trypanosoma; and helminth parasites including, but not limited to, Acanthocheilonema, Aelurostrongylus, Ancylostoma, Angiostrongylus, Ascaris, Brugia, Bunostomum, Capillaria, Chabertia, Cooperia, Crenosoma, Dictyocaulus, Dioctophyme, Dipetalonema, Diphyllobothrium, Diplydium, Dirofilaria, Dracunculus, Enterobius, Filaroides, Haermonchus, Lagochilascaris, Loa, Mansonella, Muellerius, Nanophyetus, Necator, Nematodirus, Oesophagostomum, Onchocerca, Opisthorchis, Ostertagia, Parafilaria, Paragonimus, Parascaris, Physaloptera, Protostrongylus, Setaria, Spirocerca, Spirometra, Stephanofilaria, Strongyloides, Strongylus, Thelazia, Toxascaris, Toxocara, Trichinella, Trichostrongylus, Trichuris, Uncinaria, and Wuchereria. These parasites can cause a variety of diseases or symptoms, including, but not limited to: scabies, trombiculiasis, eye infections (e.g., river blindness), elephantiasis, intestinal disease (e.g., dysentery, giardiasis), liver disease, lung disease, opportunistic infections (e.g., AIDS related), malaria, pregnancy complications, and toxoplasmosis. DR5 polynucleotides or polypeptides, or agonists or antagonists of DR5, can be used to treat, prevent and/or detect any of these symptoms or diseases. In specific embodiments. DR5 polynucleotides, polypeptides, or agonists thereof are used to treat and/or prevent malaria.

Polynucleotides and/or polypeptides of the invention and/or agonists and/or antagonists thereof are also useful as a vaccine adjuvant to enhance immune responsiveness to specific antigen, tumor-specific, and/or anti-viral immune responses.

An adjuvant to enhance anti-viral immune responses. Anti-viral immune responses that may be enhanced using the compositions of the invention as an adjuvant, include virus and virus associated diseases or symptoms described herein or otherwise known in the art. In specific embodiments, the compositions of the invention are used as an adjuvant to enhance an immune response to a virus, disease, or symptom selected from the group consisting of: AIDS, meningitis, Dengue, EBV, and hepatitis (e.g., hepatitis B). In another specific embodiment, the compositions of the invention are used as an adjuvant to enhance an immune response to a virus, disease, or symptom selected from the group consisting of: HIV/AIDS, Respiratory syncytial virus, Dengue, Rotavirus, Japanese B encephalitis, Influenza A and B, Parainfluenza, Measles, Cytomegalovirus, Rabies, Junin, Chikungunya, Rift Valley fever, Herpes simplex virus, and yellow fever.

Anti-bacterial or anti-fungal immune responses that may be enhanced using the compositions of the invention as an adjuvant, include bacteria or fungus and bacteria or fungus associated diseases or symptoms described herein or otherwise known in the art. In specific embodiments, the compositions of the invention are used as an adjuvant to enhance an immune response to a bacteria or fungus, disease, or symptom selected from the group consisting of: tetanus, diphtheria, botulism, and meningitis type B. In another specific embodiment, the compositions of the invention are used as an adjuvant to enhance an immune response to a bacteria selected from the group consisting of: *Vibrio cholerae, Mycobacterium leprae, Salmonella typhi, Salmonella paratyphi, Neisseria meningitidis, Streptococcus pneumoniae,* Group B streptococcus, Shigella spp., enterotoxigenic *E. coli,* enterohemorrhagic *E. coli,* and *Borrelia burgdorferi.*

Anti-parasitic immune responses that may be enhanced using the compositions of the invention as an adjuvant, include parasite and parasite associated diseases or symptoms described herein or otherwise known in the art. In specific embodiments, the compositions of the invention are used as an adjuvant to enhance an immune response to a parasite. In another specific embodiment, the compositions of the invention are used as an adjuvant to enhance an immune response to Plasmodium spp. (malaria).

More generally, DR5 polynucleotides and/or polypeptides of the invention and/or agonists and/or antagonists thereof are useful in regulating (I. e., elevating or reducing) immune response. For example, polynucleotides and/or polypeptides of the invention may be useful in preparation or recovery from surgery, trauma, radiation therapy, chemotherapy, and transplantation. Further, polynucleotides and/or polypeptides of the invention may be may be used to boost immune response and/or accelerate recovery in the elderly and immunocompromised individuals, or as an agent that elevates the immune status of an individual prior to their receipt of immunosuppressive therapies. Also, polynucleotides and/or polypeptides of the invention may be useful as an agent to induce higher affinity antibodies, or to increase serum immunoglobulin concentrations.

In one embodiment, DR5 polynucleotides and/or polypeptides of the invention and/or agonists thereof may be used as an immune system enhancer prior to, during, or after bone marrow transplant and/or other transplants (e.g., allogenic or xenogenic organ transplantation). With respect to transplantation, compositions of the invention may be administered prior to, concomitant with, and/or after transplantation. In a specific embodiment, compositions of the invention are administered after transplantation, prior to the beginning of recovery of T-cell populations. In another specific embodiment, compositions of the invention are first administered after transplantation after the beginning of recovery of T-cell populations, but prior to full recovery of B-cell populations.

In another embodiment, DR5 polynucleotides and/or polypeptides of the invention and/or agonists thereof may be used as an agent to boost immunoresponsiveness among B-cell immunodeficient individuals. B-cell immunodeficiencies that may be ameliorated or treated and/or prevented by administering the DR5 polypeptides or polynucleotides of the invention, or agonists thereof, include, but are not limited to, severe combined immune deficiency (SCID), congenital agammaglobulinemia, common variable immunodeficiency, Wiskott-Aldrich Syndrome, and X-linked immunodeficiency with hyper IgM.

Additionally, DR5 polynucleotides and/or polypeptides of the invention and/or agonists thereof may be used as an agent to boost immunoresponsiveness among individuals having an acquired loss of B-cell function. Conditions resulting in an acquired loss of B-cell function that may be ameliorated, treated, and/or prevented by administering the DR5 polypeptides or polynucleotides of the invention, or agonists thereof, include, but are not limited to, HIV Infection, AIDS, bone marrow transplant, and B-cell chronic lymphocytic leukemia (CLL)

Furthermore, DR5 polynucleotides and/or polypeptides of the invention and/or agonists thereof may be used as an agent to boost immunoresponsiveness among individuals having a temporary immune deficiency. Conditions resulting in a temporary immune deficiency that may be ameliorated, treated, and/or prevented by administering the DR5 polypeptides or polynucleotides of the invention, or agonists thereof, include, but are not limited to, recovery from viral infections (e.g., influenza), conditions associated with malnutrition, recovery from infectious mononucleosis, or conditions associated with stress, recovery from measles, recovery from blood transfusion, recovery from surgery.

DR5 polynucleotides and/or polypeptides of the invention and/or agonists thereof may also be used as a regulator of antigen presentation by monocytes, dendritic cells, and/or B-cells. In one embodiment, DR5 (in soluble, membrane-bound or transmembrane forms) enhances antigen presentation or antagonizes antigen presentation in vitro or in vivo.

In related embodiments, said enhancement or antagonization of antigen presentation may be useful as an anti-tumor treatment or to modulate the immune system. For example, DR5 polynucleotides and/or polypeptides of the invention and/or agonists thereof may be used as an agent to direct an individuals immune system towards development of a humoral response (i.e. TH2) as opposed to a TH1 cellular response. Also, DR5 polynucleotides and/or polypeptides of the invention and/or agonists thereof may be used as a stimulator of B-cell production in pathologies such as AIDS, chronic lymphocyte disorder and/or Common Variable Immunodeficiency.

In another embodiment, DR5 polynucleotides and/or polypeptides of the invention and/or agonists thereof may be used as a means to induce tumor proliferation and thus make the tumor more susceptible to anti-neoplastic agents. For example, multiple myeloma is a slowly dividing disease and is thus refractory to virtually all anti-neoplastic regimens. If these cells were forced to proliferate more rapidly their susceptibility profile would likely change.

Other embodiments where DR5 polynucleotides and/or polypeptides of the invention and/or agonists thereof may be used include, but are not limited to: as a stimulator of B-cell production in pathologies such as AIDS, chronic lymphocyte disorder and/or Common Variable Immunodeficiency; as a therapy for generation and/or regeneration of lymphoid tissues following surgery, trauma or genetic defect; as a gene-based therapy for genetically inherited disorders resulting in immuno-incompetence such as observed among SCID patients; as an antigen for the generation of antibodies to inhibit or enhance DR5 mediated responses; as a means of activating T-cells; as pretreatment of bone marrow samples prior to transplant (such treatment would increase B-cell representation and thus accelerate recovery); as a means of regulating secreted cytokines that are elicited by DR5; to modulate IgE concentrations in vitro or in vivo; and to treat and/or prevent IgE-mediated allergic reactions including, but are not limited to, asthma, rhinitis, and eczema.

Alternatively, DR5 polynucleotides and/or polypeptides of the invention and/or agonists and/or antagonists thereof are useful as immunosuppressive agents, for example in the treatment and/or prevention of autoimmune disorders In specific embodiments, polynucleotides and/or polypeptides of the invention are used to treat and/or prevent chronic inflammatory, allergic or autoimmune conditions, such as those described herein or are otherwise known in the art.

Preferably, treatment using DR5 polynucleotides or polypeptides, or agonists of DR5, could either be by administering an effective amount of DR5 polypeptide to the patient, or by removing cells from the patient, supplying the cells with DR5 polynucleotide, and returning the engineered cells to the patient (ex vivo therapy). Moreover, as further discussed herein, the DR5 polypeptide or polynucleotide can be used as an adjuvant in a vaccine to raise an immune response against infectious disease.

Additional preferred embodiments of the invention include, but are not limited to, the use of DR5 polypeptides and functional agonists in the following applications: administration to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantities of one or more antibodies (e.g., IgG, IgA, IgM, and IgE), to induce higher affinity antibody production (e.g., IgG, IgA, IgM, and IgE), and/or to increase an immune response; or administration to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconstituted immune system from another animal (see, e.g., published PCT Application Nos. WO98/24893, WO96/34096, WO96/33735, and WO91/10741.

Antagonists of DR5 include binding and/or inhibitory antibodies, antisense nucleic acids, ribozymes or soluble forms of the DR5 receptor(s). These would be expected to reverse many of the activities of herein, as well as find clinical or practical application including, but not limited to the following applications. DR5 antagonists may be used as a means of blocking various aspects of immune responses to foreign agents or self, for example, autoimmune disorders such as lupus, and arthritis, as well as immunoresponsiveness to skin allergies, inflammation, bowel disease, injury and pathogens. Although our current data speaks directly to the potential role of DR5 in B-cell and T-cell related pathologies, it remains possible that other cell types may gain expression or responsiveness to DR5. Thus, DR5 may, like CD40 and its ligand, may be regulated by the status of the immune system and the microenvironment in which the cell is located. DR5 antagonists may be used as a therapy for preventing the B-cell proliferation and Ig secretion associated with autoimmune diseases such as idiopathic thrombocytopenic purpura, systemic lupus erythramatosus and; as an inhibitor of graft versus host disease or transplant rejection; as a therapy for B-cell malignancies such as ALL, Hodgkins disease, non-Hodgkins lymphoma, Chronic lymphocyte leukemia, plasmacytomas, multiple myeloma, Burkitt's lymphoma, and EBV-transformed diseases; as a therapy for chronic hypergammaglobulinemeia evident in such diseases as monoclonalgammopathy of undetermined significance (MGUS), Waldenstrom's disease, related idiopathic monoclonalgammopathies, and plasmacytomas; as a therapy for decreasing cellular proliferation of Large B-cell Lymphomas; as a means of decreasing the involvement of B-cells and Ig associated with Chronic Myelogenous Leukemia; or as an immunosuppressive agent.

Furthermore, DR5 polypeptides or polynucleotides of the invention, or antagonists thereof may be used to modulate IgE concentrations in vitro or in vivo, or to treat and/or prevent IgE-mediated allergic reactions including, but not limited to, asthma, rhinitis, and eczema.

All of the therapeutic applications of DR5 polynucleotides and/or polypeptides of the invention and/or agonists and/or antagonists thereof described herein may, in addition to their uses in human medicine, be used in veterinary medicine. The present invention includes treatment of companion animals, including, but not limited to dogs, cats, ferrets, birds, and horses; food animals, including, but not limited to cows, pigs, chickens, and sheep; and exotic animals, e.g., zoo animals.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

DR5 polynucleotides and/or polypeptides of the invention and/or agonists and/or antagonists thereof described herein may be employed in a composition with a pharmaceutically acceptable carrier, e.g., as described herein.

In one aspect, the present invention is directed to a method for enhancing apoptosis induced by a TNF-family ligand, which involves administering to a cell which expresses the DR5 polypeptide an effective amount of DR5 ligand, analog or an agonist capable of increasing DR5 mediated signaling. Preferably, DR5 mediated signaling is increased to treat and/or prevent a disease wherein decreased apoptosis or decreased cytokine and adhesion molecule expression is exhibited. An agonist can include soluble forms of DR5 and monoclonal antibodies directed against the DR5 polypeptide.

In a further aspect, the present invention is directed to a method for inhibiting apoptosis induced by a TNF-family ligand, which involves administering to a cell which expresses the, DR5 polypeptide an effective amount of an antagonist capable of decreasing DR5 mediated signaling. Preferably, DR5 mediated signaling is decreased to treat and/or prevent a disease wherein increased apoptosis or NF-kB expression is exhibited. An antagonist can include soluble forms of DR5 (e.g., polypeptides containing all or a portion of the DR5 extracellular domain) and monoclonal antibodies directed against the DR5 polypeptide.

By "agonist" is intended naturally occurring and synthetic compounds capable of enhancing or potentiating apoptosis. By "antagonist" is intended naturally occurring and synthetic compounds capable of inhibiting apoptosis. Whether any candidate "agonist" or "antagonist" of the present invention can enhance or inhibit apoptosis can be determined using art-known TNF-family ligand/receptor cellular response assays, including those described in more detail below.

One such screening procedure involves the use of melanophores which are transfected to express the receptor of the present invention. Such a screening technique is described in PCT WO92/01810, published Feb. 6, 1992. Such an assay may be employed, for example, for screening for a compound which inhibits (or enhances) activation of the receptor polypeptide of the present invention by contacting the melanophore cells which encode the receptor with both a TNF-family ligand and the candidate antagonist (or agonist). Inhibition or enhancement of the signal generated by the ligand indicates that the compound is an antagonist or agonist of the ligand/receptor signaling pathway.

Other screening techniques include the use of cells which express the receptor (for example, transfected CHO cells) in a system which measures extracellular pH changes caused by receptor activation. For example, compounds may be contacted with a cell which expresses the receptor polypeptide of the present invention and a second messenger response, e.g., signal transduction or pH changes, may be measured to determine whether the potential compound activates or inhibits the receptor.

Another such screening technique involves introducing RNA encoding the receptor into Xenopus oocytes to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another screening technique involves expressing in cells a construct wherein the receptor is linked to a phospholipase C or D. Such cells include endothelial cells, smooth muscle cells, embryonic kidney cells, etc. The screening may be accomplished as herein above described by detecting activation of the receptor or inhibition of activation of the receptor from the phospholipase signal.

Another method involves screening for compounds (antagonists) which inhibit activation of the receptor polypeptide of the present invention by determining inhibition of binding of labeled ligand to cells which have the receptor on the surface thereof. Such a method involves transfecting a eukaryotic cell with DNA encoding the receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors If the compound binds to the receptor as determined by a reduction of labeled ligand which binds to the receptors, the binding of labeled ligand to the receptor is inhibited Further screening assays for agonist and antagonist of the present invention are described in Tartaglia, L. A., and Goeddel, D. V., *J. Biol. Chem.* 267:4304–4307(1992).

Thus, in a further aspect, a screening method is provided for determining whether a candidate agonist or antagonist is capable of enhancing or inhibiting a cellular response to a TNF-family ligand. The method involves contacting cells which express the DR5 polypeptide with a candidate compound and a TNF-family ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By "assaying a cellular response" is intended qualitatively or quantitatively measuring a cellular response to a candidate compound and/or a TNF-family ligand (e.g., determining or estimating an increase or decrease in T-cell or B-cell proliferation, or tritiated thymidine labeling). By the invention, a cell expressing the DR5 polypeptide can be contacted with either an endogenous or exogenously administered TNF-family ligand.

Agonist according to the present invention include naturally occurring and synthetic compounds such as, for example, TNF family ligand peptide fragments, transforming growth factor, neurotransmitters (such as glutamate, dopamine, N-methyl-D-aspartate), tumor suppressors (p53), cytolytic T-cells and antimetabolites. Preferred agonists include chemotherapeutic drugs such as, for example, cisplatin, doxorubicin, bleomycin, cytosine arabinoside, nitrogen mustard, methotrexate and vincristine. Others include ethanol and β-amyloid peptide. (*Science* 267:1457–1458 (1995)). Further preferred agonist include polyclonal and monoclonal antibodies raised against the DR5 polypeptide, or a fragment thereof. Such agonist antibodies raised against a TNF-family receptor are disclosed in Tartaglia, L. A., et al., *Proc. Natl. Acad. Sci. USA* 88:9292–9296 (1991); and Tartaglia, L. A., and Goeddel, D. V., *J. Biol. Chem.* 267 (7):4304–4307 (1992) See, also, PCT Application WO 94/09137.

Antagonist according to the present invention include naturally occurring and synthetic compounds such as, for example, the CD40 ligand, neutral amino acids, zinc, estrogen, androgens, viral genes (such as Adenovirus ElB, Baculovirus p35 and IAP, Cowpox virus crmA, Epstein-Barr virus BHRF1, LMP-1, African swine fever virus LMW5-HL, and Herpesvirus yl 34.5), calpain inhibitors, cysteine protease inhibitors, and tumor promoters (such as PMA, Phenobarbital, and alpha-Hexachlorocyclohexane).

Other potential antagonists include antisense molecules. Antisense technology can be used to control gene expression through antisense DNA or RNA or through triple-helix formation. Antisense techniques are discussed, for example, in Okano, *J. Neurochem.* 56:560 (1991); *Oligodeoxynucleotides as Antisense Inhibitors of Gene Expression*, CRC Press, Boca Raton, Fla. (1988). Triple helix formation is discussed in, for instance Lee et al., *Nucleic Acids Research* 6:3073 (1979); Cooney et al, Science 241:456 (1988); and Dervan et al., Science 251:1360 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide. The oligonucleotides described above can also be delivered to cells such that the antisense RNA or DNA may be expressed in vivo to inhibit production of the DR5 receptor.

In one embodiment, the DR5 antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the DR5 antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding DR5, or fragments thereof, can be by any promoter known in the art to act in vertebrate, preferably human cells. Such promoters can be inducible or a constitutive. Such promoters include, but are not limited to, the SV40 early promoter region (Bernoist and Chambon, *Nature* 29:304–310 (1981), the promoter contained in the 3' long terminal repeat of Rous sarcoma virus (Yamamoto et al., *Cell* 22:787–797 (1980), the herpes thymidine promoter (Wagner et al., *Proc. Natl. Acad. Sci. U.S.A.* 78:1441–1445 (1981), the regulatory sequences of the metallothionein gene (Brinster, et al., *Nature* 296:39–42 (1982)), etc.

The antisense nucleic acids of the invention comprise a sequence complementary to at least a portion of an RNA transcript of a DR5 gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded DR5 antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with a DR5 RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., *Nature* 372:333–335(1994). Thus, oligonucleotides complementary to either the 5'- or 3'-non-translated, non-coding regions of the DR5 shown in FIGS. 1A–B could be used in an antisense approach to inhibit translation of endogenous DR5 mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention Whether designed to hybridize to the 5'-, 3'-, or coding region of DR5 mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., *Proc. Natl. Acad. Sci. U.S.A.* 86:6553–6556 (1989); Lemaitre et al, *Proc. Natl. Acad. Sci.* 84:648–652 (1987); PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al, *BioTechniques* 6:958–976(1988)) or intercalating agents. (See, e.g., Zon, *Pharm. Res.* 5:539–549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino--3-N-2-carboxypropyl)uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an -anomeric oligonucleotide. An -anomeric oligonucleotide forms specific double-stranded hybrids with complementary RNA in which, contrary to the usual -units, the strands run parallel to each other (Gautier et al., *Nucl. Acids Res.* 15:6625–6641 (1987)). The oligonucleotide is a 2-O-methylribonucleotide (Inoue et al., *Nucl. Acids Res.* 15:6131–6148 (1987)), or a chimeric RNA-DNA analogue (Inoue et al, *FEBS Lett.* 215:327–330 (1987)).

Potential antagonists according to the invention also include catalytic RNA, or a ribozyme (See, e.g., PCT International Publication WO 90/11364, published Oct. 4, 1990; Sarver et al, *Science* 247:1222–1225 (1990). While ribozymes that cleave mRNA at site specific recognition sequences can be used to destroy DR5 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, *Nature* 334:585–591 (1988). There are numerous potential hammerhead ribozyme cleavage sites within the nucleotide sequence of DR5 (FIGS. 1A–B). Preferably, the ribozyme is engineered so that the cleavage recognition site is located near the 5' end of the DR5 mRNA; i.e., to increase efficiency and minimize the intracellular accumulation of non-functional mRNA transcripts. DNA constructs encoding the ribozyme may be introduced into the cell in the same manner as described above for the introduction of antisense encoding DNA. Since ribozymes, unlike antisense molecules are catalytic, a lower intracellular concentration is required for efficiency.

Further antagonist according to the present invention include soluble forms of DR5, i.e., DR5 fragments that include the ligand binding domain from the extracellular region of the full length receptor. Such soluble forms of the receptor, which may be naturally occurring or synthetic, antagonize DR5 mediated signaling by competing with the cell surface DR5 for binding to TNF-family ligands. Thus, soluble forms of the receptor that include the ligand binding domain are novel cytokines capable of inhibiting apoptosis induced by TNF-family ligands. These may be expressed as monomers, but, are preferably expressed as dimers or trimers, since these have been shown to be superior to monomeric forms of soluble receptor as antagonists, e.g., IgGFc-TNF receptor family fusions. Other such cytokines are known in the art and include Fas B (a soluble form of the mouse Fas receptor) that acts physiologically to limit apoptosis induced by Fas ligand (Hughes, D. P. and Crispe, I. N., *J. Exp. Med.* 182:1395–1401 (1995)).

As discussed above, the term "antibody" (Ab) or "monoclonal antibody" (mAb) as used herein is meant to include intact molecules as well as fragments thereof (such as, for example, Fab, and F(ab')$_2$ fragments) which are capable of binding an antigen. Fab, Fab', and F (ab')$_2$ fragments lack the Fc fragment of intact antibody, clear more rapidly from the circulation, and may have less non-specific tissue binding of an intact antibody (Wahl et al., J Nucl. Med. 24:316–325 (1983)).

Antibodies according to the present invention may be prepared by any of a variety of standard methods using DR5 immunogens of the present invention. As indicated, such DR5 immunogens include the full length DR5 polypeptide (which may or may not include the leader sequence) and DR5 polypeptide fragments such as the ligand binding domain, the transmembrane domain, the intracellular domain and the death domain.

Antibodies of the invention can be used in methods known in the art relating to the localization and activity of the polypeptide sequences of the invention, e.g., for imaging these polypeptides, measuring levels thereof in appropriate physiological samples, etc. The antibodies also have use in immunoassays and in therapeutics as agonists and antagonists of DR5.

Proteins and other compounds which bind the DR5 domains are also candidate agonist and antagonist according to the present invention. Such binding compounds can be "captured" using the yeast two-hybrid system (Fields and Song, *Nature* 340:245–246 (1989)). A modified version of the yeast two-hybrid system has been described by Roger Brent and his colleagues (Gyuris, J. et al., *Cell* 75:791–803 (1993); Zervos, A. S. et al., *Cell* 72:223–232 (1993)). Preferably, the yeast two-hybrid system is used according to the present invention to capture compounds which bind to either the DR5 ligand binding domain or to the DR5 intracellular domain. Such compounds are good candidate agonist and antagonist of the present invention.

By a "TNF-family ligand" is intended naturally occurring, recombinant, and synthetic ligands that are capable of binding to a member of the TNF receptor family and inducing the ligand/receptor signaling pathway. Members of the TNF ligand family include, but are not limited to, DR5 ligands, TRAIL, TNF-α, lymphotoxin-α (LT-α, also known as TNF-β), LT-β (found in complex heterotrimer LT-α2-β), FasL, CD40, CD27, CD30, 4-1BB, OX40 and nerve growth factor (NGF). An example of an assay that can be performed to determine the ability of DR5 and derivatives (including fragments) and analogs thereof to bind TRAIL is described below in Example 6.

Gene Therapy

In a specific embodiment, nucleic acids comprising sequences encoding antibodies or functional derivatives thereof, are administered to treat, inhibit and/or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention Exemplary methods are described below.

For general reviews of the methods of gene therapy, see Goldspiel et al, 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11(5): 155–215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody nucleic acids (Koller and Smithies, 1989, Proc. Natl. Acad. Sci. USA 86:8932–8935; Zijlstra et al., 1989, Nature 342:435–438). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262:4429–4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.), WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342:435–438).

In a specific embodiment, viral vectors that contains nucleic acid sequences encoding an antibody of the invention are used. For example, a retroviral vector can be used (see Miller et al., 1993, Meth. Enzymol. 217:581–599). These retroviral vectors have been to delete retroviral sequences that are not necessary for packaging of the viral genome and integration into host cell DNA. The nucleic acid sequences encoding the antibody to be used in gene therapy are cloned into one or more vectors, which facilitates delivery of the gene into a patient. More detail about retroviral vectors can be found in Boesen et al., 1994, Biotherapy 6:291–302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel. 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499–503 present a review of adenovirus-based gene therapy. Bout et al., 1994, Human Gene Therapy 5:3–10 demonstrated the use of adenovirus vectors to transfer genes to the respiratory epithelia of rhesus monkeys Other instances of the use of adenoviruses in gene therapy can be found in Rosenfeld et al., 1991, Science 252:431–434; Rosenfeld et al., 1992, Cell 68:143–155; Mastrangeli et al., 1993, J. Clin. Invest. 91.225–234; PCT Publication WO94/12649; and Wang et al., 1995, Gene Therapy 2:775–783. In a preferred embodiment, adenovirus vectors are used.

Adeno-associated virus (AAV) has also been proposed for use in gene therapy (Walsh et al., 1993, Proc. Soc. Exp. Biol. Med. 204:289–300; U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, *Meth. Enzymol.* 217:599–618; Cohen et al., 1993, *Meth. Enzymol.* 217:618–644; Cline, 1985, *Pharmac. Ther.* 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T-lymphocytes, B-lymphocytes, monocytes, macrophages, neutrophils, eosinophils, megakaryocytes, granulocytes; various stem or progenitor cells, in particular hematopoietic stem or progenitor cells. e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see, e.g., PCT Publication WO 94/08598, dated Apr. 28, 1994; Stemple and Anderson, 1992, *Cell* 71:973–985; Rheinwald, 1980, *Meth. Cell Bio.* 21A:229; and Pittelkow and Scott, 1986, *Mayo Clinic Proc.* 61:771).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription Modes of Administration The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

The agonist or antagonists described herein can be administered in vitro, ex vivo, or in vivo to cells which express the receptor of the present invention. By administration of an "effective amount" of an agonist or antagonist is intended an amount of the compound that is sufficient to enhance or inhibit a cellular response to a TNF-family ligand and include polypeptides. In particular, by administration of an "effective amount" of an agonist or antagonists is intended an amount effective to enhance or inhibit DR5 mediated apoptosis. Of course, where it is desired for apoptosis is to be enhanced, an agonist according to the present invention can be co-administered with a TNF-family ligand. One of ordinary skill will appreciate that effective amounts of an agonist or antagonist can be determined empirically and may be employed in pure form or in pharmaceutically acceptable salt, ester or prodrug form. The agonist or antagonist may be administered in compositions in combination with one or more pharmaceutically acceptable excipients (i.e., carriers).

It will be understood that, when administered to a human patient, the total daily usage of the compounds and compositions of the present invention will be decided by the attending physician within the scope of sound medical judgement. The specific therapeutically effective dose level for any particular patient will depend upon factors well known in the medical arts.

As a general proposition, the total pharmaceutically effective amount of DR5 polypeptide administered parenterally per dose will be in the range of about 1 $\mu$g/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the DR5 agonists or antagonists is typically administered at a dose rate of about 1 $\mu$g/kg/hour to about 50 $\mu$g/kg/hour, either by 1–4 injections per day or by continuous subcutaneous infusions, for example, using a mini-pump. An intravenous bag solution may also be employed.

Dosaging may also be arranged in a patient specific manner to provide a predetermined concentration of an agonist or antagonist in the blood, as determined by the RIA technique. Thus patient dosaging may be adjusted to achieve regular on-going trough blood levels, as measured by RIA, on the order of from 50 to 1000 ng/ml, preferably 150 to 500 ng/ml.

Pharmaceutical compositions are provided comprising an agonist or antagonist (including DR5 polynucleotides and polypeptides of the invention) and a pharmaceutically acceptable carrier or excipient, which may be administered orally, rectally, parenterally, intracistemally, intravaginally, intraperitoneally, topically (as by powders, ointments, drops or transdermal patch), bucally, or as an oral or nasal spray. Importantly, by co-administering an agonist and a TNF-family ligand, clinical side effects can be reduced by using lower doses of both the ligand and the agonist. It will be understood that the agonist can be "co-administered" either before, after, or simultaneously with the TNF-family ligand, depending on the exigencies of a particular therapeutic application. By "pharmaceutically acceptable carrier" is meant a non-toxic solid, semisolid or liquid filler, diluent, encapsulating material or formulation auxiliary of any type. In a specific embodiment, "pharmaceutically acceptable" means approved by a regulatory agency of the federal or a state government or listed in the U.S. Pharmacopeia or other generally recognized pharmacopeia for use in animals, and more particularly humans. The term "carrier" refers to a diluent, adjuvant, excipient, or vehicle with which the therapeutic is administered. Such pharmaceutical carriers include sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The term "parenteral" as used herein refers to modes of administration which include intravenous, intramuscular, intraperitoneal, intrasternal, subcutaneous and intraarticular injection and infusion.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429–4432), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc ) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, 1990, Science 249:1527–1533; Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, 1987, CRC Crit. Ref Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (1990, Science 249:1527–1533).

DR5 compositions of the invention are also suitably administered by sustained-release systems. Suitable examples of sustained-release compositions include suitable polymeric materials (such as, for example, semi-permeable polymer matrices in the form of shaped articles, e.g., films, or microcapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277(1981). and R. Langer, *Chem. Tech.* 12:98–105 (1982)), ethylene vinyl acetate (R. Langer et al., Id.) or poly-D-(−)-3-hydroxybutyric acid (EP 133,988).

Sustained-release compositions also include liposomally entrapped compositions of the invention (see generally, Langer, *Science* 249:1527–1533 (1990); Treat et al., in *Liposomes in the Therapy of Infectious Disease and Cancer*, Lopez-Berestein and Fidler (eds.), Liss, New York, pp. 317–327 and 353–365 (1989)). Liposomes containing DR5 polypeptide my be prepared by methods known per se: DE 3,218,121; Epstein et al., Proc. Natl. Acad. Sci (USA) 82:3688–3692 (1985); Hwang et al., Proc. Natl. Acad Sci. (USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal DR5 polypeptide therapy.

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980.286), or by direct injection, or by use of microparticle bombardment (e.g., a gene gun, Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864–1868), etc. Alternatively, a nucleic acid can be introduced intracellularly and incorporated within host cell DNA for expression, by homologous recombination.

In yet an additional embodiment, the compositions of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (Science 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al, 1991, Proc. Natl. Acad. Sci. USA 88:1864–1868), etc. Alternatively, a nucleic acid can be introduced intracellularly and incorporated within host cell DNA for expression, by homologous recombination.

Pharmaceutical compositions of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use.

In addition to soluble DR5 polypeptides, DR5 polypeptide containing the transmembrane region can also be used when appropriately solubilized by including detergents, such as CHAPS or NP-40, with buffer.

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

The compositions of the invention may be administered alone or in combination with other adjuvants. Adjuvants that may be administered with the compositions of the invention include, but are not limited to, alum, alum plus deoxycholate (ImmunoAg), MTP-PE (Biocine Corp.), QS21 (Genentech, Inc.), BCG, and MPL. In a specific embodiment, compositions of the invention are administered in combination with alum. In another specific embodiment, compositions of the invention are administered in combination with QS-21. Further adjuvants that may be administered with the compositions of the invention include, but are not limited to, Monophosphoryl lipid immunomodulator, AdjuVax 100a, QS-18, CRL1005, Aluminum salts, NF-59, and Virosomal adjuvant technology. Vaccines that may be administered with the compositions of the invention include, but are not limited to, vaccines directed toward protection against MMR (measles, mumps, rubella), polio, varicella, tetanus/diphtheria, Hepatitis A, Hepatitis B, *Haemophilus influenzae* type B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The compositions of the invention may be administered alone or in combination with other therapeutic agents. Therapeutic agents that may be administered in combination with the compositions of the invention, include but are not limited to, other members of the TNF family, chemotherapeutic agents, antibiotics, antivirals, steroidal and nonsteroidal anti-inflammatories, conventional immunotherapeutic agents, cytokines, chemokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the compositions of the invention are administered in combination with other members of the TNF family. TNF, TNF-related or TNF-like molecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-IBBL, DcR3, OX40L, TNF-gamma (International Publication No. WO 96/14328), TRAIL, AIM-II (International Publication No. WO 97/34911), APRIL (J. Exp. Med. 188(6): 1185–1190), endokine-alpha (International Publication No. WO 98/07880), TR6 (International Publication No. WO 98/30694), OPG and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TRANK, TR9 (International Publication No. WO 98/56892), TRIO (International Publication No. WO 98/54202), 312C2 (International Publication No. WO 98/06842), and TR12, and soluble forms of CD 154, CD70, and CD 153.

In another embodiment, the compositions of the invention are administered in combination with CD40 ligand (CD40L), a soluble form of CD40L (e.g., AVREND™), biologically active fragments, variants, or derivatives of CD40L, anti-CD40L antibodies (e.g., agonistic or antagonistic antibodies), and/or anti-CD40 antibodies (e.g., agonistic or antagonistic antibodies).

In yet another embodiment, the compositions of the invention are administered in combination with one, two, three, four, five, or more of the following compositions: tacrolimus (Fujisawa), thalidomide (e.g., Celgene), anti-Tac (Fv)-PE40 (e.g., Protein Design Labs), inolimomab (Biotest), MAK-195F (Knoll), ASM-981 (Novartis), interleukin-1 receptor (e.g., Immunex), interleukin-4 receptor (e.g., Immunex), ICM3 (ICOS), BMS-188667 (Bristol-Myers Squibb), anti-TNF Ab (e.g., Therapeutic antibodies), CG-1088 (Celgene), anti-B7 monoclonal antibody (e.g., Innogetics), MEDI-507 (BioTransplant), ABX-CBL (Abgenix).

According to the invention, a patient susceptible to both Fas ligand (Fas-L) mediated and TRAIL mediated cell death may be treated with both an agent that inhibits TRAIL/TRAIL-R interactions and an agent that inhibits Fas-L/Fas interactions. Suitable agents for blocking binding of Fas-L to Fas include, but are not limited to, soluble Fas polypeptides; oligomeric forms of soluble Fas polypeptides (e.g., dimers of sFas/Fc); anti-Fas antibodies that bind Fas without transducing the biological signal that results in apoptosis; anti-Fas-L antibodies that block binding of Fas-L to Fas; and muteins of Fas-L that bind Fas but do not transduce the biological signal that results in apoptosis. Preferably, the antibodies employed according to this method are monoclonal antibodies. Examples of suitable agents for blocking Fas-L/Fas interactions, including blocking anti-Fas monoclonal antibodies, are described in WO 95/10540, hereby incorporated by reference.

In certain embodiments, compositions of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the compositions of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the compositions of the invention, include, but are not limited to, VIRAMUNE™ (nevirapine), RESCRIPTOR™ (delavirdine), and SUSTIVA™ (efavirenz). Protease inhibitors that may be administered in combination with the compositions of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with compositions of the invention to treat AIDS and/or to prevent or treat HIV infection.

In other embodiments, compositions of the invention may be administered in combination with anti-opportunistic infection agents. Anti-opportunistic agents that may be administered in combination with the compositions of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, compositions of the invention are used in any combination with TRIMETHOPRIM-SULFAMETHOXAZOLE™, DAPSONE™, PENTAMIDINE™, and/or ATOVAQUONE™ to prophylactically treat and/or prevent an opportunistic *Pneumocystis carinii* pneumonia infection. In another specific embodiment, compositions of the invention are used in any combination with ISONIAZID™, RIFAMPIN™, PYRAZINAMIDE™, and/or ETHAMBUTOL™ to prophylactically treat and/or prevent an opportunistic *Mycobacterium avium* complex infection. In another specific embodiment, compositions of the invention are used in any combination with RIFABUTIN™, CLARITHROMYCIN™, and/or AZITHROMYCIN™ to prophylactically treat and/or prevent an opportunistic *Mycobacterium tuberculosis* infection. In another specific embodiment, compositions of the invention are used in any combination with GANCICLOVIR™, FOSCARNET™, and/or CIDOFOVIR™ to prophylactically treat and/or prevent an opportunistic cytomegalovirus infection. In another specific embodiment, compositions of the invention are used in any combination with FLUCONAZOLE™, ITRACONAZOLE™, and/or KETOCONAZOLE™ to prophylactically treat and/or prevent an opportunistic fungal infection. In another specific embodiment, compositions of the invention are used in any combination with ACYCLOVIR™ and/or FAMCICOLVIR™ to prophylactically treat and/or prevent an opportunistic herpes simplex virus type I and/or type II infection. In another specific embodiment, compositions of the invention are used in any combination with PYRIMETHAMINE™ and/or LEUCOVORIN™ to prophylactically treat and/or prevent an opportunistic *Toxoplasma gondii* infection. In another specific embodiment, compositions of the invention are used in any combination with LEUCOVORIN™ and/or NEUPOGEN™ to prophylactically treat and/or prevent an opportunistic bacterial infection.

In a further embodiment, the compositions of the invention are administered in combination with an antiviral agent. Antiviral agents that may be administered with the compositions of the invention include, but are not limited to, acyclovir, ribavirin, amantadine, and remantidine.

In a further embodiment, the compositions of the invention are administered in combination with an antibiotic agent. Antibiotic agents that may be administered with the compositions of the invention include, but are not limited to, amoxicillin, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the compositions of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T-cells.

In specific embodiments, compositions of the invention are administered in combination with immunosuppressants. Immunosuppressants preparations that may be administered with the compositions of the invention include, but are not limited to, ORTHOCLONE™ (OKT3), SANDIMMUNE™/ NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In an additional embodiment, compositions of the invention are administered alone or in combination with one or more intravenous immune globulin preparations. Intravenous immune globulin preparations that may be administered with the compositions of the invention include, but not limited to, GAMMAR™, IVEEGAM™, SANDOGLOBULIN™, GAMMAGARD S/D™, and GAMIMUNE™. In a specific embodiment, compositions of the invention are administered in combination with intravenous immune globulin preparations in transplantation therapy (e.g., bone marrow transplant).

In an additional embodiment, the compositions of the invention are administered alone or in combination with an anti-inflammatory agent. Anti-inflammatory agents that may be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap In one embodiment, the compositions of the invention are administered in combination with steroid therapy. Steroids that may be administered in combination with the compositions of the invention, include, but are not limited to, oral corticosteroids, prednisone, and methylprednisolone (e.g., IV methylprednisolone). In a specific embodiment, compositions of the invention are administered in combination with prednisone. In a further specific embodiment, the compositions of the invention are administered in combination with prednisone and an immunosuppressive agent. Immunosuppressive agents that may be administered with the compositions of the invention and prednisone are those described herein, and include, but are not limited to, azathioprine, cylophosphamide, and cyclophosphamide IV. In a another specific embodiment, compositions of the invention are administered in combination with methylprednisolone. In a further specific embodiment, the compositions of the invention are administered in combination with methylprednisolone and an immunosuppressive agent. Immunosuppressive agents that may be administered with the compositions of the invention and methylprednisolone are those described herein, and include, but are not limited to, azathioprine, cylophosphamide, and cyclophosphamide IV.

In another embodiment, the compositions of the invention are administered in combination with an antimalarial. Antimalarials that may be administered with the compositions of the invention include, but are not limited to, hydroxychloroquine, chloroquine, and/or quinacrine.

In yet another embodiment, the compositions of the invention are administered in combination with an NSAID.

In a nonexclusive embodiment, the compositions of the invention are administered in combination with one, two, three, four, five, ten, or more of the following drugs: NRD-101 (Hoechst Marion Roussel), diclofenac (Dimethaid), oxaprozin potassium (Monsanto), mecasermin (Chiron), T-614 (Toyama), pemetrexed disodium (Eli Lilly), atreleuton (Abbott), valdecoxib (Monsanto), eltenac (Byk Gulden), campath, AGM-1470 (Takeda), CDP-571 (Celltech Chiroscience), CM-101 (CarboMed), ML-3000 (Merckle), CB-2431 (KS Biomedix), CBF-BS2 (KS Biomedix), IL-1Ra gene therapy (Valentis), JTE-522 (Japan Tobacco), paclitaxel (Angiotech), DW-166HC (Dong Wha), darbufelone mesylate (Warner-Lambert), soluble TNF receptor 1 (synergen; Amgen), IPR-6001 (Institute for Pharmaceutical Research), trocade (Hoffman-La Roche), EF-5 (Scotia Pharmaceuticals), BIIL-284 (Boehringer Ingelheim), BIIF-1149 (Boehringer Ingelheim), Leuko Vax (Inflammatics), MK-663 (Merck), ST-1482 (Sigma-Tau), and butixocort propionate (WarnerLambert).

In yet another embodiment, the compositions of the invention are administered in combination with one, two, three, four, five or more of the following drugs: methotrexate, sulfasalazine, sodium aurothiomalate, auranofin, cyclosporine, penicillamine, azathioprine, an antimalarial drug (e.g., as described herein), cyclophosphamide, chlorambucil, gold, ENBREL™ (Etanercept), anti-TNF antibody, and prednisolone. In a more preferred embodiment, the compositions of the invention are administered in combination with an antimalarial, methotrexate, anti-TNF antibody, ENBREL™ and/or suflasalazine In one embodiment, the compositions of the invention are administered in combination with methotrexate. In another embodiment, the compositions of the invention are administered in combination with anti-TNF antibody. In another embodiment, the compositions of the invention are administered in combination with methotrexate and anti-TNF antibody. In another embodiment, the compositions of the invention are administered in combination with suflasalazine. In another specific embodiment, the compositions of the invention are administered in combination with methotrexate, anti-TNF antibody, and suflasalazine. In another embodiment, the compositions of the invention are administered in combination ENBREL™. In another embodiment, the compositions of the invention are administered in combination with ENBREL™ and methotrexate. In another embodiment, the compositions of the invention are administered in combination with ENBREL™, methotrexate and suflasalazine. In another embodiment, the compositions of the invention are administered in combination with ENBREL™, methotrexate and suflasalazine. In other embodiments, one or more antimalarials is combined with one of the above-recited combinations. In a specific embodiment, the compositions of the invention are administered in combination with an antimalarial (e.g., hydroxychloroquine), ENBREL™, methotrexate and suflasalazine. In another specific embodiment, the compositions of the invention are administered in combination with an antimalarial (e.g., hydroxychloroquine), sulfasalazine, anti-TNF antibody, and methotrexate.

In another embodiment, compostions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, compositions of the invention are administered in combination with CHOP (cyclophosphamide, doxorubicin, vincristine, and prednisone) or any combination of the components of CHOP. In another embodiment, compositions of the invention are administered in combination with Rituximab. In a further embodiment, compositions of the invention are administered with Rituxmab and CHOP, or Rituxmab and any combination of the components of CHOP.

In an additional embodiment, the compositions of the invention are administered in combination with cytokines. Cytokines that may be administered with the compositions of the invention include, but are not limited to, GM-CSF, G-CSF, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, anti-CD40, CD40L, IFN-alpha, IFN-beta, IFN-gamma, TNF-alpha, and TNF-beta.

In an additional embodiment, the compositions of the invention are administered in combination with hematopoietic growth factors. Hematopoietic growth factors that may be administered with the compositions of the invention included, but are not limited to, LEUKINE™ (SARGRAMOSTIM™) and NEUPOGEN™ (FILGRASTIM™).

In an additional embodiment, the compositions of the invention are administered in combination with angiogenic proteins. Angiogenic proteins that may be administered with the compositions of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PlGF-2), as disclosed in Hauser et al., *Growth Factors*, 4:259–268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B-186 (VEGF-B 186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the compositions of the invention are administered in combination with Fibroblast Growth Factors. Fibroblast Growth Factors that may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In one embodiment, the compositions of the invention are administered in combination with one or more chemokines. In specific embodiments, the compositions of the invention are administered in combination with an α(CxC) chemokine selected from the group consisting of gamma-interferon inducible protein-10 (γIP-10), interleukin-8 (IL-8), platelet factor-4 (PF4), neutrophil activating protein (NAP-2), GRO-α, GRO-β, GRO-γ, neutrophil-activating peptide (ENA-78), granulocyte chemoattractant protein-2 (GCP-2), and stromal cell-derived factor-1 (SDF-1, or pre-B-cell stimulatory factor (PBSF)); and/or a β (CC) selected from the group consisting of: RANTES (regulated on activation, normal T expressed and secreted), macrophage inflammatory protein-1 alpha (MIP-1α), macrophage inflammatory protein-1 beta (MIP-1β), monocyte chemotactic protein-1 (MCP-1), monocyte chemotactic protein-2 (MCP-2), monocyte chemotactic protein-3 (MCP-3), monocyte chemotactic protein -4 (MCP-4) macrophage inflammatory protein-1 gamma (MIP-1γ), macrophage inflammatory protein-3 alpha (MIP-3α), macrophage inflammatory protein-3 beta (MIP-3β), macrophage inflammatory protein-4 (MIP-4/DC-CK-1/PARC), eotaxin, Exodus, and I-309; and/or the γ(C) chemokine, lymphotactin.

In additional embodiments, the compositions of the invention are administered in combination with other therapeutic or prophylactic regimens, such as, for example, radiation therapy.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, M. et al., J. Cell. Biol. 101:976–985 (1985); Jalkanen, M. et al., J. Cell. Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{112}$In), and technetium ($^{99}$Tc); luminescent labels, such as luminol; and fluorescent labels, such as fluorescein and rhodamine, and biotin.

One aspect of the invention is the detection and diagnosis of a disease or disorder associated with aberrant expression of a polypeptide of the interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments" (Chapter 13 in Tumor Imaging: The Radiochemical Detection of Cancer, S. W. Burchiel and B. A. Rhodes, eds., Masson Publishing Inc. (1982)).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include anon-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or calorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Chromosome Assays

The nucleic acid molecules of the present invention are also valuable for chromosome identification. The sequence is specifically targeted to and can hybridize with a particular location on an individual human chromosome. The mapping of DNAs to chromosomes according to the present invention is an important first step in correlating those sequences with genes associated with disease.

In certain preferred embodiments in this regard, the cDNA and/or polynucleotides herein disclosed is used to clone genomic DNA of a DR5 gene. This can be accomplished using a variety of well known techniques and libraries, which generally are available commercially. The genomic DNA is then used for in situ chromosome mapping using well known techniques for this purpose.

In addition, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA to a metaphase chromosomal spread can be used to provide a precise chromosomal location in one step. This technique can be used with cDNA as short as 50 or 60 bp. For a review of this technique, see Verma et al., *Human Chromosomes: a Manual of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance in Man*, available on line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLE 1
Expression and Purification in *E. coli*

The DNA sequence encoding the mature DR5 protein in the deposited cDNA (ATCC No 97920) is amplified using PCR oligonucleotide primers specific to the amino terminal sequences of the DR5 protein and to vector sequences 3' to the gene. Additional nucleotides containing restriction sites to facilitate cloning are added to the 5' and 3' sequences respectively.

The following primers are used for expression of DR5 extracellular domain in *E. coli*: The 5' primer has the sequence:

5'-CGCCCATGGAGTCTGCTCTGATCAC-3' (SEQ ID NO:8) and contains the underlined NcoI site; and the 3' primer has the sequence:

5'-CGCAAGCTTTTAGCCTGATTCTTTGTGGAC-3' (SEQ ID NO:9) and contains the underlined HindIII site.

The restriction sites are convenient to restriction enzyme sites in the bacterial expression vector pQE60, which are used for bacterial expression in this example. (Qiagen, Inc. 9259 Eton Avenue, Chatsworth, Calif., 91311). pQE60 encodes ampicillin antibiotic resistance ("Amp$^r$") and contains a bacterial origin of replication ("ori"), an IPTG inducible promoter, and a ribosome binding site ("RBS").

The amplified DR5 DNA and the vector pQE60 both are digested with NcoI and HindIII and the digested DNAs are then ligated together. Insertion of the DR5 protein DNA into the restricted pQE60 vector places the DR5 protein coding region downstream of and operably linked to the vector's IPTG-inducible promoter and in-frame with an initiating AUG appropriately positioned for translation of DR5 protein.

The ligation mixture is transformed into competent *E. coli* cells using standard procedures. Such procedures are described in Sambrook et al., Molecular Cloning: a Laboratory Manual, 2nd Ed.; Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kan$^r$"), is used in carrying out the illustrative example described herein. This strain, which is only one of many that are suitable for expressing DR5 protein, is available commercially from Qiagen, supra.

Transformants are identified by their ability to grow on LB plates in the presence of ampicillin and kanamycin. Plasmid DNA is isolated from resistant colonies and the identity of the cloned DNA confirmed by restriction analysis, PCR, and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:100 to 1:250. The cells are grown to an optical density at 600 nm ("OD600") of between 0.4 and 0.6. Isopropyl-B-D-thiogalactopyranoside ("IPTG") is then added to a final concentration of 1 mM to induce transcription from lac repressor sensitive promoters, by inactivating the lacI repressor. Cells subsequently are incubated further for 3 to 4 hours.

Cells then are harvested by centrifugation and disrupted, by standard methods. Inclusion bodies are purified from the disrupted cells using routine collection techniques, and protein is solubilized from the inclusion bodies into 8M urea. The 8M urea solution containing the solubilized protein is passed over a PD-10 column in 2× phosphate-buffered saline ("PBS"), thereby removing the urea, exchanging the buffer and refolding the protein. The protein is purified by a further step of chromatography to remove endotoxin. Then, it is sterile filtered. The sterile filtered protein preparation is stored in 2× PBS at a concentration of 95 μ/ml.

EXAMPLE 2
Expression in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g. RSV, HTLVI, HIVI and the early promoter of the cytomegalovirus (CMV). However, cellular signals can also be used (e.g. the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC67109). Mammalian host cells that could be used include, human HeLa 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the gene of interest can be expressed in stable cell lines that contain the gene integrated into a chromosome. Co-transfection with a selectable marker such as dhfr, gpt, neomycin, hygromycin allows the identification and isolation of the transfected cells.

The transfected gene can also be amplified to express large amounts of the encoded protein. The dihydrofolate reductase (DHFR) marker is useful to develop cell lines that carry several hundred or even several thousand copies of the gene of interest. Another useful selection marker is the enzyme glutamine synthase (GS) (Murphy et al., *Biochem. J.* 227:277–279 (1991); Bebbington et al., *Bio/Technology* 10:169–175 (1992)). Using these markers, the mammalian cells are grown in selective medium and the cells with the highest resistance selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., *Molecular and Cellular Biology* 5:438–447 (March 1985)), plus a fragment of the CMV-enhancer (Boshart et al., *Cell* 41:521–530 (1985)). Multiple cloning sites, e.g. with the restriction enzyme cleavage sites BamHI, XbaI and Asp718, facilitate the cloning of the gene of interest. The vectors contain in addition the 3' intron, the polyadenylation and termination signal of the rat preproinsulin gene.

Cloning and Expression in CHO Cells

The vector pC4 is used for the expression of the DR5 polypeptide. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids, can be selected by growing the cells in a selective medium (alpha minus MEM, Life Technologies) supplemented with the chemotherapeutic agent methotrexate (MTX). The amplification of the DHFR genes in cells resistant to methotrexate (MTX) has been well documented (see, e.g., Alt, F. W, Kellems, R. M., Bertino, J. R., and Schimke, R. T., *J. Biol. Chem.* 253:1357–1370 (1978); Hamlin, J. L. and Ma, C., *Biochem. et Biophys. Acta* 1097:107–143 (1990); Page, M. J. and Sydenham, M. A. 1991, *Biotechnology* 9:64–68(1991))- Cells grown in increasing concentrations of MTX develop resistance to the drug by overproducing the target enzyme, DHFR, as a result of amplification of the DHFR gene. If a second gene is linked to the HFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains, for expressing the gene of interest, the strong promoter of the long terminal repeat (LTR) of the Rous Sarcoma Virus (Cullen et al., *Molecular and Cellular Biology* 5:438–447 (March 1985), plus a fragment isolated from the enhancer of the immediate early gene of human cytomegalovirus (CMV) (Boshart et al., *Cell* 41:521–530 (1985)). Downstream of the promoter are the following single restriction enzyme cleavage sites that allow the integration of the genes: BamHI, XhaI, and Asp718. Behind these cloning sites the plasmid contains the 3' intron and polyadenylation site of the rat preproinsulin gene. Other high efficiency promoters can also be used for expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the DR5 polypeptide in a regulated way in mammalian cells (Gossen, M., & Bujard, H., *Proc. Natl. Acad. Sci. USA* 89:5547–5551 (1992). For the polyadenylation of the mRNA, other signals, e.g., from the human growth hormone or globin genes, can be used as well.

Stable cell lines carrying a gene of interest integrated into the chromosomes can also be selected upon co-transfection with a selectable marker such as gpt, G418, or hygromycin. It is advantageous to use more than one selectable marker in the beginning, e.g., G418 plus methotrexate.

The plasmid pC4 is digested with the restriction enzyme BamHI and then dephosphorylated using calf intestinal phosphates by procedures known in the art. The vector is then isolated from a 1% agarose gel.

The DNA sequence encoding the complete polypeptide is amplified using PCR oligonucleotide primers corresponding to the 5' and 3' sequences of the desired portion of the gene. The 5' primer containing the underlined BamHI site, a Kozak sequence, and an AUG start codon, has the following sequence:

5'-CGCGGATCCGCCATCATGGAACAACGGGGAC AGAAC-3 (SEQ ID NO:10). The 3' primer, containing the underlined Asp718 site, has the following sequence:

5'-CGCGGTACCTTAGGACATGGCAGAGTC-3' (SEQ ID NO:11).

The amplified fragment is digested with the endonuclease BamHI and Asp718 and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five $\mu$g of the expression plasmid pC4 is cotransfected with 0.5 $\mu$g of the plasmid pSVneo using the lipofectin method (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10–14 days, single clones are trypsinized and then seeded in 6-well petri dishes or 10 ml flasks using different concentrations of methotrexate (50 nM, 100 nM, 200 M, 400 nM, 800 nM). Clones growing at the highest concentrations of methotrexate are then transferred to new 6-well plates containing even higher concentrations of methotrexate (1 $\mu$M, 2 $\mu$M, 5 $\mu$M, 10 mM, 20 mM). The same procedure is repeated until clones are obtained which grow at a concentration of 100–200 $\mu$M. Expression of the desired gene product is analyzed, for instance, by SDS-PAGE and Western blot or by reversed phase HPLC analysis.

Cloning and Expression in COS Cells

The expression plasmid, pDR5-HA, is made by cloning a cDNA encoding the soluble extracellular domain of the DR5 protein into the expression vector pcDNAI/Amp or pcDNAIII (which can be obtained from Invitrogen, Inc.). The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells, (4) a CMV promoter, a polylinker, an SV40 and a polyadenylation signal arranged so that a cDNA can be conveniently placed under expression control of the CMV promoter and operably linked to the SV40 intron and the polyadenylation signal by means of restriction sites in the polylinker. A DNA fragment encoding the extracelluar domain of the DR5 polypeptide and a HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al, *Cell* 37:767 (1984). The fusion of the HA tag to the target protein allows easy detection and recovery of the recombinant protein with an antibody that recognizes the HA epitope.

The plasmid construction strategy is as follows. The DR5 cDNA of the deposited plasmid is amplified using primers that contain convenient restriction sites, much as described above for construction of vectors for expression of DR5 in *E. coli.*

To facilitate detection, purification and characterization of the expressed DR5, one of the primers contains a hemagglutinin tag ("HA tag") as described above.

Suitable primers include the following, which are used in this example. The 5' primer, containing the underlined BamHI site has the following sequence:

5'-CGCGGATCCGCCATCATGGAACAACGGGGA CAGAAC-3 (SEQ ID NO:10). The 3' primer, containing the underlined Asp718 restriction sequence has the following sequence:

5'-CGCGGTACCTTAGCCTGATTCTTTTGGAC-3 (SEQ ID NO:12).

The PCR amplified DNA fragment and the vector, pcDNAI/Amp, are digested with BamHI and Asp718 and then ligated. The ligation mixture is transformed into E. coli strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the extracellular domain of the DR5 polypeptide For expression of recombinant DR5, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of DR5 by the vector.

Expression of the DR5-HA fusion protein is detected by radiolabeling and immunoprecipitation, using methods described in, for example Harlow et al., *Antibodies: A Laboratory Manual*, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al., cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

The primer sets used for expression in this example are compatible with pC4 used for CHO expression in this example, pcDNAI/Amp for COS expression in this example, and pA2 used for baculovirus expression in the following example. Thus, for example, the complete DR5 encoding fragment amplified for CHO expression could also be ligated into pcDNAI/Amp for COS expression or pA2 for baculovirus expression.

EXAMPLE 3

Protein Fusions of DR5

DR5 polypeptides of the invention are optionally fused to other proteins. These fusion proteins can be used for a variety of applications. For example, fusion of DR5 polypeptides to His-tag, HA-tag, protein A, IgG domains, and maltose binding protein facilitates purification. (See EP A 394,827; Traunecker, et al., Nature 331:84–86 (1988).) Similarly, fusion to IgG-1, IgG-3, and albumin increases the half-life time in vivo. Nuclear localization signals fused to DR5 polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made using techniques known in the art or by using or routinely modifying the following protocol, which outlines the fusion of a polypeptide to an IgG molecule.

Briefly, the human Fc portion of the IgG molecule can be PCR amplified, using primers that span the 5' and 3' ends of the sequence described in SEQ ID NO:13. These primers also preferably contain convenient restriction enzyme sites that will facilitate cloning into an expression vector, preferably a mammalian expression vector.

For example, if the pC4 (Accession No. 209646) expression vector is used, the human Fc portion can be ligated into the BamHI cloning site. Note that the 3' BamHI site should be destroyed. Next, the vector containing the human Fc portion is re-restricted with BamHI, linearizing the vector, and DR5 polynucleotide, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

EXAMPLE 4

Cloning and Expression of the Soluble Extracellular Domain of DR5 in a Baculovirus Expression System In this illustrative example, the plasmid shuttle vector pA2 is used to insert the cDNA encoding the complete DR5 protein, including its naturally associated signal sequence, into a baculovirus to express the DR5 protein, using standard methods, such as those described in Summers et al., *A Manual of Methods for Baculovirus Vectors and Insect Cell Culture Procedures*, Texas Agricultural Experimental Station Bulletin No. 1555 (1987). This expression vector contains the strong polyhedron promoter of the *Autograph californica* nuclear polyhedrosis virus (ACMNPV) followed by convenient restriction sites. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate viable virus that express the cloned polynucleotide.

Many other baculovirus vectors could be used in place of pA2, such as pAc373, pVL941 and pAcIM1 provided, as one skilled in the art would readily appreciate, that construction provides appropriately located signals for transcription, translation, secretion, and the like, such as an in-frame AUG and a signal peptide, as required. Such vectors are described, for example, in Luckow et al., *Virology* 170:31–39 (1989).

The cDNA sequence encoding the soluble extracellular domain of DR5 protein in the deposited plasmid (ATCC Deposit No. 97920) is amplified using PCR oligonucleotide primers corresponding to the 5' and 3' sequences of the gene:

The 5' primer for DR5 has the sequence:

5'-CGCGGATCCGCCATCATGGAACAACGGGGA CAGAAC-3' (SEQ ID NO:10) containing the underlined BamHI restriction enzyme site. Inserted into an expression vector, as described below, the 5' end of the amplified fragment encoding DR5 provides an efficient cleavage signal peptide. An efficient signal for initiation of translation in eukaryotic cells, as described by Kozak, M., *J. Mol. Biol.* 196:947–950 (1987) is appropriately located in the vector portion of the construct.

The 3' primer for DR5 has the sequence:
5'-CGCGGTACCTTAGCCTGATTCTTTGTGGAC-3' (SEQ ID NO.12) containing the underlined Asp718 restriction followed by nucleotides complementary to the DR5 nucleotide sequence in FIGS. 1A–B, followed by the stop codon.

The amplified fragment is isolated from a 1% agarose gel using a commercially available kit ("Geneclean," BIO 101 Inc., La Jolla, Calif.) The fragment then is digested with BamHI and Asp718 and again is purified on a 1% agarose gel. This fragment is designated "F1."

The plasmid is digested with the restriction enzymes BamHI and Asp718 and optionally can be dephosphorylated using calf intestinal phosphatase, using routine procedures known in the art. The DNA is then isolated from a 1% agarose gel using a commercially available kit ("Geneclean" BIO 101 Inc., La Jolla, Calif.). The vector DNA is designated herein "V1."

Fragment F1 and the dephosphorylated plasmid V1 are ligated together with T4 DNA ligase. *E. coli* HB101 cells, or other suitable *E. coli* hosts such as XL-1 Blue (Stratagene Cloning Systems, La Jolla, Calif.) cells, are transformed with the ligation mixture and spread on culture plates. Bacteria containing the plasmid with the human DR5 are identified using the PCR method, in which one of the primers used to amplify the gene is directed to the DR5 sequence and the second primer is from well within the vector so that only those bacterial colonies containing the DR5 gene fragment will show amplification of the DNA. The sequence of the cloned fragment is confirmed by DNA sequencing. This plasmid is designated herein pBac DR5.

5 µg of the plasmid pBac DR5 is co-transfected with 1.0 µg of a commercially available linearized baculovirus DNA ("BaculoGold™ baculovirus DNA", Pharmingen, San Diego, Calif.), using the lipofectin method described by Felgner et al., *Proc. Natl. Acad. Sci. USA* 84:7413–7417 (1987). 1 µg of BaculoGold™ virus DNA and 5 µg of the plasmid pBac DR5 are mixed in a sterile well of a microtiter plate containing 50 µl of serum free Grace's medium (Life Technologies Inc., Gaithersburg, Md.). Afterwards 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours, the transfection solution is removed from the plate and 1 ml of Grace's insect medium supplemented with 10% fetal calf serum is added. The plate is put back into an incubator and cultivation is continued at 27° C. for four days.

After four days, the supernatant is collected and a plaque assay is performed, as described by Summers and Smith, cited above. An agarose gel with "Blue Gal" (Life Technologies Inc., Gaithersburg, Md.) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, Md., pages 9–10). After appropriate incubation, blue stained plaques are picked with the tip of a micropipettor (e.g, Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later, the supernatants of these culture dishes are harvested and then they are stored at 4° C. The recombinant virus is called V-DR5.

To verify expression of the DR5 gene, Sf9 cells are grown in Grace's medium supplemented with 10% heat-inactivated FBS. The cells are infected with the recombinant baculovirus V-DR5 at a multiplicity of infection ("MOI") of about 2 (about 1 to about 3). Six hours later, the medium is removed and is replaced with SF900 II medium minus methionine and cysteine (available from Life Technologies Inc., Gaithersburg, Md.). If radiolabeled proteins are desired, 42 hours later, 5 µCi of $^{35}$S-methionine and 5 µCi $^{35}$S-cysteine (available from Amersham) are added. The cells are further incubated for 16 hours and then they are harvested by centrifugation. The proteins in the supernatant as well as the intracellular proteins are analyzed by SDS-PAGE followed by autoradiography (if radiolabeled). Microsequencing of the amino acid sequence of the amino terminus of purified protein may be used to determine the amino terminal sequence of the mature protein and thus the cleavage point and length of the secretory signal peptide.

EXAMPLE 5

DR5 Induced Apoptosis in Mammalian Cells

Overexpression of Fas/APO-1 and TNFR-1 in mammalian cells mimics receptor activation (M. Muzio et al., *Cell* 85: 817–827 (1996); M. P. Boldin et al., *Cell* 85:803–815 (1996)). Thus, this system was utilized to study the functional role of DR5 in inducing apoptosis. This example demonstrates that overexpression of DR5 induced apoptosis in both MCF7 human breast carcinoma cells and in human epitheloid carcinoma (HeLa) cells.

Experimental Design

Cell death assays were performed essentially as previously described (A. M. Chinnaiyan, et al, *Cell* 81:505–12 (1995); M. P. Boldin, et al., *J Biol Chem* 270: 7795–8 (1995); F. C. Kischkel, et al., EMBO 14:5579–5588 (1995); A. M. Chinnaiyan, et al., *J Biol Chem* 271: 4961–4965 (1996)). Briefly, MCF-7 human breast carcinoma clonal cell lines and HeLa cells were co-transfected with vector, DR5, DR5Δ (52-411), or TNFR-1, together with a beta-galactosidase reporter construct.

Figure 5C:
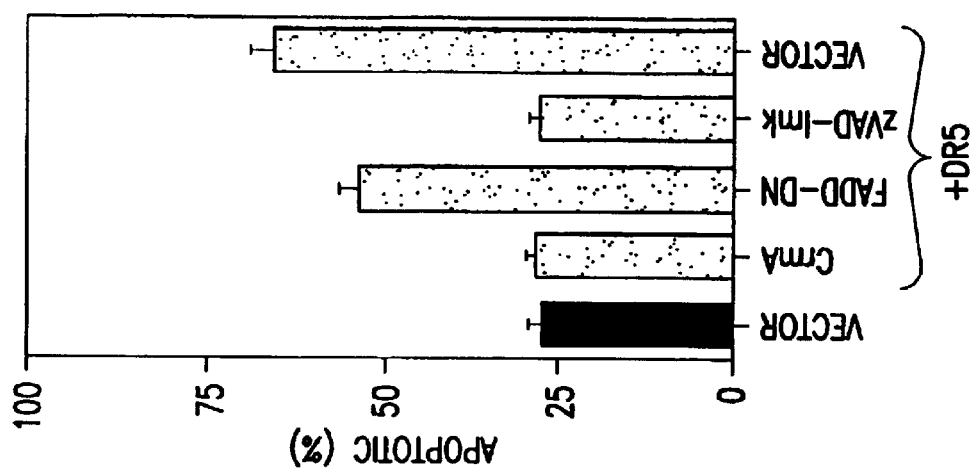
FIG. 5C is a bar graph showing that DR5-induced apoptosis was blocked by caspase inhibitors, CrmA and z-VAD-fmk, but dominant negative FADD was without effect.
Figure 5B:
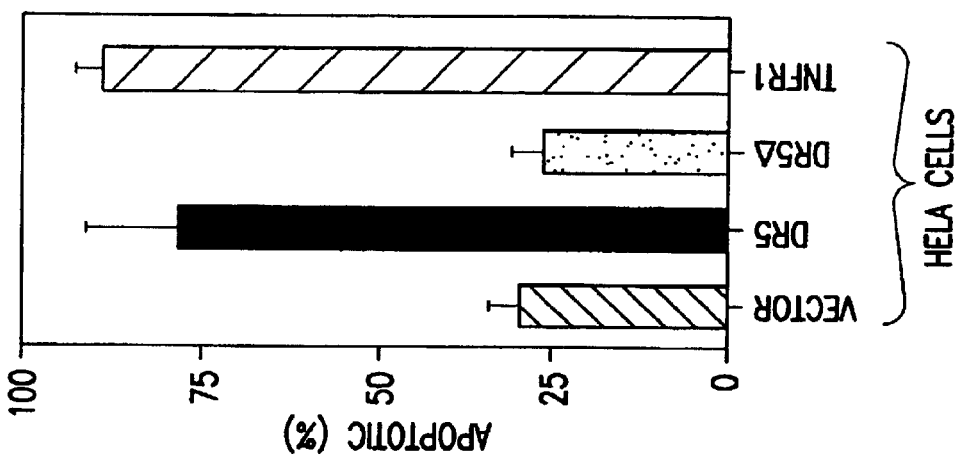
FIG. 5B is a bar graph showing that overexpression of DR5 induced apoptosis in human epitheloid carcinoma (HeLa) cells.
Figure 5A:
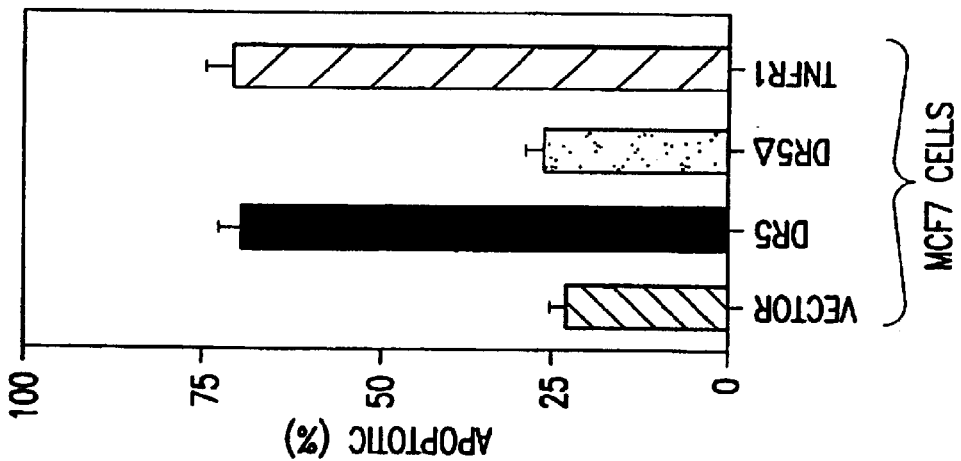
FIG. 5A is a bar graph showing that overexpression of DR5 induced apoptosis in MCF7 human breast carcinoma cells.

MCF7 and HeLa cells were transfected using the lipofectamine procedure (GIBCO-BRL), according to the manufacturer's instructions. 293 cells were transfected using CaPO$_4$ precipitation. Twenty-four hours following transfection, cells were fixed and stained with X-Gal as previously described (A. M. Chinnaiyan, et al., *Cell* 81:505–12 (1995); M. P. Boldin, et al., *J Biol Chem* 270:7795–8 (1995); F. C. Kischkel, et al., *EMBO* 14:5579–5588 (1995)), and examined microscopically. The data (mean±SD) presented in FIG. 5 represents the percentage of round, apoptotic cells as a function of total beta-galactosidase positive cells (n=3). Overexpression of DR5 induced apoptosis in both MCF7 (FIG. 5A) and HeLa cells (FIG. 5B).

MCF7 cells were also transfected with a DR5 expression construct in the presence of z-VAD-fmk (20 µl) (Enzyme Systems Products, Dublin, Calif.) or co-transfected with a three-fold excess of CrmA (M. Tewari et al., *J Biol Chem* 270:3255–60 (1995)), or FADD-DN expression construct, or vector alone. The data presented in FIG. 5C shows that apoptosis induced by DR5 was attenuated by caspase inhibitors, but not by dominant negative FADD.

As depicted in FIG. 5D, DR5 did not associate with FADD or TRADD in vivo. 293 cells were co-transfected with the indicated expression constructs using calcium phosphate precipitation. After transfection (at 40 hours), cell lysates were prepared and immunoprecipitated with Flag M2 antibody affinity gel (IBI, Kodak), and the presence of FADD or myc-tagged TRADD (myc-TRADD) was detected by immunoblotting with polyclonal antibody to FADD or horseradish peroxidase (HRP) conjugated antibody to myc (BMB) (Baker, S. J. et al., *Oncogene* 12:1 (1996); Chinnaiyan, A. M. et al., *Science* 274–990 (1996)).

Figure 5E:
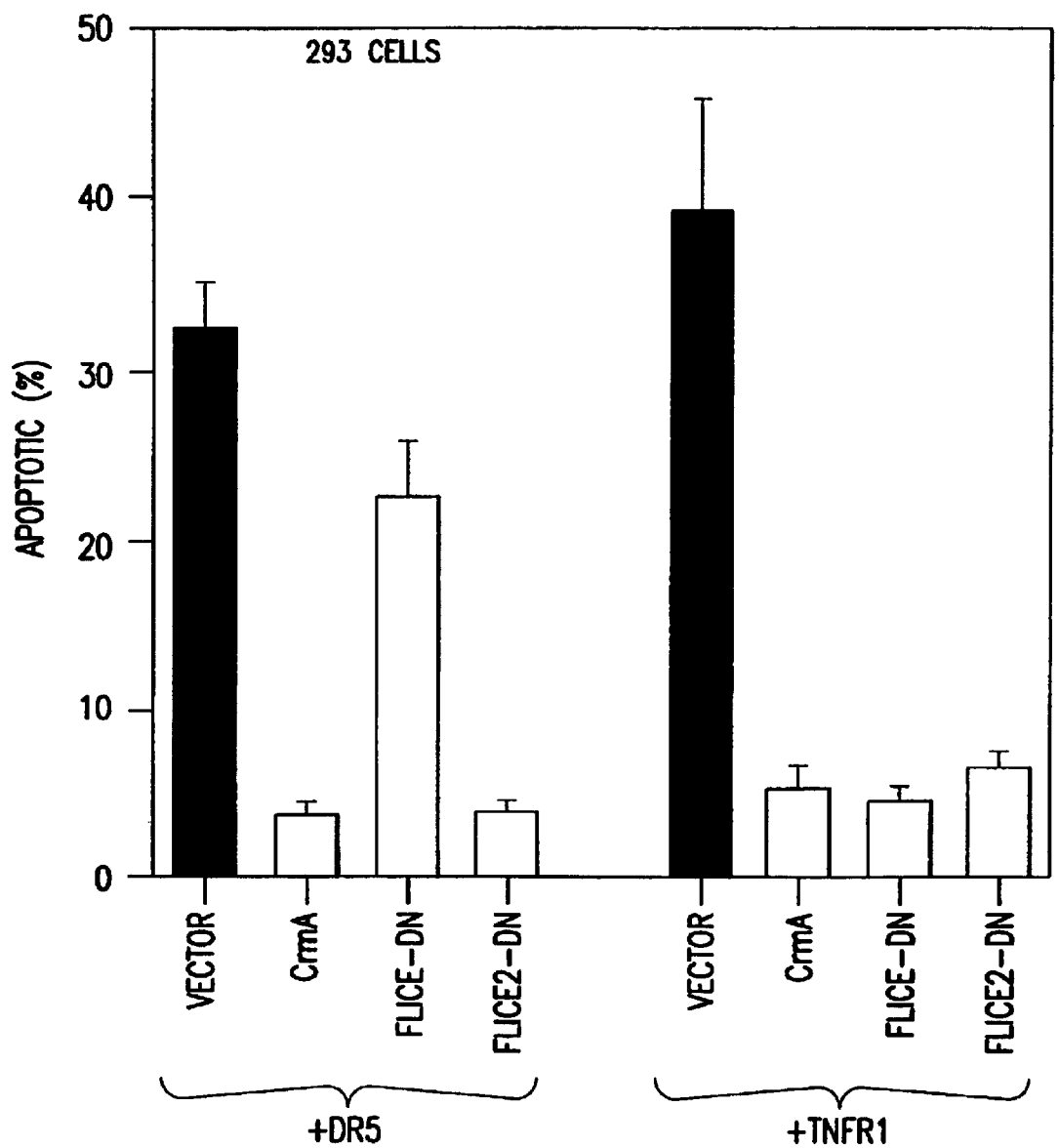
FIG. 5E is a bar graph showing that a dominant negative version of a newly identified FLICE-like molecule, FLICE2 (Vincenz, C. et al., *J. Biol. Chem.* 272:6578 (1997)), efficiently blocked DR5-induced apoptosis, while dominant negative FLICE had only partial effect under conditions it blocked. It also shows that TNFR-1 blocked apoptosis effectively.

As depicted in FIG. 5E, FLICE 2-DN blocks DR5-induced apoptosis. 293 cells were co-transfected with DR5 or TNFR-1 expression construct and a fourfold excess of CrmA, FLICE-DN, FLICE 2-DN, or vector alone in the presence of a beta-galactosidase reported construct as indicated. Cells were stained and examined 25–30 hours later.

Results

Overexpression of DR5, induced apoptosis in both MCF7 human breast carcinoma cells (FIG. 5A) and in human epitheloid carcinoma (HeLa) cells (FIG. 5B). Most of the transfected cells displayed morphological changes characteristic of cells undergoing apoptosis (Earnshaw, W. C., *Curr. Biol.* 7:337 (1995)), becoming rounded, condensed and detaching from the dish. Deletion of the death domain abolished killing ability. Like DR4, DR5-induced apoptosis was blocked by caspase inhibitors, CrmA and z-VAD-fmk, but dominant negative FADD was without effect (FIG. 5C). Consistent with this, DR5 did not interact with FADD and TRADD in vivo (FIG. 5D). A dominant negative version of a newly identified FLICE-like molecule, FLICE2 (Vincenz, C. et al., *J. Biol. Chem.* 272:6578 (1997)), efficiently blocked DR5-induced apoptosis, while dominant negative FLICE had only partial effect under conditions it blocked. TNFR-1 induced apoptosis effectively (FIG. 5E). Taken together, the evidence suggests that DR5 engages an apoptotic program that involves activation of FLICE2 and downstream caspases, but is independent of FADD.

EXAMPLE 6
The Extracellular Domain of DR5 Binds the Cytotoxic Ligand, TRAIL, and Blocks TRAIL-Induced Apoptosis As discussed above, TRAIL/Apo2L is a cytotoxic ligand that belongs to the tumor necrosis factor (TNF) ligand family and induces rapid cell death of many transformed cell lines, but not normal tissues, despite its death domain containing receptor, DR4, being expressed on both cell types This example shows that the present receptor, DR5, also binds TRAIL.

Given the similarity of the extracellular ligand binding cysteine-rich domains of DR5 and DR4, the present inventors theorized that DR5 would also bind TRAIL. To confirm this, the soluble extracellular ligand binding domains of DR5 were expressed as fusions to the Fc portion of human immunoglobulin (IgG). cDNA encoding the amino acids 1 to 129 in SEQ ID NO:2 was obtained by polymerase chain reaction and cloned into a modified pCMV1FLAG vector that allowed for in-frame fusion with the Fc portion of human IgG.

Figure 6A:
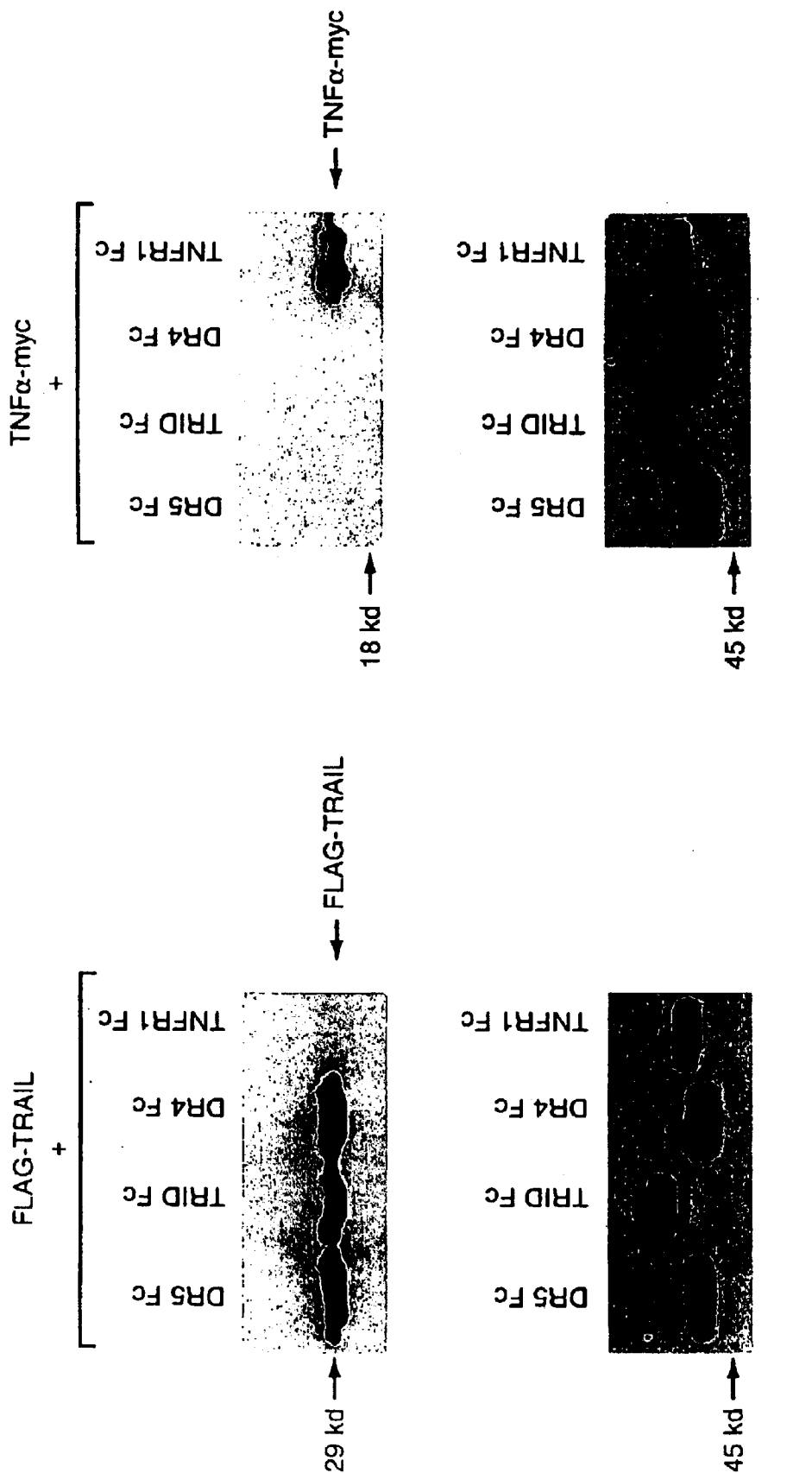
FIG. 6A is an immunoblot showing that DR5-Fc (as well as DR4 and TRID) specifically bound TRAIL, but not the related cytotoxic ligand TFNα. The bottom panel of FIG. 6A shows the input Fc-fusions present in the binding assays.

As shown in FIG. 6A, DR5-Fc specifically bound TRAIL, but not the related cytotoxic ligand TNFα. In this experiment, the Fc-extracellular domains of DR5, DR4, TRID, or TNFR-1 and the corresponding ligands were prepared and binding assays performed as described in Pan et al, *Science* 276:111 (1997). The respective Fc-fusions were precipitated with protein G-Sepharose and co-precipitated soluble ligands were detected by immunoblotting with anti-Flag (Babco) or anti-myc-HRP (BMB). The bottom panel of FIG. 6A shows the input Fc-fusions present in the binding assays.

Figure 6C:
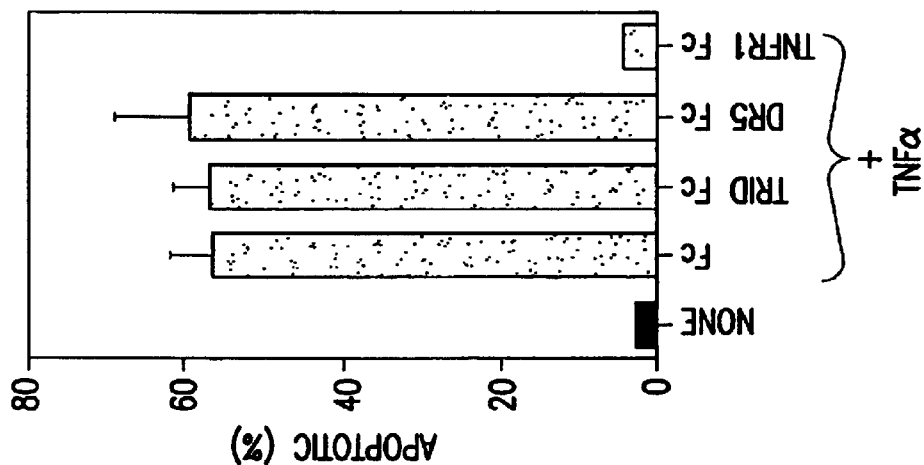
FIG. 6C is a bar graph showing that DR5-Fc had no effect on apoptosis TNFα-induced cell death under conditions where TNFR-1-Fc completely abolished TNFα killing.
Figure 6B:
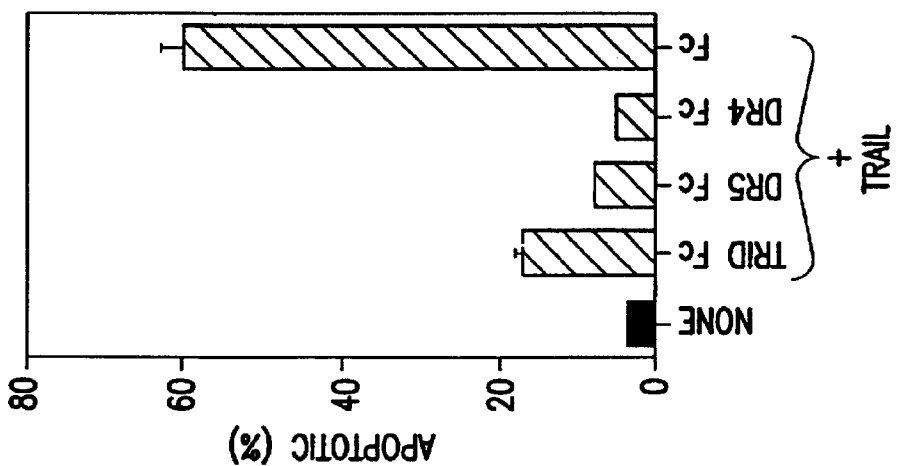
FIG. 6B is a bar graph showing that DR5-Fc blocked the ability of TRAIL to induce apoptosis. The data (mean±SD) shown in FIG. 6B are the percentage of apoptotic nuclei among total nuclei counted (n=4).

Additionally, DR5-Fc blocked the ability of TRAIL to induce apoptosis (FIG. 6B). MCF7 cells were treated with soluble TRAIL (200 ng/ml) in the presence of equal amounts of Fc-fusions or Fc alone. Six hours later, cells were fixed and examined as described in Pan et al., Id. The data (mean±SD) shown in FIG. 6B are the percentage of apoptotic nuclei among total nuclei counted (n=4).

Finally, DR5-Fc had no effect on apoptosis TNFα-induced cell death 5 under conditions where TNFR-1-Fc completely abolished TNFα killing (FIG. 6C). MCF7 cells were treated with TNFα (40 ng/ml; Genentech, Inc.) in the presence of equal amounts of Fc-fusions or Fc alone. Nuclei were stained and examined 11–15 hours later.

The new identification of DR5 as a receptor for TRAIL adds further complexity to the biology of TRAIL-initiated signal transduction.

EXAMPLE 7
Assays to Detect Stimulation or Inhibition of B Cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B-cell responsiveness including IL-2, IL-4, IL-5, IL-6, IL-7, IL-10, IL-13, IL-14 and IL-15. Interestingly, these signals are by themselves weak effectors but can, in combination with various co-stimulatory proteins, induce activation, proliferation, differentiation, homing, tolerance and death among B-cell populations. One of the best studied classes of B-cell co-stimulatory proteins is the TNF-superfamily. Within this family CD40, CD27, and CD30 along with their respective ligands CD 154, CD70, and CD 153 have been found to regulate a variety of immune responses. Assays that allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

Experimental Procedure

In Vitro assay- Purified DR5 protein, or truncated forms thereof, is assessed for its ability to induce activation, proliferation, differentiation or inhibition and/or death in B-cell populations and their precursors. The activity of DR5 protein on purified human tonsillar B-cells, measured qualitatively over the dose range from 0.1 to 10,000 ng/mL, is assessed in a standard B-lymphocyte co-stimulation assay in which purified tonsillar B-cells are cultured in the presence of either formalin-fixed *Staphylococcus aureus* Cowan I (SAC) or immobilized anti-human IgM antibody as the priming agent. Second signals such as IL-2 and IL-15 synergize with SAC and IgM cross-linking to elicit B-cell proliferation as measured by tritiated-thymidine incorporation. Novel synergizing agents can be readily identified using this assay. The assay involves isolating human tonsillar B-cells by magnetic bead (MACS) depletion of CD3-positive cells. The resulting cell population is greater than 95% B-cells as assessed by expression of CD45R (B220). Various dilutions of each sample are placed into individual wells of a 96-well plate to which are added $10^5$ B-cells suspended in culture medium (RPMI 1640 containing 10% FBS, $5\times10^{-5}$M β-ME, 100 U/ml penicillin, 10 μg/ml streptomycin, and $10^{-5}$ dilution of SAC) in a total volume of 150 μl. Proliferation or inhibition is quantitated by a 20 h pulse (1 μCi/well) with $^3$H-thymidine (6.7 Ci/mM) beginning 72 hours post factor addition. The positive and negative controls are IL-2 and medium respectively.

In Vivo assay-BALB/c mice are injected (i.p.) twice per day with buffer only, or with 2 mg/Kg of DR5 protein, or truncated forms thereof. Mice receive this treatment for 4 consecutive days, at which time they are sacrificed and various tissues and serum collected for analyses. Comparison of H&E sections from normal and DR5 protein-treated spleens identify the results of the activity of DR5 protein on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B-cell marker, anti-CD45R (B220), are used to determine whether any physiological changes to splenic cells, such as splenic disorganization, are due to increased B-cell representation within loosely defined B-cell zones that infiltrate established T-cell regions.

Flow cytometric analyses of the spleens from DR5 protein-treated mice is used to indicate whether DR5 protein specifically increases the proportion of ThB+, CD45R (B220) dull B-cells over that which is observed in control mice.

Likewise, a predicted consequence of increased mature B-cell representation in vivo is a relative increase in serum Ig titers. Accordingly, serum IgM and IgA levels are compared between buffer and DR5 protein-treated mice.

The studies described in this example test the activity in DR5 protein. However, one skilled in the art could easily modify the exemplified studies to test the activity of DR5 polynucleotides (e.g., gene therapy), agonists, and/or antagonists of DR5.

EXAMPLE 8
T-Cell Proliferation Assay

A CD3-induced proliferation assay is performed on PBMCs and is measured by the uptake of $^3$H-thymidine. The assay is performed as follows. Ninety-six well plates are coated with 100 μl/well of mAb to CD3 (HIT3a, Pharmingen) or isotype-matched control mAb (B33.1) overnight at 4° C. (1 μg/ml in 0.05M bicarbonate buffer, pH 9.5), then washed three times with PBS. PBMC are isolated by F/H gradient centrifugation from human peripheral blood and added to quadruplicate wells ($5\times10^4$/well) of mAb coated plates in RPMI containing 10% FCS and P/S in the presence of varying concentrations of DR5 protein (total volume 200 μl). Relevant protein buffer and medium alone are controls. After 48 hours at 37° C., plates are spun for 2 minutes at 1000 rpm and 100 μl of supernatant is removed and stored at −20° C. for measurement of IL-2 (or other cytokines) if an effect on proliferation is observed. Wells are supplemented with 100 μl of medium containing 0.5 μCi of $^3$H-thymidine and cultured at 37° C. for 18–24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T-cells is used as the negative controls for the effects of DR5 proteins.

The studies described in this example test the activity in DR5 protein. However, one skilled in the art could easily modify the exemplified studies to test the activity of DR5 polynucleotides (e.g., gene therapy), agonists, and/or antagonists of DR5

EXAMPLE 9
Effect of DR5 on the Expression of MHC Class II, Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7–10 days with GM-CSF (50 ng/ml) and IL-4 (20 ng/ml). These dendritic cells have the characteristic phenotype of immature cells (expression of CD1, CD80, CD86, CD40 and MIC class II antigens). Treatment with activating factors, such as TNF-α, causes a rapid change in surface phenotype (increased expression of MHC class I and II, costimulatory and adhesion molecules, downregulation of FCγRII, upregulation of CD83). These changes correlate with increased antigen-presenting capacity and with functional maturation of the dendritic cells.

FACS analysis of surface antigens is performed as follows. Cells are treated 1–3 days with increasing concentrations of DR5 or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Effect on the Production of Cytokines

Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA is used to measure the IL-12 release as follows. Dendritic cells ($10^6$/ml) are treated with increasing concentrations of DR5 for 24 hours. LPS (100 ng/ml) is added to the cell culture as positive control. Supernatants from the cell cultures are then collected and analyzed for IL-12 content using commercial ELISA kit (e.g., R & D Systems (Minneapolis, Minn.)). The standard protocols provided with the kits are used.

Effect on the Expression of MHC Class II, Costimulatory and Adhesion Molecules

Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T-cell activation. Increase expression of Fc receptors may correlate with improved monocyte cytotoxic activity, cytokine release and phagocytosis.

FACS analysis is used to examine the surface antigens as follows. Monocytes are treated 1–5 days with increasing concentrations of DR5 or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Monocyte Activation and/or Increased Survival

Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. DR5, agonists, or antagonists of DR5 can be screened using the three assays described below. For each of these assays, Peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

1. Monocyte Survival Assay. Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of $2 \times 10^6$/ml in PBS containing PI at a final concentration of 5 $\mu$g/ml, and then incubated at room temperature for 5 minutes before FACScan analysis PI uptake has been demonstrated to correlate with DNA fragmentation in this experimental paradigm.

2. Effect on Cytokine Release. An important function of monocytes/macrophages is their regulatory activity on other cellular populations of the immune system through the release of cytokines after stimulation. An ELISA to measure cytokine release is performed as follows. Human monocytes are incubated at a density of $5 \times 10^5$ cells/ml with increasing concentrations of DR5 and under the same conditions, but in the absence of DR5. For IL-12 production, the cells are primed overnight with IFN-$\gamma$ (100 U/ml) in presence of DR5. LPS (10 ng/ml) is then added. Conditioned media are collected after 24h and kept frozen until use. Measurement of TNF-$\alpha$, IL-10, MCP-1 and IL-8 is then performed using a commercially available ELISA kit (e.g., R & D Systems (Minneapolis, Minn.)) and applying the standard protocols provided with the kit.

3. Oxidative Burst. Purified monocytes are plated in 96-well plates at $2-1 \times 10^5$ cell/well. Increasing concentrations of DR5 are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0 56 mM phenol red and 19 U/ml of HRPO) is added, together with the stimulant (200 nM PMA). The plates are incubated at 37° C. for 2 hours and the reaction is stopped by adding 20 $\mu$l 1N NaOH per well. The absorbance is read at 610 nm. To calculate the amount of $H_2O_2$ produced by the macrophages, a standard curve of a $H_2O_2$ solution of known molarity is performed for each experiment.

The studies described in this example test the activity in DR5 protein. However, one skilled in the art could easily modify the exemplified studies to test the activity of DR5 polynucleotides (e.g., gene therapy), agonists, and/or antagonists of DR5.

EXAMPLE 10

The Effect of DR5 on the Growth of Vascular Endothelial Cells

On day 1, human umbilical vein endothelial cells (HUVEC) are seeded at $2-5 \times 10^4$ cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium is replaced with M199 containing 10% FBS, 8 units/ml heparin. DR5 protein of SEQ ID NO. 2, and positive controls, such as VEGF and basic FGF (bFGF) are added, at varying concentrations. On days 4 and 6, the medium is replaced. On day 8, cell number is determined with a Coulter Counter.

An increase in the number of HUVEC cells indicates that DR5 may proliferate vascular endothelial cells.

The studies described in this example test the activity in DR5 protein. However, one skilled in the art could easily modify the exemplified studies to test the activity of DR5 polynucleotides (e.g., gene therapy), agonists, and/or antagonists of DR5.

EXAMPLE 11

Production of an Antibody

A. Hybridoma Technology

The antibodies of the present invention can be prepared by a variety of methods. (See, Current Protocols, Chapter 2.) As one example of such methods, cells expressing DR5 are administered to an animal to induce the production of sera containing polyclonal antibodies. In a preferred method, a preparation of DR5 protein is prepared and purified to render it substantially free of natural contaminants. Such a preparation is then introduced into an animal in order to produce polyclonal antisera of greater specific activity.

Monoclonal antibodies specific for protein DR5 are prepared using hybridoma technology. (Kohler et al, *Nature* 256:495 (1975); Kohler et al., *Eur. J. Immunol.* 6:511 (1976); Kohler et al., *Eur. J. Immunol.* 6:292 (1976); Hammerling et al., in: Monoclonal Antibodies and T-Cell Hybridomas, Elsevier, N.Y., pp. 563–681 (1981)). In general, an animal (preferably a mouse) is immunized with DR5 polypeptide or, more preferably, with a secreted DR5 polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 $\mu$g/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (*Gastroenterology* 80:225–232 (1981). The hybridoma cells obtained through such a selection are then assayed to identify clones which secrete antibodies capable of binding the DR5 polypeptide.

Alternatively, additional antibodies capable of binding to DR5 polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the DR5 protein-specific antibody can be blocked by DR5, Such antibodies comprise anti-idiotypic antibodies to the DR5 protein-specific antibody and are used to immunize an animal to induce formation of further DR5 protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed infra. (See, for review, Morrison, *Science* 229:1202 (1985); Oi et al., *BioTechniques* 4:214 (1986); Cabilly et al., U.S. Pat. No. 4,816,567; Taniguchi et al, EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).)

B. Isolation of Antibody Fragments Directed Against DR5 from a Library of scFvs

Naturally occurring V-genes isolated from human PBLs are constructed into a large library of antibody fragments which contain reactivities against polypeptides of the present invention to which the donor may or may not have been exposed (see, e.g., U.S. Pat. No. 5,885,793 incorporated herein in its entirety by reference).

Rescue of the Library

A library of scFvs is constructed from the RNA of human PBLs as described in WO92/01047. To rescue phage displaying antibody fragments, approximately $10^9$ *E. coli* harboring the phagemid are used to inoculate 50 ml of 2×TY containing 1% glucose and 100 μg/ml of ampicillin (2×TY-AMP-GLU) and grown to an O.D. of 0.8 with shaking. Five ml of this culture is used to innoculate 50 ml of 2×TY-AMP-GLU, $2\times10^8$ TU of delta gene 3 helper phage (M13 gene III, see WO92/01047) are added and the culture incubated at 37° C. for 45 minutes without shaking and then at 37° C. for 45 minutes with shaking. The culture is centrifuged at 4000 r.p.m. for 10 minutes and the pellet resuspended in 2 liters of 2×TY containing 100 μg/ml ampicillin and 50 pg/ml kanamycin and grown overnight. Phage are prepared as described in WO92/01047.

M13 gene III is prepared as follows: M13 gene III helper phage does not encode gene III protein, hence the phage (mid) displaying antibody fragments have a greater avidity of binding to antigen. Infectious M13 gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are pelleted (IEC-Centra 8, 4000 revs/min for 10 min), resuspended in 300 ml 2×TY broth containing 100 μg ampicillin/ml and 25 μg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 pm filter (Minisart NML; Sartorius) to give a final concentration of approximately $10^{13}$ transducing units/ml (ampicillin-resistant clones).

Panning of the Library

Immunotubes (Nunc) are coated overnight in PBS with 4 ml of either 100 mg/ml or 10 mg/ml of a polypeptide of the present invention. Tubes are blocked with 2% Marvel-PBS for 2 hours at 37° C. and then washed 3 times in PBS. Approximately $10^{13}$ TU of phage are applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log *E. coli* TG1 by incubating eluted phage with bacteria for 30 minutes at 37° C. The *E. coli* are then plated on TYE plates containing 1% glucose and 100 pg/ml ampicillin. The resulting bacterial library is then rescued with M13 gene III helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders

Eluted phage from the 3rd and 4th rounds of selection are used to infect *E. coli* HEB 2151 and soluble scFv is produced (Marks, et al., 1991) from single colonies for assay. ELISAs are performed with microtiter plates coated with either 10 pg/ml of the polypeptide of the present invention in 50 mM bicarbonate pH 9.6. Clones positive in ELISA are further characterized by PCR fingerprinting (see e.g., WO92/01047) and then by sequencing.

EXAMPLE 12

Tissue Distribution of DR5 Gene Expression

Northern blot analysis was carried out to examine DR5 gene expression in human tissues, using methods described by, among others, Sambrook et al., cited above. A cDNA probe containing the entire nucleotide sequence of the DR5 protein (SEQ ID NO:1) was labeled with $^{32}$P using the rediprime™ DNA labeling system (Amersham Life Science), according to manufacturer's instructions. After labeling, the probe was purified using a CHROMA SPIN-100™ column (Clontech Laboratories, Inc.), according to manufacturer's protocol number PT1200-1. The purified labeled probe was then used to examine various human tissues for DR5 mRNA.

Multiple Tissue Northern (MTN) blots containing various human tissues (H) or human immune system tissues (IM) were obtained from Clontech (Palo Alto, Calif.) and examined with labeled probe using ExpressHyb™ hybridization solution (Clontech) according to manufacturer's protocol number PT 1190-1. Following hybridization and washing, the blots were mounted and exposed to film at −70° C. overnight. The films were developed according to standard procedures. Expression of DR5 was detected in heart, brain, placenta, lung, liver, skeletal muscle, kidney, pancreas, spleen, thymus, prostate, testis, uterus, small intestine, colon, peripheral blood leukocytes (PBLs), lymph node, bone marrow, and fetal liver.

Expression of DR5 was also assessed by Northern blot in the following cancer cell lines, HL60 (promyelocytic leukemia), HeLa cell S3, K562 (chronic myelogeneous leukemia), MOLT4 (lymphoblast leukemia), Raji (Burkitt's lymphoma), SW480 (colorectal adenocarcinoma), A549 (lung carcinoma), and G361 (melanoma), and was detected in all of the cell lines tested.

EXAMPLE 13

Method of Determining Alterations in the DR5 Gene

RNA is isolated from entire families or individual patients presenting with a phenotype of interest (such as a disease). cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95° C. for 30 seconds; 60–120 seconds at 52–58° C; and 60–120 seconds at 70° C., using buffer solutions described in Sidransky, D., et al., *Science* 252:706 (1991).

PCR products are then sequenced using primers labeled at their 5' end with T4 polynucleotide kinase, employing SequiTherm Polymerase. (Epicentre Technologies). The intron-exon borders of selected exons of DR5 are also determined and genomic PCR products analyzed to confirm the results. PCR products harboring suspected mutations in DR5 are then cloned and sequenced to validate the results of the direct sequencing.

PCR products of DR5 are cloned into T-tailed vectors as described in Holton, T. A. and Graham, M. W., *Nucleic Acids Research*, 19:1156 (1991) and sequenced with T7 polymerase (United States Biochemical). Affected individuals are identified by mutations in DR5 not present in unaffected individuals.

Genomic rearrangements are also observed as a method of determining alterations in the DR5 gene. Genomic clones isolated using techniques known in the art are nick-translated with digoxigenindeoxy-uridine 5'-triphosphate (Boehringer Mannheim), and FISH performed as described in Johnson, Cg. et al, *Methods Cell Biol.* 35:73–99 (1991). Hybridization with the labeled probe is carried out using a vast excess of human cot-1 DNA for specific hybridization to the DR5 genomic locus.

Chromosomes are counter-stained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., *Genet. Anal. Tech. Appl.*, 8:75 (1991).) Image collection, analysis and chromosomal fractional length measurements are performed using the ISee Graphical Program System. (Inovision Corporation, Durham, N.C.) Chromosome alterations of the genomic region of DR5 (hybridized by the probe) are identified as insertions, deletions, and translocations. These DR5 alterations are used as a diagnostic marker for an associated disease.

EXAMPLE 14
Method of Detecting Abnormal Levels of DR5 in a Biological Sample DR5 polypeptides can be detected in a biological sample, and if an increased or decreased level of DR5 is detected, this polypeptide is a marker for a particular phenotype. Methods of detection are numerous, and thus, it is understood that one skilled in the art can modify the following assay to fit their particular needs.

For example, antibody-sandwich ELISAs are used to detect DR5 in a sample, preferably a biological sample. Wells of a microtiter plate are coated with specific antibodies to DR5, at a final concentration of 0.2 to 10 µg/ml. The antibodies are either monoclonal or polyclonal and are produced using technique known in the art. The wells are blocked so that non-specific binding of DR5 to the well is reduced.

The coated wells are then incubated for >2 hours at RT with a sample containing DR5. Preferably, serial dilutions of the sample should be used to validate results. The plates are then washed three times with deionized or distilled water to remove unbounded DR5.

Next, 50 µl of specific antibody-alkaline phosphatase conjugate, at a concentration of 25–400 ng, is added and incubated for 2 hours at room temperature. The plates are again washed three times with deionized or distilled water to remove unbounded conjugate.

75 µl of 4-methylumbelliferyl phosphate (MUP) or p-nitrophenyl phosphate (NPP) substrate solution is then added to each well and incubated 1 hour at room temperature to allow cleavage of the substrate and fluorescence. The fluorescence is measured by a microtiter plate reader. A standard curve is prepared using the experimental results from serial dilutions of a control sample with the sample concentration plotted on the X-axis (log scale) and fluorescence or absorbance on the Y-axis (linear scale). The DR5 polypeptide concentration in a sample is then interpolated using the standard curve based on the measured fluorescence of that sample.

EXAMPLE 15
Method of Treating Decreased Levels of DR5

The present invention relates to a method for treating an individual in need of a decreased level of DR5 biological activity in the body comprising, administering to such an individual a composition comprising a therapeutically effective amount of DR5 antagonist. Preferred antagonists for use in the present invention are DR5-specific antibodies.

Moreover, it will be appreciated that conditions caused by a decrease in the standard or normal expression level of DR5 in an individual can be treated by administering DR5, preferably in a soluble and/or secreted form. Thus, the invention also provides a method of treatment of an individual in need of an increased level of DR5 polypeptide comprising administering to such an individual a pharmaceutical composition comprising an amount of DR5 to increase the biological activity level of DR5 in such an individual.

For example, a patient with decreased levels of DR5 polypeptide receives a daily dose 0.1–100 g/kg of the polypeptide for six consecutive days. Preferably, the polypeptide is in a soluble and/or secreted form.

EXAMPLE 16
Method of Treating Increased Levels of DR5

The present invention also relates to a method for treating an individual in need of an increased level of DR5 biological activity in the body comprising administering to such an individual a composition comprising a therapeutically effective amount of DR5 or an agonist thereof.

Antisense technology is used to inhibit production of DR5. This technology is one example of a method of decreasing levels of DR5 polypeptide, preferably a soluble and/or secreted form, due to a variety of etiologies, such as cancer.

For example, a patient diagnosed with abnormally increased levels of DR5 is administered intravenously antisense polynucleotides at 0.5, 1.0, 1.5, 2.0 and 3.0 mg/kg day for 21 days. This treatment is repeated after a 7-day rest period if the is determined to be well tolerated.

EXAMPLE 17
Method of Treatment Using Gene Therapy—Ex Vivo

One method of gene therapy transplants fibroblasts, which are capable of expressing soluble and/or mature DR5 polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding DR5 can be amplified using PCR primers which correspond to the 5' and 3' end encoding sequences respectively. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform *E. coli* HB 101, which are then plated onto agar containing kanamycin for the purpose of confirming that the vector contains properly inserted DR5.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the DR5 gene is then added to the media and the packaging cells transduced with the vector. The packaging cells now produce infectious viral particles containing the DR5 gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a Millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether DR5 protein is produced.

The engineered fibroblasts are then transplanted onto the host, either alone or after having been grown to confluence on cytodex 3 microcarrier beads.

EXAMPLE 18

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) DR5 sequences into an animal to increase or decrease the expression of the DR5 polypeptide. The DR5 polynucleotide may be operatively linked to a promoter or any other genetic elements necessary for the expression of the DR5 polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata H. et al., *Cardiovasc. Res.* 35:470–479 (1997); Chao J. et al., *Pharmacol. Res.* 35:517–522 (1997); Wolff J. A. *Neuronmuscul. Disord.* 7:314–318 (1997); Schwartz B. et al, *Gene Ther.* 3:405–411 (1996); Tsurumi Y. et al., *Circulation* 94:3281–3290 (1996) (incorporated herein by reference).

The DR5 polynucleotide constructs may be delivered by any method that delivers injectable materials to the cells of an animal, such as, injection into the interstitial space of tissues (heart, muscle, skin, lung, liver, intestine and the like). The DR5 polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the DR5 polynucleotides may also be delivered in liposome formulations (such as those taught in Felgner P. L. et al. *Ann. NY Acad. Sci.* 772:126–139 (1995), and Abdallah B. et al. *Biol. Cell* 85:1–7 (1995)) which can be prepared by methods well known to those skilled in the art.

The DR5 polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The DR5 polynucleotide construct can be delivered to the interstitial space of tissues within an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked DR5 polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked DR5 polynucleotide constructs can be delivered to arteries during angioplasty by the catheter used in the procedure.

The dose response effects of injected DR5 polynucleotide in muscle in vivo are determined as follows. Suitable DR5 template DNA for production of mRNA coding for DR5 polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The DR5 template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 μm cross-section of the individual quadriceps muscles is histochemically stained for DR5 protein expression. A time course for DR5 protein expression may be done in a similar fashion except that quadriceps from different mice are harvested at different times. Persistence of DR5 DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using DR5 naked DNA.

EXAMPLE 19
A DR5-Fc Fusion Protein Inhibits B Cell Proliferation in Vitro in a Co-Stimulatory Assay A DR5-Fc polypeptide was prepared that consists of a soluble form of DR5 (corresponding to amino acids −51 to 133 of SEQ ID NO:2) linked to the Fc portion of a human IgG1 immunoglobulin molecule. The ability of this protein to alter the proliferative response of human B-cells was assessed in a standard co-stimulatory assay. Briefly, human tonsillar B-cells were purified by magnetic bead (MACS) depletion of CD3-positive cells. The resulting cell population was routinely greater than 95% B-cells as assessed by expression of CD19 and CD20 staining. Various dilutions of rHuNeutrokine-alpha (International Application Publication No. WO 98/18921) or the control protein rHuIL2 were placed into individual wells of a 96-well plate to which was added $10^5$ B-cells suspended in culture medium (RPMI 1640 containing 10% FBS, $5 \times 10^{-5}$M 2ME, 100 U/ml penicillin, 10 μg/ml streptomycin, and $10^{-5}$ dilution of formalin-fixed *Staphylococcus aureus* Cowan I (SAC) also known as Pansorbin (Pan)) in a total volume of 150 μl. DR5-Fc was then added at various concentrations. Plates were then placed in the incubator (37° C. 5% $CO_2$, 95% humidity) for three days. Proliferation was quantitated by a 20 hour pulse (1 μCi/well) of $^3$H-thymidine (6.7 Ci/mM) beginning 72 hours post factor addition. The positive and negative controls are IL-2 and medium, respectively.

The results of this experiment confirmed that DR5-Fc inhibited B-cell proliferation in the co-stimulatory assay using *Staphylococcus aureus* Cowan 1 (SAC) as priming agent and Neutrokine-alpha as a second signal (data not shown). It is important to note that other Tumor Necrosis Factor Receptors (TNFR) fusion proteins (e.g., DR4-Fc (International Application Publication No. WO 98/32856), TR6-Fc (International Application Publication No. WO 98/31799), and TR9-Fc (International Application Publication No. WO 98/56892)) did not inhibit proliferation.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference.

Further, the Sequence Listing submitted herewith, in paper form, is hereby incorporated by reference in its entirety.

What is claimed is:

1. An isolated TRAIL receptor DNA, wherein said DNA comprises the nucleotide sequence presented in SEQ ID NO:1.

2. An expression vector comprising a DNA according to claim 1.

3. The expression vector of claim 2, wherein said DNA is operably associated with a heterologous regulatory sequence.

4. A host cell transformed with an expression vector of claim 2.

5. The host cell of claim 4, wherein said DNA is operably associated with a heterologous regulatory sequence.

6. The DNA of claim 1, wherein said DNA encodes a polypeptide which binds TRAIL.

7. The DNA of claim 1, wherein said DNA encodes a polypeptide which induces apoptosis.

8. The DNA of claim 1, further comprising a heterologous DNA.

9. The DNA of claim 8, wherein said heterologous DNA encodes a heterologous polypeptide.

10. The DNA of claim 9, wherein said heterologous polypeptide comprises an immunoglobulin Fc region.

11. The DNA of claim 10, wherein said immunoglobulin Fc region is a human immunoglobulin Fc region.

12. A method of producing a vector that comprises inserting the DNA of claim 1 into a vector.

13. A method of producing the polypeptide encoded by the DNA of claim 1, comprising culturing a host cell comprising said DNA under conditions such that said polypeptide is expressed, and recovering said polypeptide.

14. An isolated TRAIL receptor DNA, wherein said DNA encodes a polypeptide comprising amino acids −51 to 360 of SEQ ID NO:2.

15. An expression vector comprising a DNA according to claim 14.

16. The expression vector of claim 15, wherein said DNA is operably associated with a heterologous regulatory sequence.

17. A host cell transformed with an expression vector of claim 15.

18. The host cell of claim 17, wherein said DNA is operably associated with a heterologous regulatory sequence.

19. The DNA of claim 14, wherein said polypeptide induces apoptosis.

20. The DNA of claim 14, further comprising a heterologous DNA.

21. The DNA of claim 20, wherein said heterologous DNA encodes a heterologous polypeptide.

22. The DNA of claim 21, wherein said heterologous polypeptide comprises an immunoglobulin Fc region.

23. The DNA of claim 22, wherein said immunoglobulin Fc region is a human immunoglobulin Fc region.

24. A method of producing a vector that comprises inserting the DNA of claim 14 into a vector.

25. A method of producing the polypeptide encoded by the DNA of claim 14, comprising culturing a host cell comprising said DNA under conditions such that said polypeptide is expressed, and recovering said polypeptide.

26. An isolated TRAIL receptor DNA that encodes a polypeptide capable of binding TRAIL, wherein said polypeptide comprises amino acids 1 to 360 of SEQ ID NO:2.

27. An expression vector comprising a DNA according to claim 26.

28. The expression vector of claim 27, wherein said DNA is operably associated with a heterologous regulatory sequence.

29. A host cell transformed with an expression vector of claim 27.

30. The host cell of claim 29, wherein said DNA is operably associated with a heterologous regulatory sequence.

31. The DNA of claim 26, wherein said polypeptide induces apoptosis.

32. The DNA of claim 26, further comprising a heterologous DNA.

33. The DNA of claim 32, wherein said heterologous DNA encodes a heterologous polypeptide.

34. The DNA of claim 33, wherein said heterologous polypeptide comprises an immunoglobulin Fc region.

35. The DNA of claim 34, wherein said immunoglobulin Fc region is a human immunoglobulin Fc region.

36. A method of producing a vector that comprises inserting the DNA of claim 26 into a vector.

37. A method of producing the polypeptide encoded by the DNA of claim 26, comprising culturing a host cell comprising said DNA under conditions such that said polypeptide is expressed, and recovering said polypeptide.

38. An isolated TRAIL receptor DNA, wherein said DNA encodes a polypeptide comprising amino acids −51 to 133 of SEQ ID NO:2.

39. An expression vector comprising a DNA according to claim 38.

40. The expression vector of claim 39, wherein said DNA is operably associated with a heterologous regulatory sequence.

41. A host cell transformed with an expression vector of claim 39.

42. The host cell of claim 41, wherein said DNA is operably associated with a heterologous regulatory sequence.

43. The DNA of claim 38, further comprising a heterologous DNA.

44. The DNA of claim 43, wherein said heterologous DNA encodes a heterologous polypeptide.

45. The DNA of claim 44, wherein said heterologous polypeptide comprises an immunoglobulin Fc region.

46. The DNA of claim 45, wherein said immunoglobulin Fc region is a human immunoglobulin Fc region.

47. A method of producing a vector that comprises inserting the DNA of claim 38 into a vector.

48. A method of producing the TRAIL receptor polypeptide encoded by the DNA of claim 38, comprising culturing a host cell comprising said DNA under conditions such that said polypeptide is expressed, and recovering said polypeptide.

* * * * *

SEQUENCE LISTING

```
<160> NUMBER OF SEQ ID NOS: 14

<210> SEQ ID NO 1
<211> LENGTH: 1600
<212> TYPE: DNA
<213> ORGANISM: Homo sapiens
<220> FEATURE:
<221> NAME/KEY: CDS
<222> LOCATION: (130)..(1362)
<221> NAME/KEY: mat_peptide
<222> LOCATION: (283)..(1362)
<221> NAME/KEY: sig_peptide
<222> LOCATION: (130)..(282)

<400> SEQUENCE: 1
cacgcgtccg cgggcgcggc cggagaaccc cgcaatcttt gcgcccacaa aatacaccga      60
cgatgcccga tctactttaa gggctgaaac ccacgggcct gagagactat aagagcgttc     120 cctaccgcc atg gaa caa cgg gga cag aac gcc ccg gcc gct tcg ggg gcc    171
            Met Glu Gln Arg Gly Gln Asn Ala Pro Ala Ala Ser Gly Ala
            -50             -45                 -40
```

| | | |
|---|---|---|
| cgg aaa agg cac ggc cca gga ccc agg gag gcg cgg gga gcc agg cct<br>Arg Lys Arg His Gly Pro Gly Pro Arg Glu Ala Arg Gly Ala Arg Pro<br>       -35                       -30                       -25 | | 219 |
| ggg ccc cgg gtc ccc aag acc ctt gtg ctc gtt gtc gcc gcg gtc ctg<br>Gly Pro Arg Val Pro Lys Thr Leu Val Leu Val Val Ala Ala Val Leu<br>    -20                      -15                      -10 | | 267 |
| ctg ttg gtc tca gct gag tct gct ctg atc acc caa caa gac cta gct<br>Leu Leu Val Ser Ala Glu Ser Ala Leu Ile Thr Gln Gln Asp Leu Ala<br> -5                    -1  1            5                    10 | | 315 |
| ccc cag cag aga gcg gcc cca caa caa aag agg tcc agc ccc tca gag<br>Pro Gln Gln Arg Ala Ala Pro Gln Gln Lys Arg Ser Ser Pro Ser Glu<br>          15                     20                    25 | | 363 |
| gga ttg tgt cca cct gga cac cat atc tca gaa gac ggt aga gat tgc<br>Gly Leu Cys Pro Pro Gly His His Ile Ser Glu Asp Gly Arg Asp Cys<br>      30                     35                    40 | | 411 |
| atc tcc tgc aaa tat gga cag gac tat agc act cac tgg aat gac ctc<br>Ile Ser Cys Lys Tyr Gly Gln Asp Tyr Ser Thr His Trp Asn Asp Leu<br>   45                     50                   55 | | 459 |
| ctt ttc tgc ttg cgc tgc acc agg tgt gat tca ggt gaa gtg gag cta<br>Leu Phe Cys Leu Arg Cys Thr Arg Cys Asp Ser Gly Glu Val Glu Leu<br> 60                    65                    70                75 | | 507 |
| agt ccc tgc acc acg acc aga aac aca gtg tgt cag tgc gaa gaa ggc<br>Ser Pro Cys Thr Thr Thr Arg Asn Thr Val Cys Gln Cys Glu Glu Gly<br>               80                     85                    90 | | 555 |
| acc ttc cgg gaa gaa gat tct cct gag atg tgc cgg aag tgc cgc aca<br>Thr Phe Arg Glu Glu Asp Ser Pro Glu Met Cys Arg Lys Cys Arg Thr<br>          95                    100                  105 | | 603 |
| ggg tgt ccc aga ggg atg gtc aag gtc ggt gat tgt aca ccc tgg agt<br>Gly Cys Pro Arg Gly Met Val Lys Val Gly Asp Cys Thr Pro Trp Ser<br>      110                    115                   120 | | 651 |
| gac atc gaa tgt gtc cac aaa gaa tca ggc atc atc ata gga gtc aca<br>Asp Ile Glu Cys Val His Lys Glu Ser Gly Ile Ile Ile Gly Val Thr<br>          125                  130                  135 | | 699 |
| gtt gca gcc gta gtc ttg att gtg gct gtg ttt gtt tgc aag tct tta<br>Val Ala Ala Val Val Leu Ile Val Ala Val Phe Val Cys Lys Ser Leu<br>140                    145                   150                155 | | 747 |
| ctg tgg aag aaa gtc ctt cct tac ctg aaa ggc atc tgc tca ggt ggt<br>Leu Trp Lys Lys Val Leu Pro Tyr Leu Lys Gly Ile Cys Ser Gly Gly<br>         160                   165                   170 | | 795 |
| ggt ggg gac cct gag cgt gtg gac aga agc tca caa cga cct ggg gct<br>Gly Gly Asp Pro Glu Arg Val Asp Arg Ser Ser Gln Arg Pro Gly Ala<br>               175                   180                185 | | 843 |
| gag gac aat gtc ctc aat gag atc gtg agt atc ttg cag ccc acc cag<br>Glu Asp Asn Val Leu Asn Glu Ile Val Ser Ile Leu Gln Pro Thr Gln<br>         190                   195                   200 | | 891 |
| gtc cct gag cag gaa atg gaa gtc cag gag cca gca gag cca aca ggt<br>Val Pro Glu Gln Glu Met Glu Val Gln Glu Pro Ala Glu Pro Thr Gly<br>     205                    210                   215 | | 939 |
| gtc aac atg ttg tcc ccc ggg gag tca gag cat ctg ctg gaa ccg gca<br>Val Asn Met Leu Ser Pro Gly Glu Ser Glu His Leu Leu Glu Pro Ala<br>220                    225                   230                235 | | 987 |
| gaa gct gaa agg tct cag agg agg agg ctg ctg gtt cca gca aat gaa<br>Glu Ala Glu Arg Ser Gln Arg Arg Arg Leu Leu Val Pro Ala Asn Glu<br>         240                   245                   250 | | 1035 |
| ggt gat ccc act gag act ctg aga cag tgc ttc gat gac ttt gca gac<br>Gly Asp Pro Thr Glu Thr Leu Arg Gln Cys Phe Asp Asp Phe Ala Asp<br>              255                   260                265 | | 1083 |
| ttg gtg ccc ttt gac tcc tgg gag ccg ctc atg agg aag ttg ggc ctc<br>Leu Val Pro Phe Asp Ser Trp Glu Pro Leu Met Arg Lys Leu Gly Leu | | 1131 |

-continued

```
                 270                 275                 280
atg gac aat gag ata aag gtg gct aaa gct gag gca gcg ggc cac agg         1179
Met Asp Asn Glu Ile Lys Val Ala Lys Ala Glu Ala Ala Gly His Arg
    285                 290                 295 gac acc ttg tac acg atg ctg ata aag tgg gtc aac aaa acc ggg cga         1227
Asp Thr Leu Tyr Thr Met Leu Ile Lys Trp Val Asn Lys Thr Gly Arg
300                 305                 310                 315 gat gcc tct gtc cac acc ctg ctg gat gcc ttg gag acg ctg gga gag         1275
Asp Ala Ser Val His Thr Leu Leu Asp Ala Leu Glu Thr Leu Gly Glu
                320                 325                 330 aga ctt gcc aag cag aag att gag gac cac ttg ttg agc tct gga aag         1323
Arg Leu Ala Lys Gln Lys Ile Glu Asp His Leu Leu Ser Ser Gly Lys
            335                 340                 345 ttc atg tat cta gaa ggt aat gca gac tct gcc atg tcc taagtgtgat          1372
Phe Met Tyr Leu Glu Gly Asn Ala Asp Ser Ala Met Ser
        350                 355                 360 tctcttcagg aagtgagacc ttccctggtt tacctttttt ctggaaaaag cccaactgga       1432
ctccagtcag taggaaagtg ccacaattgt cacatgaccg gtactggaag aaactctccc       1492
atccaacatc acccagtgga tggaacatcc tgtaactttt cactgcactt ggcattattt       1552
ttataagctg aatgtgataa taaggacact atggaaaaaa aaaaaaaa                    1600
```

<210> SEQ ID NO 2
<211> LENGTH: 411
<212> TYPE: PRT
<213> ORGANISM: Homo sapiens

<400> SEQUENCE: 2

```
Met Glu Gln Arg Gly Gln Asn Ala Pro Ala Ala Ser Gly Ala Arg Lys
    -50                 -45                 -40

Arg His Gly Pro Gly Pro Arg Glu Ala Arg Gly Ala Arg Pro Gly Pro
-35                 -30                 -25                 -20

Arg Val Pro Lys Thr Leu Val Leu Val Val Ala Ala Val Leu Leu Leu
                -15                 -10                  -5

Val Ser Ala Glu Ser Ala Leu Ile Thr Gln Gln Asp Leu Ala Pro Gln
         -1   1                   5                  10

Gln Arg Ala Ala Pro Gln Gln Lys Arg Ser Ser Pro Ser Glu Gly Leu
         15                  20                  25

Cys Pro Pro Gly His His Ile Ser Glu Asp Gly Arg Asp Cys Ile Ser
 30                  35                  40                  45

Cys Lys Tyr Gly Gln Asp Tyr Ser Thr His Trp Asn Asp Leu Leu Phe
                 50                  55                  60

Cys Leu Arg Cys Thr Arg Cys Asp Ser Gly Glu Val Glu Leu Ser Pro
             65                  70                  75

Cys Thr Thr Thr Arg Asn Thr Val Cys Gln Cys Glu Glu Gly Thr Phe
 80                  85                  90

Arg Glu Glu Asp Ser Pro Glu Met Cys Arg Lys Cys Arg Thr Gly Cys
     95                 100                 105

Pro Arg Gly Met Val Lys Val Gly Asp Cys Thr Pro Trp Ser Asp Ile
110                 115                 120                 125

Glu Cys Val His Lys Glu Ser Gly Ile Ile Gly Val Thr Val Ala
                130                 135                 140

Ala Val Val Leu Ile Val Ala Val Phe Val Cys Lys Ser Leu Leu Trp
                145                 150                 155

Lys Lys Val Leu Pro Tyr Leu Lys Gly Ile Cys Ser Gly Gly Gly Gly
            160                 165                 170
```

-continued

```
Asp Pro Glu Arg Val Asp Arg Ser Ser Gln Arg Pro Gly Ala Glu Asp
    175                 180                 185

Asn Val Leu Asn Glu Ile Val Ser Ile Leu Gln Pro Thr Gln Val Pro
190                 195                 200                 205

Glu Gln Glu Met Glu Val Gln Glu Pro Ala Glu Pro Thr Gly Val Asn
                210                 215                 220

Met Leu Ser Pro Gly Glu Ser Glu His Leu Leu Glu Pro Ala Glu Ala
                225                 230                 235

Glu Arg Ser Gln Arg Arg Arg Leu Leu Val Pro Ala Asn Glu Gly Asp
            240                 245                 250

Pro Thr Glu Thr Leu Arg Gln Cys Phe Asp Asp Phe Ala Asp Leu Val
    255                 260                 265

Pro Phe Asp Ser Trp Glu Pro Leu Met Arg Lys Leu Gly Leu Met Asp
270                 275                 280                 285

Asn Glu Ile Lys Val Ala Lys Ala Glu Ala Ala Gly His Arg Asp Thr
                290                 295                 300

Leu Tyr Thr Met Leu Ile Lys Trp Val Asn Lys Thr Gly Arg Asp Ala
                305                 310                 315

Ser Val His Thr Leu Leu Asp Ala Leu Glu Thr Leu Gly Glu Arg Leu
            320                 325                 330

Ala Lys Gln Lys Ile Glu Asp His Leu Leu Ser Ser Gly Lys Phe Met
    335                 340                 345

Tyr Leu Glu Gly Asn Ala Asp Ser Ala Met Ser
350                 355                 360

<210> SEQ ID NO 3
<211> LENGTH: 455
<212> TYPE: PRT
<213> ORGANISM: Homo sapiens

<400> SEQUENCE: 3

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
        50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
```

```
                    180                 185                 190
Lys Leu Cys Leu Pro Gln Ile Glu Asn Val Lys Gly Thr Glu Asp Ser
            195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Lys Pro Leu Ala Pro Asn Pro Ser
            260                 265                 270

Phe Ser Pro Thr Pro Gly Phe Thr Pro Thr Leu Gly Phe Ser Pro Val
            275                 280                 285

Pro Ser Ser Thr Phe Thr Ser Ser Thr Tyr Thr Pro Gly Asp Cys
290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
            355                 360                 365

Leu Arg Trp Lys Glu Phe Val Arg Arg Leu Gly Leu Ser Asp His Glu
            370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
            435                 440                 445

Pro Ala Pro Ser Leu Leu Arg
    450                 455

<210> SEQ ID NO 4
<211> LENGTH: 335
<212> TYPE: PRT
<213> ORGANISM: Homo sapiens

<400> SEQUENCE: 4

Met Leu Gly Ile Trp Thr Leu Leu Pro Leu Val Leu Thr Ser Val Ala
  1               5                  10                  15

Arg Leu Ser Ser Lys Ser Val Asn Ala Gln Val Thr Asp Ile Asn Ser
                 20                  25                  30

Lys Gly Leu Glu Leu Arg Lys Thr Val Thr Thr Val Glu Thr Gln Asn
             35                  40                  45

Leu Glu Gly Leu His His Asp Gly Gln Phe Cys His Lys Pro Cys Pro
         50                  55                  60

Pro Gly Glu Arg Lys Ala Arg Asp Cys Thr Val Asn Gly Asp Glu Pro
 65                  70                  75                  80

Asp Cys Val Pro Cys Gln Glu Gly Lys Glu Tyr Thr Asp Lys Ala His
                 85                  90                  95
```

-continued

```
Phe Ser Ser Lys Cys Arg Arg Cys Arg Leu Cys Asp Glu Gly His Gly
            100                 105                 110
Leu Glu Val Glu Ile Asn Cys Thr Arg Thr Gln Asn Thr Lys Cys Arg
        115                 120                 125
Cys Lys Pro Asn Phe Phe Cys Asn Ser Thr Val Cys Glu His Cys Asp
    130                 135                 140
Pro Cys Thr Lys Cys Glu His Gly Ile Ile Lys Glu Cys Thr Leu Thr
145                 150                 155                 160
Ser Asn Thr Lys Cys Lys Glu Glu Gly Ser Arg Ser Asn Leu Gly Trp
                165                 170                 175
Leu Cys Leu Leu Leu Leu Pro Ile Pro Leu Ile Val Trp Val Lys Arg
            180                 185                 190
Lys Glu Val Gln Lys Thr Cys Arg Lys His Arg Lys Glu Asn Gln Gly
        195                 200                 205
Ser His Glu Ser Pro Thr Leu Asn Pro Glu Thr Val Ala Ile Asn Leu
    210                 215                 220
Ser Asp Val Asp Leu Ser Lys Tyr Ile Thr Thr Ile Ala Gly Val Met
225                 230                 235                 240
Thr Leu Ser Gln Val Lys Gly Phe Val Arg Lys Asn Gly Val Asn Glu
                245                 250                 255
Ala Lys Ile Asp Glu Ile Lys Asn Asp Asn Val Gln Asp Thr Ala Glu
            260                 265                 270
Gln Lys Val Gln Leu Leu Arg Asn Trp His Gln Leu His Gly Lys Lys
        275                 280                 285
Glu Ala Tyr Asp Thr Leu Ile Lys Asp Leu Lys Lys Ala Asn Leu Cys
    290                 295                 300
Thr Leu Ala Glu Lys Ile Gln Thr Ile Ile Leu Lys Asp Ile Thr Ser
305                 310                 315                 320
Asp Ser Glu Asn Ser Asn Phe Arg Asn Glu Ile Gln Ser Leu Val
                325                 330                 335

<210> SEQ ID NO 5
<211> LENGTH: 417
<212> TYPE: PRT
<213> ORGANISM: Homo sapiens

<400> SEQUENCE: 5

Met Glu Gln Arg Pro Arg Gly Cys Ala Ala Val Ala Ala Ala Leu Leu
 1                5                  10                  15
Leu Val Leu Leu Gly Ala Arg Ala Gln Gly Gly Thr Arg Ser Pro Arg
                20                  25                  30
Cys Asp Cys Ala Gly Asp Phe His Lys Lys Ile Gly Leu Phe Cys Cys
            35                  40                  45
Arg Gly Cys Pro Ala Gly His Tyr Leu Lys Ala Pro Cys Thr Glu Pro
    50                  55                  60
Cys Gly Asn Ser Thr Cys Leu Val Cys Pro Gln Asp Thr Phe Leu Ala
65                  70                  75                  80
Trp Glu Asn His His Asn Ser Glu Cys Ala Arg Cys Gln Ala Cys Asp
                85                  90                  95
Glu Gln Ala Ser Gln Val Ala Leu Glu Asn Cys Ser Ala Val Ala Asp
            100                 105                 110
Thr Arg Cys Gly Cys Lys Pro Gly Trp Phe Val Glu Cys Gln Val Ser
        115                 120                 125
Gln Cys Val Ser Ser Ser Pro Phe Tyr Cys Gln Pro Cys Leu Asp Cys
    130                 135                 140
```

-continued

```
Gly Ala Leu His Arg His Thr Arg Leu Leu Cys Ser Arg Arg Asp Thr
145                 150                 155                 160

Asp Cys Gly Thr Cys Leu Pro Gly Phe Tyr Glu His Gly Asp Gly Cys
            165                 170                 175

Val Ser Cys Pro Thr Ser Thr Leu Gly Ser Cys Pro Glu Arg Cys Ala
        180                 185                 190

Ala Val Cys Gly Trp Arg Gln Met Phe Trp Val Gln Val Leu Leu Ala
    195                 200                 205

Gly Leu Val Val Pro Leu Leu Leu Gly Ala Thr Leu Thr Tyr Thr Tyr
210                 215                 220

Arg His Cys Trp Pro His Lys Pro Leu Val Thr Ala Asp Glu Ala Gly
225                 230                 235                 240

Met Glu Ala Leu Thr Pro Pro Ala Thr His Leu Ser Pro Leu Asp
                245                 250                 255

Ser Ala His Thr Leu Leu Ala Pro Pro Asp Ser Ser Glu Lys Ile Cys
            260                 265                 270

Thr Val Gln Leu Val Gly Asn Ser Trp Thr Pro Gly Tyr Pro Glu Thr
        275                 280                 285

Gln Glu Ala Leu Cys Pro Gln Val Thr Trp Ser Trp Asp Gln Leu Pro
290                 295                 300

Ser Arg Ala Leu Gly Pro Ala Ala Pro Thr Leu Ser Pro Glu Ser
305                 310                 315                 320

Pro Ala Gly Ser Pro Ala Met Met Leu Gln Pro Gly Pro Gln Leu Tyr
                325                 330                 335

Asp Val Met Asp Ala Val Pro Ala Arg Arg Trp Lys Glu Phe Val Arg
            340                 345                 350

Thr Leu Gly Leu Arg Glu Ala Glu Ile Glu Ala Val Glu Val Glu Ile
        355                 360                 365

Gly Arg Phe Arg Asp Gln Gln Tyr Glu Met Leu Lys Arg Trp Arg Gln
    370                 375                 380

Gln Gln Pro Ala Gly Leu Gly Ala Val Tyr Ala Ala Leu Glu Arg Met
385                 390                 395                 400

Gly Leu Asp Gly Cys Val Glu Asp Leu Arg Ser Arg Leu Gln Arg Gly
                405                 410                 415

Pro
```

```
<210> SEQ ID NO 6
<211> LENGTH: 507
<212> TYPE: DNA
<213> ORGANISM: Homo Sapiens
<220> FEATURE:
<221> NAME/KEY: Unsure
<222> LOCATION: 152
<223> OTHER INFORMATION: n= any nucleotide
<221> NAME/KEY: Unsure
<222> LOCATION: 199
<223> OTHER INFORMATION: n= any nucleotide
<221> NAME/KEY: Unsure
<222> LOCATION: 272
<223> OTHER INFORMATION: n= any nucleotide
<221> NAME/KEY: Unsure
<222> LOCATION: 285
<223> OTHER INFORMATION: n= any nucleotide
<221> NAME/KEY: Unsure
<222> LOCATION: 310
<223> OTHER INFORMATION: n= any nucleotide
<221> NAME/KEY: Unsure
<222> LOCATION: 322
<223> OTHER INFORMATION: n= any nucleotide
<221> NAME/KEY: Unsure
```

```
<222> LOCATION: 329
<223> OTHER INFORMATION: n= any nucleotide
<221> NAME/KEY: Unsure
<222> LOCATION: 331
<223> OTHER INFORMATION: n= any nucleotide
<221> NAME/KEY: Unsure
<222> LOCATION: 344
<223> OTHER INFORMATION: n= any nucleotide
<221> NAME/KEY: Unsure
<222> LOCATION: 353
<223> OTHER INFORMATION: n= any nucleotide
<221> NAME/KEY: Unsure
<222> LOCATION: 363
<223> OTHER INFORMATION: n= any nucleotide
<221> NAME/KEY: Unsure
<222> LOCATION: 368
<223> OTHER INFORMATION: n= any nucleotide
<221> NAME/KEY: Unsure
<222> LOCATION: 370
<223> OTHER INFORMATION: n= any nucleotide
<221> NAME/KEY: Unsure
<222> LOCATION: 374
<223> OTHER INFORMATION: n= any nucleotide
<221> NAME/KEY: Unsure
<222> LOCATION: 376
<223> OTHER INFORMATION: n= any nucleotide
<221> NAME/KEY: Unsure
<222> LOCATION: 388
<223> OTHER INFORMATION: n= any nucleotide
<221> NAME/KEY: Unsure
<222> LOCATION: 393
<223> OTHER INFORMATION: n= any nucleotide
<221> NAME/KEY: Unsure
<222> LOCATION: 403
<223> OTHER INFORMATION: n= any nucleotide
<221> NAME/KEY: Unsure
<222> LOCATION: 407
<223> OTHER INFORMATION: n= any nucleotide
<221> NAME/KEY: Unsure
<222> LOCATION: 409
<223> OTHER INFORMATION: n= any nucleotide
<221> NAME/KEY: Unsure
<222> LOCATION: 410
<223> OTHER INFORMATION: n= any nucleotide
<221> NAME/KEY: Unsure
<222> LOCATION: 414
<223> OTHER INFORMATION: n= any nucleotide
<221> NAME/KEY: Unsure
<222> LOCATION: 416
<223> OTHER INFORMATION: n= any nucleotide
<221> NAME/KEY: Unsure
<222> LOCATION: 421
<223> OTHER INFORMATION: n= any nucleotide
<221> NAME/KEY: Unsure
<222> LOCATION: 424
<223> OTHER INFORMATION: n= any nucleotide
<221> NAME/KEY: Unsure
<222> LOCATION: 426
<223> OTHER INFORMATION: n= any nucleotide
<221> NAME/KEY: Unsure
<222> LOCATION: 451
<223> OTHER INFORMATION: n= any nucleotide
<221> NAME/KEY: Unsure
<222> LOCATION: 452
<223> OTHER INFORMATION: n= any nucleotide
<221> NAME/KEY: Unsure
<222> LOCATION: 462
<223> OTHER INFORMATION: n= any nucleotide
<221> NAME/KEY: Unsure
<222> LOCATION: 463
<223> OTHER INFORMATION: n= any nucleotide
<221> NAME/KEY: Unsure
<222> LOCATION: 466
<223> OTHER INFORMATION: n= any nucleotide
<221> NAME/KEY: Unsure
<222> LOCATION: 468
<223> OTHER INFORMATION: n= any nucleotide
<221> NAME/KEY: Unsure
<222> LOCATION: 469
```

<223> OTHER INFORMATION: n= any nucleotide
<221> NAME/KEY: Unsure
<222> LOCATION: 471
<223> OTHER INFORMATION: n= any nucleotide
<221> NAME/KEY: Unsure
<222> LOCATION: 486
<223> OTHER INFORMATION: n= any nucleotide
<221> NAME/KEY: Unsure
<222> LOCATION: 489
<223> OTHER INFORMATION: n= any nucleotide
<221> NAME/KEY: Unsure
<222> LOCATION: 495
<223> OTHER INFORMATION: n= any nucleotide
<221> NAME/KEY: Unsure
<222> LOCATION: 497
<223> OTHER INFORMATION: n= any nucleotide
<221> NAME/KEY: Unsure
<222> LOCATION: 502
<223> OTHER INFORMATION: n= any nucleotide
<221> NAME/KEY: Unsure
<222> LOCATION: 503
<223> OTHER INFORMATION: n= any nucleotide
<221> NAME/KEY: Unsure
<222> LOCATION: 504
<223> OTHER INFORMATION: n= any nucleotide

<400> SEQUENCE: 6
aattcggcac agctcttcag gaagtcagac cttccctggt ttacctttt tctggaaaaa     60 gcccaactgg gactccagtc agtaggaaag tgccacaatt gtcacatgac cggtactgga    120
agaaactctc ccatccaaca tcacccagtg gnatgggaac actgatgaac ttttcactgc    180
acttggcatt attttgtna agctgaatgt gataataagg gcactgatgg aaatgtctgg    240
atcattccgg ttgtgcgtac tttgagattt gngtttgggg atgtncattg tgtttgacag    300 cactttttn atccctaatg tnaaatgcnt natttgattg tganttgggg gtnaacattg    360
gtnaaggntn cccntntgac acagtagntg gtncccgact tanaatngnn gaanangatg    420
natnangaac ctttttttgg gtgggggggt nncggggcag tnnaangnng nctccccagg    480
tttggngtng caatngngga annntgg                                        507

<210> SEQ ID NO 7
<211> LENGTH: 226
<212> TYPE: DNA
<213> ORGANISM: Homo sapiens

<400> SEQUENCE: 7
ttttttttgt agatggatct tacaatgtag cccaaataaa taaataaagc atttacatta     60
ggataaaaaa gtgctgtgaa aacaatgaca tcccaaacca aatctcaaag tacgcacaaa    120
cggaatgatc cagacatttc cataggtcct tattatcaca ttcagcttat aaaataatgc    180
caagtgcagt gaaaagttac aggatgttcc atccactggg tggatt                   226

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 8
cgcccatgga gtctgctctg atcac                                           25

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 9
cgcaagcttt tagcctgatt ctttgtggac                              30

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 10
cgcggatccg ccatcatgga acaacgggga cagaac                       36

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 11
cgcggtacct taggacatgg cagagtc                                 27

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 12
cgcggtacct tagcctgatt ctttgtggac                              30

<210> SEQ ID NO 13
<211> LENGTH: 733
<212> TYPE: DNA
<213> ORGANISM: Homo sapiens

<400> SEQUENCE: 13
gggatccgga gcccaaatct tctgacaaaa ctcacacatg cccaccgtgc ccagcacctg    60
aattcgaggg tgcaccgtca gtcttcctct tccccccaaa acccaaggac accctcatga   120
tctcccggac tcctgaggtc acatgcgtgg tggtggacgt aagccacgaa gaccctgagg   180
tcaagttcaa ctggtacgtg gacggcgtgg aggtgcataa tgccaagaca aagccgcggg   240
aggagcagta caacagcacg taccgtgtgg tcagcgtcct caccgtcctg caccaggact   300
ggctgaatgg caaggagtac aagtgcaagg tctccaacaa agccctccca acccccatcg   360
agaaaaccat ctccaaagcc aaagggcagc ccgagaacc acaggtgtac accctgcccc   420
catcccggga tgagctgacc aagaaccagg tcagcctgac ctgcctggtc aaaggcttct   480
atccaagcga catcgccgtg gagtgggaga gcaatgggca gccggagaac aactacaaga   540
ccacgcctcc cgtgctggac tccgacggct ccttcttcct ctacagcaag ctcaccgtgg   600
acaagagcag gtggcagcag gggaacgtct tctcatgctc cgtgatgcat gaggctctgc   660
acaaccacta cacgcagaag agcctctccc tgtctccggg taaatgagtg cgacggccgc   720
gactctagag gat                                                     733

<210> SEQ ID NO 14

-continued

```
<211> LENGTH: 257
<212> TYPE: DNA
<213> ORGANISM: Homo sapiens
<220> FEATURE:
<221> NAME/KEY: Unsure
<222> LOCATION: 37
<223> OTHER INFORMATION: n= any nucleotide
<221> NAME/KEY: Unsure
<222> LOCATION: 79
<223> OTHER INFORMATION: n= any nucleotide
<221> NAME/KEY: Unsure
<222> LOCATION: 81
<223> OTHER INFORMATION: n= any nucleotide
<221> NAME/KEY: Unsure
<222> LOCATION: 124
<223> OTHER INFORMATION: n= any nucleotide
<221> NAME/KEY: Unsure
<222> LOCATION: 233
<223> OTHER INFORMATION: n= any nucleotide

<400> SEQUENCE: 14
agggctgaaa cccacgggcc tgagagacta taagagngtt ccctaccgcc atggaacaac        60
ggggacagaa cgccccggnc ncttcggggg cccggaaaag gcacggccca ggacccaggg       120
aggngcgggg agccaggcct gggccccggg tccccaagac ccttgtgctc gttgtcgccg       180
cggtcctgct gttggtgagt ccccgccgcg gtccctggct ggggaagagc gtncctggcg       240
cctggagagg gcaggga                                                     257
```